US010066264B2

(12) United States Patent
Hayashizaki et al.

(10) Patent No.: US 10,066,264 B2
(45) Date of Patent: *Sep. 4, 2018

(54) METHOD FOR ANALYZING TARGET NUCLEIC ACID, KIT, AND ANALYZER

(71) Applicant: KABUSHIKI KAISHA DNAFORM, Yokohama-shi, Kanagawa (JP)

(72) Inventors: Yoshihide Hayashizaki, Tsukuba (JP); Masayoshi Itoh, Tokyo (JP); Takahiro Arakawa, Kawasaki (JP); Kengo Usui, Yokohama (JP); Sotaro Uemura, Yokohama (JP); Yasumasa Mitani, Yokohama (JP)

(73) Assignee: KABUSHIKI KAISHA DNAFORM, Kanagawa (JP)

( * ) Notice: Subject to any disclaimer, the term of this patent is extended or adjusted under 35 U.S.C. 154(b) by 731 days.

This patent is subject to a terminal disclaimer.

(21) Appl. No.: 14/414,324

(22) PCT Filed: Aug. 29, 2013

(86) PCT No.: PCT/JP2013/073233
§ 371 (c)(1),
(2) Date: Jan. 12, 2015

(87) PCT Pub. No.: WO2014/034818
PCT Pub. Date: Mar. 6, 2014

(65) Prior Publication Data
US 2015/0152496 A1    Jun. 4, 2015

(30) Foreign Application Priority Data
Aug. 30, 2012    (JP) .................................. 2012-190715

(51) Int. Cl.
*C12Q 1/68*     (2018.01)
*C12Q 1/6876*   (2018.01)
(Continued)

(52) U.S. Cl.
CPC ........... *C12Q 1/6876* (2013.01); *C12Q 1/682* (2013.01); *C12Q 1/6834* (2013.01); *C12Q 1/6853* (2013.01); *C12Q 2600/158* (2013.01)

(58) Field of Classification Search
None
See application file for complete search history.

(56) References Cited

U.S. PATENT DOCUMENTS

2008/0227104 A1* 9/2008 Hayashizaki et al. .......................
C12Q 1/6853
435/6.11
2010/0092971 A1    4/2010 Okamoto et al.
(Continued)

FOREIGN PATENT DOCUMENTS

EA    201491064    11/2014
EP    0 639 647    2/1995
(Continued)

OTHER PUBLICATIONS

Poulsen et al., "Investigation of Parameters that Affect the Success Rate of Microarray-Based Allele-Specific Hybridization Assays," PLoS One 2011, 6(3):e14777.*
(Continued)

*Primary Examiner* — Kaijiang Zhang
(74) *Attorney, Agent, or Firm* — Hamre, Schumann, Mueller & Larson, P.C.

(57) ABSTRACT

The present invention is to provide a method for analyzing a target nucleic acid, by which the target nucleic acid can be analyzed rapidly and easily. In order to achieve the above object, the present invention provides a method for analyzing a target nucleic acid in a sample, including the step of: analyzing the target nucleic acid in the sample by bringing the sample into contact with a label and with a primer or probe that can hybridize to the target nucleic acid. The primer or probe is immobilized on a solid phase. The label
(Continued)

does not emit light when the primer or probe does not hybridize to the target nucleic acid, whereas the label emits light when the primer or probe has hybridized to the target nucleic acid. The analysis is carried out by detecting the light emitted from the label.

34 Claims, 25 Drawing Sheets

Specification includes a Sequence Listing.

(51) Int. Cl.
    *C12Q 1/682* (2018.01)
    *C12Q 1/6834* (2018.01)
    *C12Q 1/6853* (2018.01)

(56) References Cited

U.S. PATENT DOCUMENTS

| | | | |
|---|---|---|---|
| 2011/0151459 | A1 | 6/2011 | Rothmann et al. |
| 2013/0289263 | A1 | 10/2013 | Okamoto et al. |
| 2015/0203902 | A1* | 7/2015 | Hayashizaki et al. ........................ C12Q 1/6818 435/6.11 |

FOREIGN PATENT DOCUMENTS

| | | |
|---|---|---|
| EP | 1 970 453 | 9/2008 |
| EP | 2 130 835 | 12/2009 |
| EP | 2 660 246 | 11/2013 |
| EP | 2 873 731 | 5/2015 |
| JP | 7-023800 | 1/1995 |
| JP | 10-505492 | 6/1998 |
| JP | 2009-171935 | 8/2009 |
| JP | 4370385 B | 11/2009 |
| JP | 2011-519570 | 7/2011 |
| JP | 4761086 B | 8/2011 |
| WO | 96/04404 | 2/1996 |
| WO | 00/29613 | 5/2000 |
| WO | 02/29085 | 4/2002 |
| WO | 2008/111485 | 9/2008 |
| WO | 2012/091091 | 7/2012 |
| WO | 2014/013954 | 1/2014 |

OTHER PUBLICATIONS

Poulsen et al., "Multi-stringency wash of partially hybridized 60-mer probes reveals that the stringency along the probe decreases with distance from the microarray surface," Nucleic Acids Res. 2008, 36(20):e132.*
De Paul et al., "Tuned Graft Copolymers as Controlled Coatings for DNA Microarrays," Anal. Chem. 2005, 77(18):5831-5838.*
Ikeda et al., "Exciton-Controlled Hybridization-Sensitive Fluorescent Probes: Multicolor Detection of Nucleic Acids", Angewandte Chemie (International Edittion), vol. 48, No. 35, pp. 6480-6484, 2009.
Sugizaki et al., "Echo-LNA Conjugates: Hybridization-Sensitive Fluorescence and Its Application to Fluorescent Detection of Various RNA Strands", Bioconjugate Chemistry, vol. 21, No. 12, pp. 2276-2281, 2010.
Hanami et al., "Eprobe Mediated Real-Time PCR Monitoring and Melting Curve Analysis", PLoS One, vol. 8, Issue 8, p. E70942-1, 2013.
Okamoto et al., "A nucleic acid probe labeled with desmethyl thiazole orange: a new type of hybridization-sensitive flourescent oligonucleotide for live-cell RNA imaging", Organic & Biomolecular Chemistry, vol. 11, No. 2, pp. 362-371, 2013.
Supplementary European Search Report of the corresponding European Patent Application No. 13832285.4, dated Apr. 8, 2016, 10 pages.

Office Action issued for corresponding Eurasian Patent Application No. 201590455, dated Jun. 20, 2016, 4 pages with translation.
Office Action of the corresponding Eurasian Patent Application No. 201590455, dated Feb. 15, 2017, 4 pages with full English translation.
Kawai et al., "Development of SmartAmp2-Based Technology for Rapid Detection of the 2009 Pandemic Influenza A/H1N1 Virus", 14th International Conference on Miniaturized Systems for Chemistry and Life Sciences Oct. 3-7, 2010, Groningen, the Netherlands, pp. 1493-1495.
Suzuki et al., "The transcriptional network that controls growth arrest and differentiation in a human myeloid leukemia cell line", Nature Genetics, vol. 41, pp. 553-562, 2009 with its Supplementary Information.
Faulkner et al., "The regulated retrotransposon transcriptome of mammalian cells", Nature Genetics, vol. 41, pp. 563-571, 2009 with its Supplementary Information.
Taft et al., "Tiny RNAs associated with transcription start sites in animals",Nature Genetics, vol. 41, pp. 572-578, 2009 with its Supplementary Information.
Rye et al., "High-sensitivity two-color detection of double-stranded DNA with a confocal fluorescence gel scanner using ethidium homodimer and thiazole orange", Nucleic Acids Research, vol. 19, No. 2, pp. 327-333,1991.
Lee et al., "Thiazole Orange: A New Dye for Reticulocyte Analysis", Cytometry, vol. 7, pp. 508-517, 1986.
Svanvik et. al., "Light-Up Probes: Thiazole Orange-Conjugated Peptide Nucleic Acid for Detection of Target Nucleic Acid in Homogeneous Solution", Analytical Biochemistry, vol. 281, pp. 26-35, 2000.
Hrdlicka et al., "Multilabeled Pyrene-Functionalized 2'-Amino-LNA Probes for Nucleic Acid Detection in Homogeneous Fluorescence Assays", J. Am. Chem. Soc., vol. 127, pp. 13293-13299, 2005 with its Supporting Information.
Carreon et al., "Thiazole Orange-Peptide Conjugates: Sensitivity of DNA Binding to Chemical Structure", Organic Letters, vol. 6, pp. 517-519, 2004 with its Supporting Information.
Ikeda et al., "Hybridization-Sensitive On-Off DNA Probe: Application of the Exciton Coupling Effect to Effective Fluorescence Quenching", Chemistry—An Asian Journal, vol. 3, No. 6, pp. 958-968, 2008.
Lezhava et al., "Exciton Primer-Mediated SNP Detection in SmartAmp2 Reactions", Human Mutation, vol. 31, No. 2, pp. 208-217, 2010.
Okamoto et al., "Echo probes: a concept of fluorescence control for practical nucleic acid sensing", Chem. Soc. Rev., vol. 40, No. 12, pp. 5815-5828, 2011.
Kimura et al., "Effect of Thiazole Orange Doubly Labeled Thymidine on DNA Duplex Formation", Biochemistry, vol. 51, No. 31, pp. 6056-6067, 2012.
Tyagi et al., "Molecular Beacons: Probes that Fluoresce upon Hybridization", Nat. Biotechnol., vol. 14, pp. 303-308, 1996.
Nazarenko et al., "A closed tube format for amplification and detection of DNA based on energy transfer", Nucleic Acids Res., vol. 25, No. 12, pp. 2516-2521, 1997.
Gelmini et al., "Quantitative polymerase chain reaction-based homogeneous assay with fluorogenic probes to measure c-erbB-2 oncogene amplification", Clin. Chem., vol. 43, No. 5, pp. 752-758, 1997.
Whitcombe et al., "Detection of PCR products using self-probing amplicons and fluorescence", Nat. Biotechnol., vol. 17, pp. 804-807, 1999.
Sambrook et al., "Molecular cloning : A laboratory manual", Protocol 15 Quantative PCR, p. 8.86, Cold Spring Harbor Laboratory Press, 2nd edition, 1989.
Ashwell et al., "The synthesis and antiviral properties of (E)-5-(2-bromovinyl)-2'-deoxyuridine-related compounds", Tetrahedron, vol. 43, Iss. 20, pp. 4601-4608, 1987.
Carreon et al., "Thiazole Orange-Peptide Conjugates: Sensitivity of DNA Binding to Chemical Structure", Organic Letters, vol. 6, Iss. 4, pp. 517-519, 2004 (with Supporting Information).
Custom Synthesis Service of Novel Fluorescent Hybridazation Probe (Exciton Probe), [online] Issued by Kabushiki Kaisha

(56) References Cited

OTHER PUBLICATIONS

DNAForm, Mar. 22, 2012 [retrieval date: Aug. 12, 2013] Internet <URL:http://dnaform.jp/pdf/ExcitonProbe.pdf>—with an English translation.

Cradic et al., "Substitution of 3'-Phosphate Cap with a Carbon-Based Blocker Reduces the Possibility of Fluorescence Resonance Energy Transfer Probe Failure in Real-Time PCR Assays", Clinical Chemistry, vol. 50, No. 6, pp. 1080-1082, 2004.

2008 Price List, [online] issued by Eurogentec, p. 18, 2008 [retrieval date: Aug. 12, 2013] Internet <URL: http://www.eurogentec.com/EGT/files/Glen-Research/GLENRES-PRICELIST.pdf>.

Okamoto, "Live cell imaging of mRNA by chemically designed fluorescent nucleic acids", Experimental Medicine, vol. 26, No. 17 (extra issue), pp. 2850-2856, 2008—with an English translation.

Okamoto, "Echo probes: a concept of fluorescence control for practical nucleic acid sensing", Chem. Soc. Rev., vol. 40, pp. 5815-5828, 2011.

Ikeda et al., "Sequence Dependence of Fluorescence Emission and Quenching of Doubly Thiazole Orange Labeled DNA: Effective Design of a Hybridization-Sensitive Probe", Bioconjugate Chemistry, vol. 19, No. 8, pp. 1719-1725, 2008.

Lezhava et al., "Exciton Primer-Mediated SNP Detection in SmartAmp2 Reactions", Human Mutation, vol. 31, No. 2, pp. 208-217 (2010).

Kimura et al., "Effect of Thiazole Orange Doubly Labeled Thymidine on DNA Duplex Formation", Biochemistry, vol. 51, No. 31, pp. 6056-6067 (2012).

Extended European Search Report in the corresponding European Patent Application No. 13820349.2, Mar. 29, 2016, 14 pages.

Office Action issued in corresponding European Patent Application No. 13820349.2, dated Feb. 20, 2017, 5 pages.

\* cited by examiner

SEQUENCE LISTING

```
<160> NUMBER OF SEQ ID NOS: 17

<210> SEQ ID NO 1
<211> LENGTH: 29
<212> TYPE: DNA
<213> ORGANISM: Artificial Sequence
<220> FEATURE:
<223> OTHER INFORMATION: primer

<400> SEQUENCE: 1
aaaaaaaaaa ggcatgggtc agaaggatt                                     29

<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2
aaaaaaaaaa aggtgtggtg ccagattttc                                    30

<210> SEQ ID NO 3
<211> LENGTH: 47
<212> TYPE: DNA
<213> ORGANISM: Artificial Sequence
<220> FEATURE:
<223> OTHER INFORMATION: primer

<400> SEQUENCE: 3
ctaatacgac tcactatagg gagaatggat gatgatatcg ccgcgct                 47

<210> SEQ ID NO 4
<211> LENGTH: 34
<212> TYPE: DNA
<213> ORGANISM: Artificial Sequence
<220> FEATURE:
<223> OTHER INFORMATION: primer

<400> SEQUENCE: 4 cattttttaag gtgtgcactt ttattcaact ggtc                              34

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
```
ggcatgggtc agaaggatt                                            19

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
aggtgtggtg ccagattttc                                           20

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
ggcatgggtc agaaggatt                                            19

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
aggtgtggtg ccagattttc                                           20

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
aaaaaaaaaa ggcatgggtc agaaggatt                                 29

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
aaaaaaaaaa aggtgtggtg ccagattttc                                30

<210> SEQ ID NO 11
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(10)
<223> OTHER INFORMATION: n represents thymine introduced dye label
      having exciton effect

<400> SEQUENCE: 11
ggcatgggtn cagaaggatt                                           20

```
<210> SEQ ID NO 12
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(10)
<223> OTHER INFORMATION: n represents thymine introduced dye label
      having exciton effect

<400> SEQUENCE: 12
aggtgtggtn gccagatttt c                                              21

<210> SEQ ID NO 13
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(10)
<223> OTHER INFORMATION: n represents thymine introduced dye label
      having exciton effect

<400> SEQUENCE: 13
ggcatgggtn cagaaggatt                                                20

<210> SEQ ID NO 14
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(10)
<223> OTHER INFORMATION: n represents thymine introduced dye label
      having exciton effect

<400> SEQUENCE: 14
aggtgtggtn gccagatttt c                                              21

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
aaaaaaaaaa ggcatgggtc agaaggatt                                      29

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
ggcatgggtc agaaggatt                                                 19

<210> SEQ ID NO 17
<211> LENGTH: 20
```

```
<212> TYPE: DNA
<213> ORGANISM: Artificial Sequence
<220> FEATURE:
<223> OTHER INFORMATION: primer

<400> SEQUENCE: 17
aggtgtggtg ccagattttc                                        20
```

METHOD FOR ANALYZING TARGET NUCLEIC ACID, KIT, AND ANALYZER

TECHNICAL FIELD

The present invention relates to a method, a kit, and an analyzer for analyzing a target nucleic acid.

BACKGROUND ART

Genotyping including analysis of single nucleotide polymorphisms (SNPs) and gene mutations can provide the basis for "tailor-made medicine", and the need for genotyping is growing rapidly. With the aim of reducing the side effects of pharmaceuticals, the United States Food and Drug Administration is now trying to make it mandatory for the applicants of new drugs to attach information regarding SNPs and gene mutations relevant to the effect of the drugs. Also in Japan, there is a growing demand for analysis of SNPs and gene mutations.

A device for determining the copy number of a nucleic acid or a mutation(s) in a nucleic acid is used widely for academic and clinical purposes. There have been discovered many biomarkers with which the reactivity to a drug, the prognosis of a disease, etc. can be predicted by examining the copy number of one gene or a mutation(s) in one gene. Examples of such biomarkers include those for Iressa and Herceptin. However, in many cases, high accuracy prediction cannot be achieved with the use of only one biomarker, because the homeostasis in vivo is maintained while being regulated by various networks.

Particularly in recent years, there has been proposed the concept of the "Basin Network", which is formed by transcription factors and non-coding RNAs (ncRNAs) in relation to each other (Non-Patent Documents 1 to 3). For the maintenance of cell morphology, the limited number of transcription factors and ncRNAs always interact with each other at every level of the central dogma, and in particular, it is considered that the regulation at the transcriptional level contributes greatly to the maintenance of cell morphology. The concentrations of these specific transcription factors and ncRNAs in a nucleus are either constant or oscillating within a given range, and never deviate from the range. Once they deviate, the balance of the network formed between the transcription factors and the ncRNAs in the nucleus changes and shifts to a subsequent form of the network. In this way, the morphology of the cell shifts to a subsequent form such as differentiation, canceration, or senescence.

CITATION LIST

Patent Document(s)

Non-Patent Document 1: Nature Genetics 41, 553-562 (2009)
Non-Patent Document 2: Nature Genetics 41, 563-571 (2009)
Non-Patent Document 3: Nature Genetics 41, 572-578 (2009)

BRIEF SUMMARY OF THE INVENTION

Problem to be Solved by the Invention

The Basin Network is a network that performs regulation at the transcriptional level in nuclei. However, the Basin Network actually affects the regulation at the following levels: epigenomic states (modification such as heterochromatin formation and DNA methylation) of genomic DNAs in nuclei; degradation and metabolism of RNA itself, such as RNA interference; the translational level of RNA; and further, at levels where proteins function, such as direct binding to proteins. Thus, with the current state of the art, even if the state of RNA or DNA is examined with reference to one gene, it is not possible to predict how these networks function. In order to diagnose the prognosis of a cancer, the reactivity to a drug (whether a subject is a responder or non-responder to the drug) as will be described below, and the like, a technique is required that can measure and define the functional state of a cell. Besides, genes such as transcription factors and ncRNAs that contribute to these regulatory states exhibit low expression levels by their nature, and the changes in expression level of these genes have to be detected in the state where they exhibit physiological activity, i.e., when they are expressed at low levels. Furthermore, in actual clinical practice, it is required that the expression levels of these genes are measured easily in an outpatient department, an operating room, etc., and that the result of the measurement can be obtained right away.

With the foregoing in mind, it is an object of the present invention to provide a method, a kit, and an analyzer for analyzing a target nucleic acid, which allow the target nucleic acid to be analyzed rapidly and easily.

Means for Solving Problem

In order to achieve the above object, the present invention provides a method for analyzing a target nucleic acid in a sample, including the step of: analyzing the target nucleic acid in the sample by bringing the sample into contact with a label and with a primer or probe that can hybridize to the target nucleic acid. In this method, the primer or probe is immobilized on a solid phase. The label does not emit light when the primer or probe does not hybridize to the target nucleic acid, whereas the label emits light when the primer or probe has hybridized to the target nucleic acid, and the analysis is carried out by detecting the light emitted from the label.

The present invention also provides a kit for carrying out the method according to the present invention. The kit includes: the primer or probe; the label; and a support on which the primer or probe is to be immobilized. In this kit, the support includes the solid phase.

The present invention also provides an analyzer for carrying out the method according to the present invention. The analyzer includes: a light emission detection unit for detecting light emitted from the label.

Effects of the Invention

According to the target nucleic acid analysis method, kit, and analyzer of the present invention, it is possible to analyze a target nucleic acid rapidly and easily.

MODE FOR CARRYING OUT THE INVENTION

Figure 1:
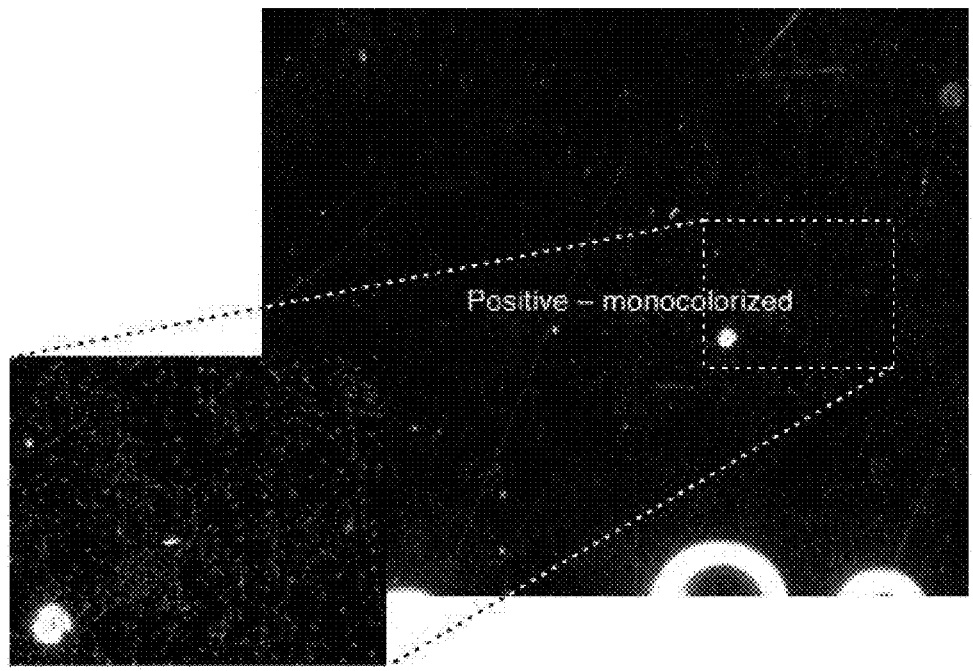
FIG. 1 show photographs demonstrating that an amplification product of a target nucleic acid was produced when a primer pair was used in Example 1.

Hereinafter, the present invention will be described more specifically with reference to illustrative examples. It is to be noted, however, that the present invention is not limited by the following descriptions.

The present invention also can be described as in the following items [1] to [46], for example. It is to be noted, however, that the present invention is by no means limited thereto.

[1] A method for analyzing a target nucleic acid in a sample, the method including the step of:

analyzing the target nucleic acid in the sample by bringing the sample into contact with a label and with a primer or probe that can hybridize to the target nucleic acid, wherein the primer or probe is immobilized on a solid phase, the label does not emit light when the primer or probe does not hybridize to the target nucleic acid, whereas the label emits light when the primer or probe has hybridized to the target nucleic acid, and the analysis is carried out by detecting the light emitted from the label.

[2] The method described in the item [1], wherein after the analysis of the target nucleic acid, the target nucleic acid is removed to allow reuse of the primer or probe.

[3] The method described in the item [1] or [2], wherein there are two or more kinds of the target nucleic acids, and the respective target nucleic acids are detected separately.

[4] The method described in any one of the items [1] to [3], wherein two or more kinds of the primers or probes are used.

[5] The method described in any one of the items [1] to [4], wherein a surface of the solid phase on which the primer or probe is immobilized is a flat surface, a flat chip surface, a spherical surface, or a three-dimensional surface.

[6] The method described in any one of the items [1] to [5], wherein a surface of the solid phase is coated with a coating for reducing a background.

[7] The method described in the item [6], wherein the coating for reducing a background is provided by graft polymerization.

[8] The method described in any one of the items [1] to [7], wherein the label is a fluorescent dye moiety that exhibits an exciton effect.

[9] The method described in any one of the items [1] to [8], wherein the primer or probe includes the label as part thereof, and
the label is covalently bound to the primer or probe.

[10] The method described in the item [9], wherein the primer or probe is a nucleic acid molecule including at least one of structures represented by the following formulae (16), (16b), (17), (17b), (18), and (18b):

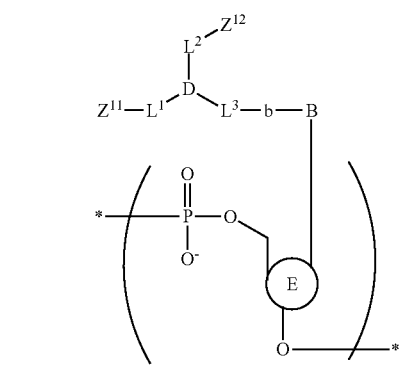

(16)

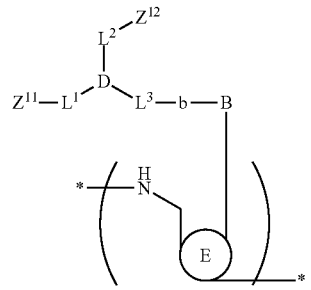

(16b)

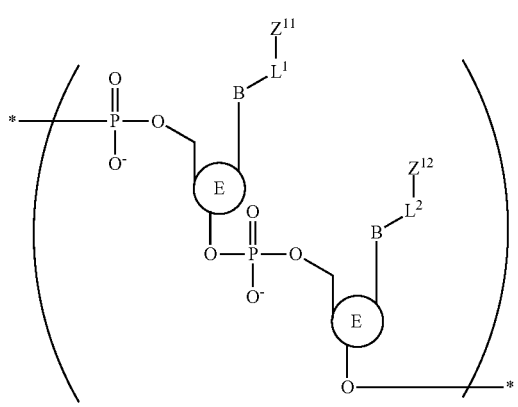

(17)

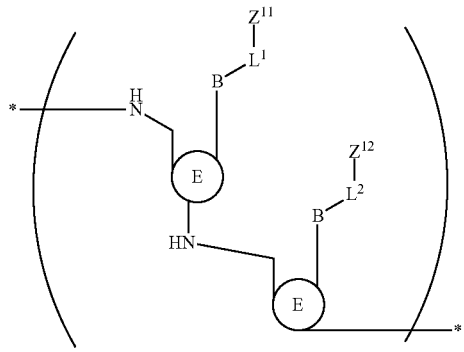

(17b)

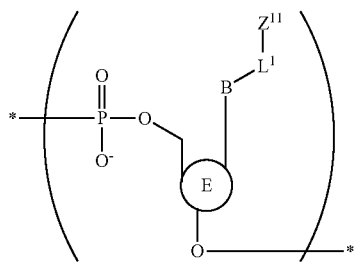

(18)

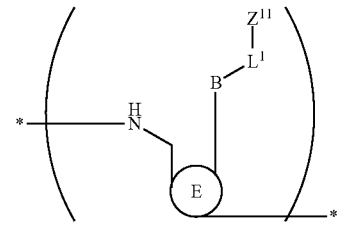

(18b)

where in the formulae (16), (16b), (17), (17b), (18), and (18b),

B is an atomic group having a natural nucleobase (adenine, guanine, cytosine, thymine, or uracil) skeleton or an artificial nucleobase skeleton, E is;

(i) an atomic group having a deoxyribose skeleton, a ribose skeleton, or a structure derived from either one of them; or (ii) an atomic group having a peptide structure or a peptoid structure, $Z^{11}$ and $Z^{12}$ are each a fluorescent dye moiety that exhibits an exciton effect, and may be identical to or different from each other, $L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other, D is CR, N, P, P=O, B, or SiR, and R is a hydrogen atom, an alkyl group, or an arbitrary substituent, and b is a single bond, a double bond, or a triple bond, or alternatively, in the formulae (16) and (16b), $L^1$ and $L^2$ are each the linker, $L^3$, D, and b may not be present, and $L^1$ and $L^2$ may be bonded directly to B, provided that:

in the formulae (16), (17), and (18), E is an atomic group described in the item (i), and at least one O atom in a phosphoric acid linkage may be substituted with an S atom;

in the formulae (16b), (17b), and (18b), E is an atomic group described in the item (ii); and in the formulae (17) and (17b), the respective Bs may be identical to or different from each other, and the respective Es may be identical to or different from each other.

[11] The method described in the item [10], wherein in the formulae (16), (17), (16b), (17b), (18), and (18b), the main chain length (the number of main chain atoms) of each of $L^1$, $L^2$, and $L^3$ is an integer of 2 or more.

[12] The method described in the item [10] or [11], wherein in the formulae (16), (17), (16b), (17b), (18), and (18b), $Z^{11}$ and $Z^{12}$ are each independently a group derived from any one of thiazole orange, oxazole yellow, cyanine, hemicyanine, other cyanine dyes, methyl red, azo dyes, biotin, and derivatives thereof.

[13] The method described in any one of the items [10] to [12], wherein $Z^{11}$ and $Z^{12}$ are each independently an atomic group represented by any one of the following formulae (7) to (9):

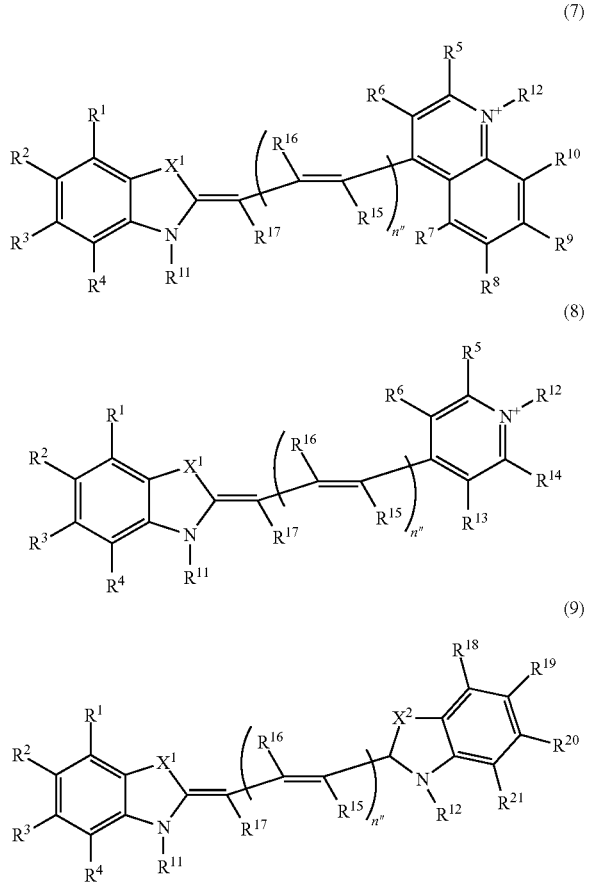

where in the formulae (7) to (9), $X^1$ and $X^2$ are S, O, or Se, n" is 0 or a positive integer, $R^1$ to $R^{10}$ and $R^{13}$ to $R^{21}$ are each independently a hydrogen atom, a halogen atom, a lower alkyl group, a lower alkoxy group, a nitro group, or an amino group, one of $R^{11}$ and $R^{12}$ is a linking group that is bound to $L^1$ or $L^2$ in the formulae (16), (17), (16b), and (17b), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively.

[14] The method described in the item [13], wherein in the formulae (7) to (9), in $R^1$ to $R^{21}$, the lower alkyl group is a linear or branched alkyl group with a carbon number of 1 to 6, and the lower alkoxy group is a linear or branched alkoxy group with a carbon number of 1 to 6.

[15] The method described in the item [13] or [14], wherein in the formulae (7) to (9), in $R^{11}$ and $R^{12}$, the linking group is a polymethylene carbonyl group with a carbon number of 2 or more and is bound to $L^1$ or $L^2$ in the formulae (16), (16b), (17), and (17b) in a carbonyl group moiety.

[16] The method described in any one of the items [13] to [15], wherein $Z^{11}$ and $Z^{12}$ are each independently an atomic group represented by the formula (7) or (8), and $Z^{11}$ and $Z^{12}$ represented by the formula (7) or (8) is a group represented by the following formula (19) or (20):

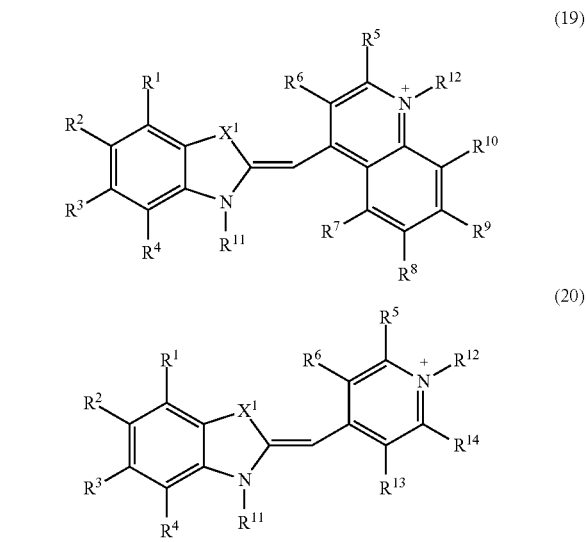

where in the formulae (19) and (20), $X^1$, $R^1$ to $R^{10}$, $R^{13}$ and $R^{14}$, and $R^{11}$ and $R^{12}$ are identical to those in the formulae (7) to (9).

[17] The method described in the item [16], wherein $Z^{11}$ and $Z^{12}$ are each independently an atomic group represented by the above formula (19), where in the formula (19), $X^1$ is S, $R^1$ to $R^{10}$ are hydrogen atoms, and one of $R^{11}$ and $R^{12}$ is a linking group that is bound to $L^1$ or $L^2$ in the formulae (16), (17), (16b), and (17b), and the other is a methyl group.

[18] The method described in the item [16], wherein $Z^{11}$ and $Z^{12}$ are each independently an atomic group represented by the above formula (19), where in the formula (19), $X^1$ is S, $R^1$, $R^4$, $R^5$, $R^6$, $R^7$, $R^9$, and $R^{10}$ are hydrogen atoms, $R^2$, $R^3$, and $R^{12}$ are methyl groups, $R^8$ is a halogen atom, and $R^{11}$ is a linking group that is bound to $L^1$ or $L^2$ in the formulae (16), (17), (16b), (17b), (18), and (18b).

[19] The method described in the item [13], wherein $Z^{11}$ and $Z^{12}$ are each independently an atomic group represented by the above formula (7), where in the formula (7), $X^1$ is S, n is 1, $R^1$ to $R^{10}$, $R^{15}$, $R^{16}$, and $R^{17}$ are hydrogen atoms, $R^{11}$ is a linking group that is bound to $L^1$ or $L^2$ in the formulae (16), (17), (16b), (17b), (18), and (18b), and $R^{12}$ is a methyl group.

[20] The method described in the item [13], wherein $Z^{11}$ and $Z^{12}$ are each independently an atomic group represented by any one of the following formulae:

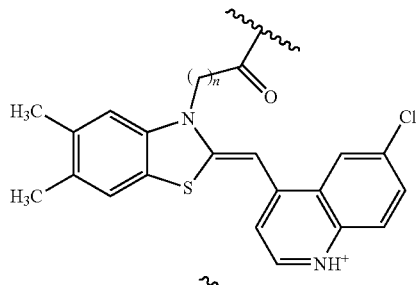

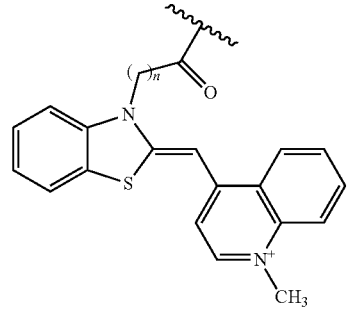

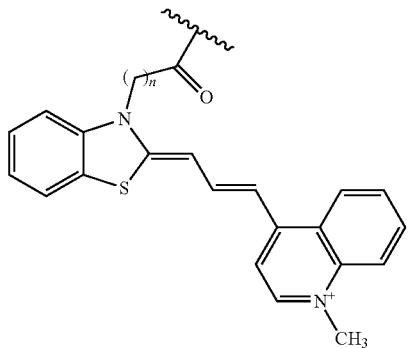

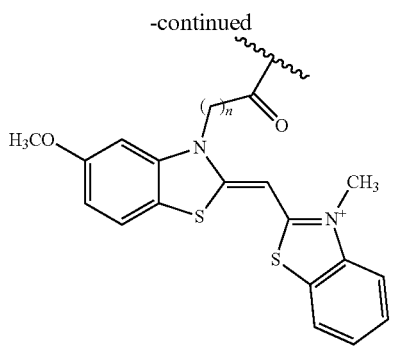

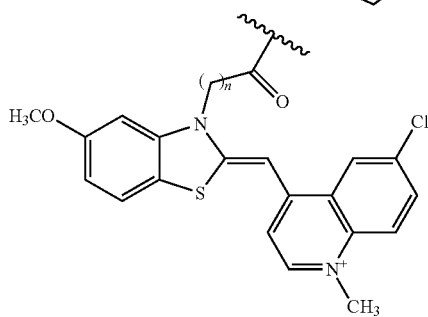

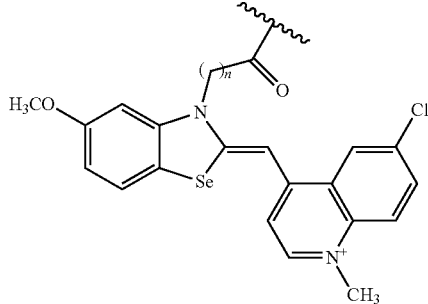

where in each of the above chemical formulae, n is a positive integer.

[21] The method described in any one of the items [10] to [20], wherein in the formulae (16), (17), (16b), (17b), (18), and (18b), B is an atomic group having a natural nucleobase (adenine, guanine, cytosine, thymine, or uracil) skeleton.

[22] The method described in any one of the items [10] to [20], wherein in the formulae (16), (17), (16b), (17b), (18), and (18b), B is an atomic group having an artificial nucleobase skeleton, and the artificial nucleobase is 2-amino-6-(N,N-dimethylamino)purine pyridin-2-one, 5-methylpyridin-2-one, 2-amino-6-(2-thienyl)purine, pyrrole-2-carbaldehyde, 9-methylimidazo[(4,5)-b]pyridine, 5-iodo-2-oxo(1H)pyridine 2-oxo-(1H)pyridine, 2-amino-6-(2-thiazolyl)purine, 7-(2-thienyl)-imidazo[4,5-b]pyridine, bromothymine, azaadenine, or azaguanine.

[23] The method described in any one of the items [10] to [20], wherein in the formulae (16), (17), (16b), (17b), (18), and (18b), B is an atomic group having an artificial nucleobase skeleton, and the artificial nucleobase is Py, Py der., Pu, or Pu der., the Py is an atomic group having a covalent bond to E in the 1-position and a covalent bond to a linker moiety in the 5-position in a six-membered ring represented by the following formula (11):

(11)

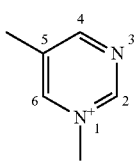

the Py der. is an atomic group in which at least one of all the atoms of the six-membered ring of the Py has been substituted with an N, C, S, or O atom, and the N, C, S, or O atom optionally may have an electric charge, a hydrogen atom, or a substituent, the Pu is an atomic group having a covalent bond to E in the 9-position and a covalent bond to a linker moiety in the 8-position in a condensed ring represented by the following formula (12):

(12)

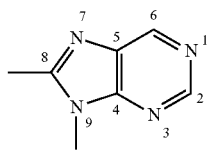

and the Pu der. is an atomic group in which at least one of all the atoms of a five-membered ring of the Pu has been substituted with an N, C, S, or O atom, and the N, C, S, or O atom optionally may have an electric charge, a hydrogen atom, or a substituent.

[24] The method described in any one of the items [10] to [23], wherein the structure represented by the formula (16) is a structure represented by the following formula (16-1) or (16-2), the structure represented by the formula (16b) is a structure represented by the following formula (16b-1) or (16b-2), the structure represented by the formula (17) is a structure represented by the following formula (17-1), the structure represented by the formula (17b) is a structure represented by the following formula (17b-1)

the structure represented by the formula (18) is a structure represented by the following formula (18-1), and the structure represented by the formula (18b) is a structure represented by the following formula (18b-1):

(16-1)

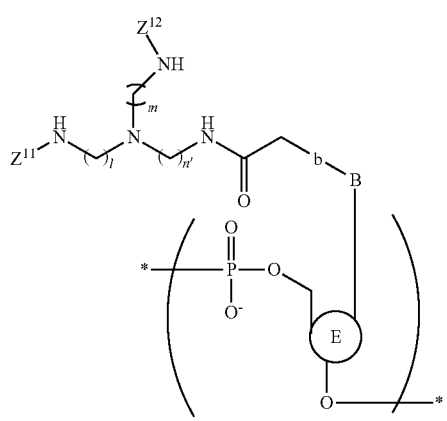

(16-2)

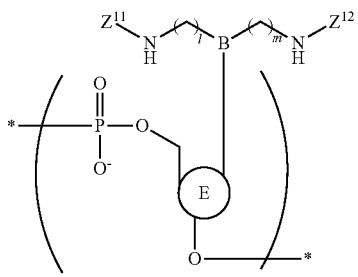

(16b-1)

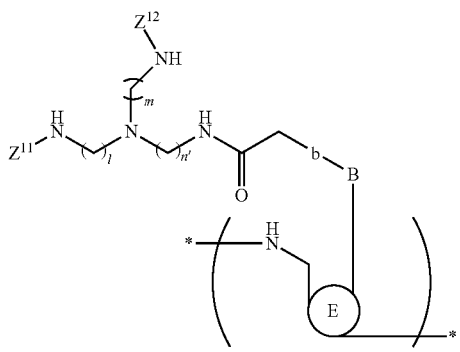

(16b-2)

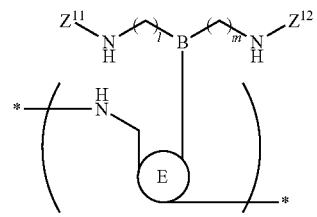

(17-1)

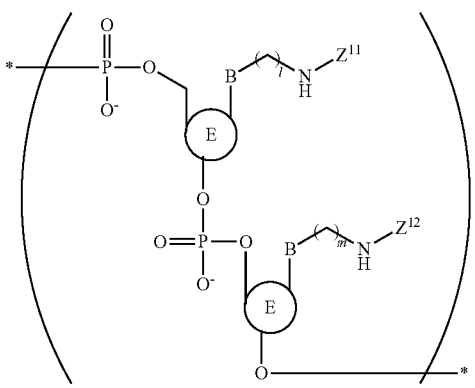

(17b-1)

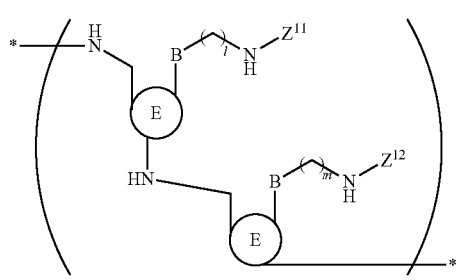

-continued

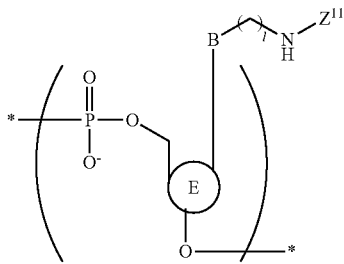

(18-1)

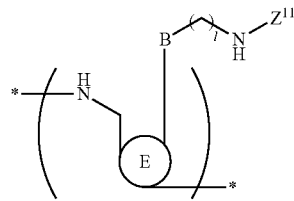

(18b-1)

where in the formulae (16-1), (16-2), (16b-1), (16b-2), (17-1), (17b-1), (18-1) and (18b-1), l, m and n' are arbitrary, l, m and n' may be identical to or different from each other, l, m and n' each may or may not contain each of C, N, O, S, P, and Si in a main chain thereof, and l, m and n' each may or may not contain each of a single bond, a double bond, a triple bond, an amide bond, an ester bond, a disulfide bond, an imino group, an ether bond, a thioether bond, and a thioester bond in the main chain, B, E, $Z^{11}$, $Z^{12}$, and b are identical to those in the formulae (16), (16b), (17), (17b), (18), and (18b), and in the formulae (16-1), (16-2), (17-1), and (18-1), at least one O atom in a phosphoric acid linkage may be substituted with an S atom.

[25] The method described in the item [24], wherein in the formulae (16-1), (16-2), (16b-1), (16b-2), (17-1), (17b-1), (18-1) and (18b-1), l, m, and n are each an integer of 2 or more.

[26] The method described in the item [10], wherein the nucleic acid molecule includes at least one of nucleotide structures represented by the following chemical formulae 106, 110, 113, 117, 120, 122, 123, 124, and 114-2, geometric isomers and stereoisomers thereof, and salts thereof:

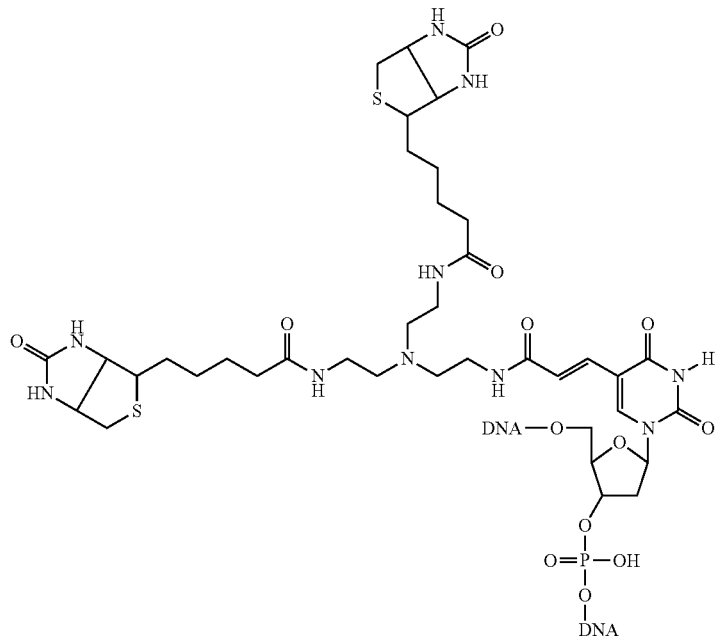

109

-continued
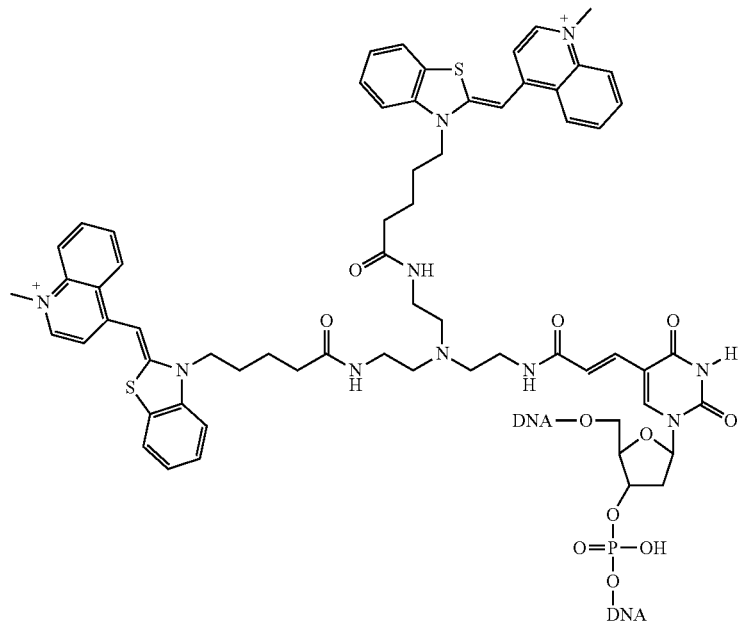
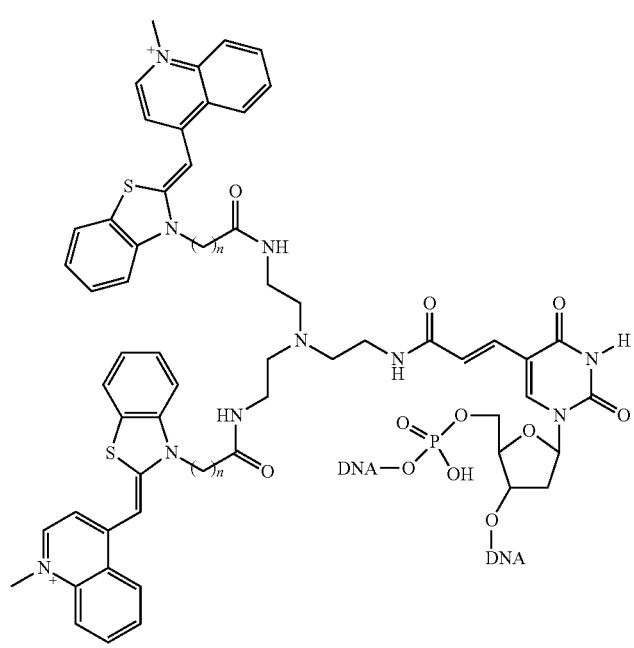

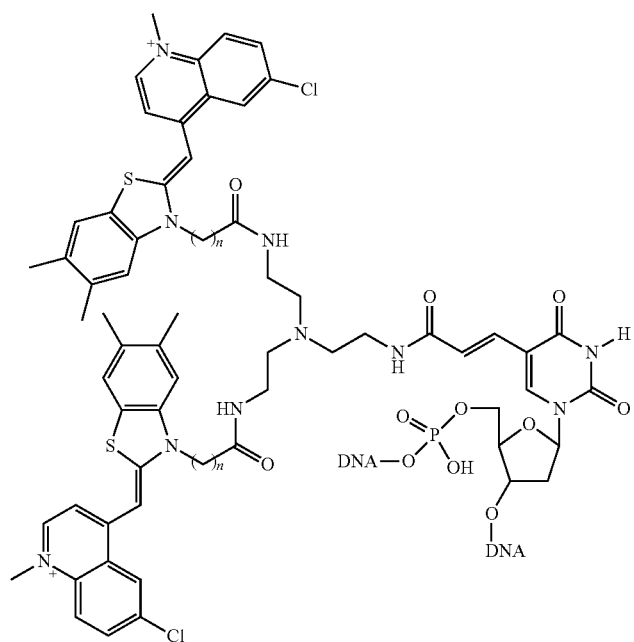
117
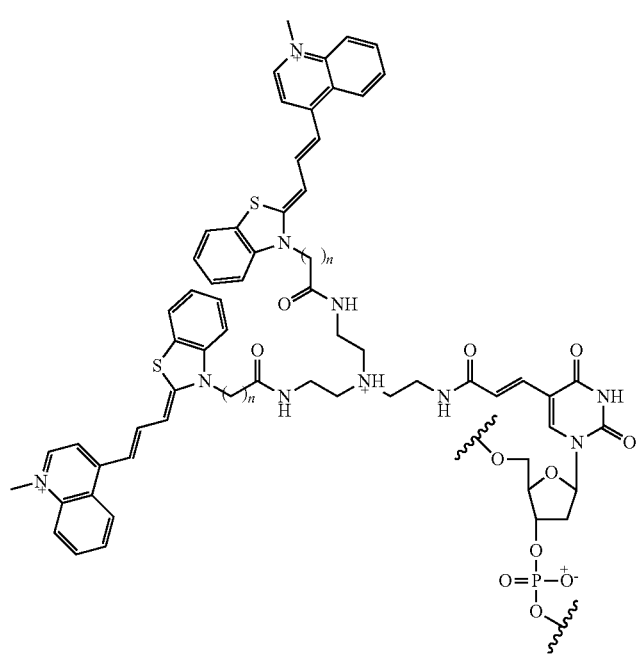
120

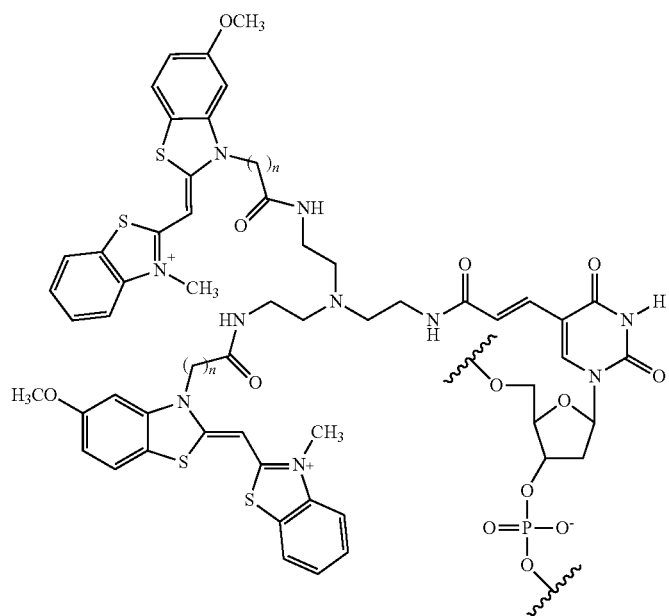
122
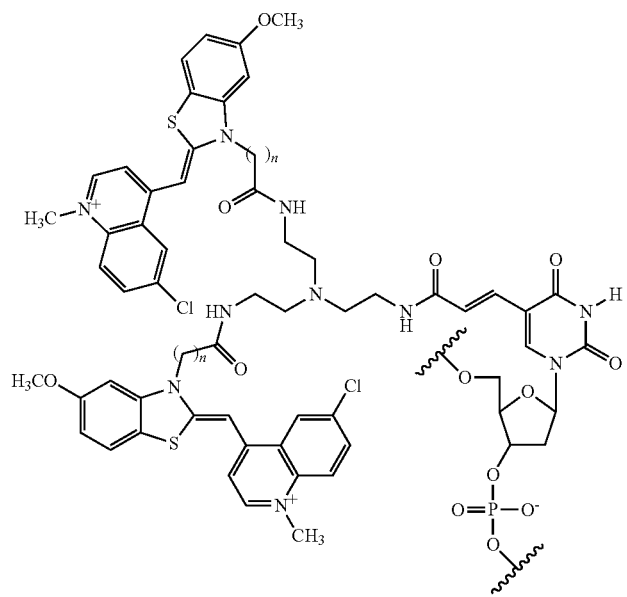
123

124

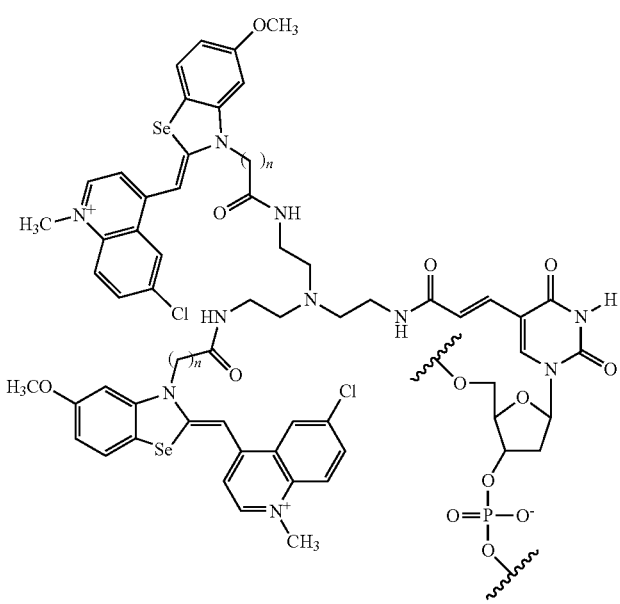

(114-2)

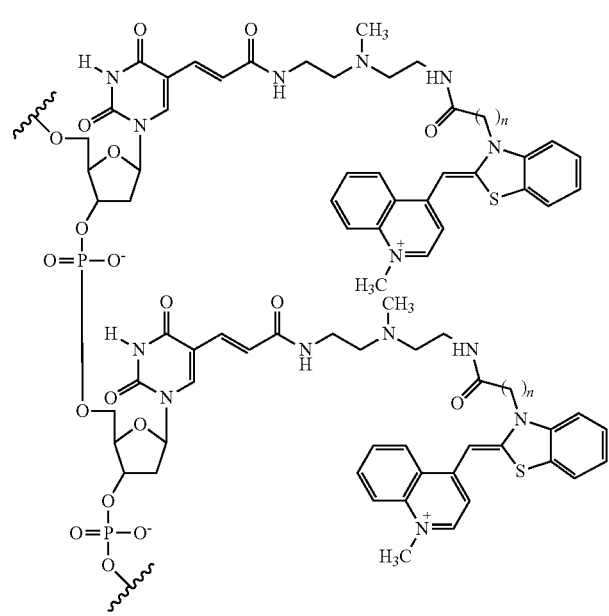

where in the chemical formulae 106, 110, 113, 117, 120, 122, 123, 124, and 114-2,
n is a positive integer.

[27] The method described in the item [20] or [26], wherein the linker length n is in the range from 2 to 6.

[28] The method described in any one of the items [1] to [27], wherein
the "primer or probe" is the primer,
the primer is hybridized to the target nucleic acid by bringing the primer into contact with the sample, thereby causing an amplification reaction of the target nucleic acid, and
the analysis of the target nucleic acid is carried out by further measuring the degree of amplification of the target nucleic acid in the amplification reaction over time.

[29] The method described in the item [28], wherein the amplification reaction of the target nucleic acid is caused by a bridge PCR method.

[30] The method described in the item [29], wherein
a primer pair is used as the primer,
each of primers in the primer pair includes the label covalently bound to the primer and thus includes the label as part thereof,
the labels covalently bound to the respective primers are each a fluorescent dye moiety that exhibits an exciton effect,
the labels are different from each other, and
in the bridge PCR method, the presence or absence of a mutation in a plurality of loci in the target nucleic acid is detected simultaneously or the expression levels of the plurality of loci are analyzed simultaneously by: adapting the labels to cause no fluorescence or fluorescence of one to three colors and carrying out fluorescent color analysis; or adapting the respective labels to exhibit fluorescence intensities different from each other and measuring the difference in fluorescence intensity.

[31] The method described in the item [29], wherein
a primer pair is used as the primer,
each of primers in the primer pair includes the label covalently bound to the primer and thus includes the label as part thereof,
the labels covalently bound to the respective primers are each a fluorescent dye moiety that exhibits an exciton effect,
the labels are different from each other, and
in the bridge PCR method, the proportion of mutations in the entire sample containing the target nucleic acid is determined by: adapting the labels to cause no fluorescence or fluorescence of one to three colors and carrying out fluorescent color analysis; or adapting the respective labels to exhibit fluorescence intensities different from each other and measuring the difference in fluorescence intensity.

[32] The method described in the item [29], wherein
a primer pair is used as the primer,
each of primers in the primer pair includes the label covalently bound to the primer and thus includes the label as part thereof,
the labels covalently bound to the respective primers are each a fluorescent dye moiety that exhibits an exciton effect,
the labels are different from each other, and
in the bridge PCR method, the quality of the sample containing the target nucleic acid is checked by: adapting the labels to cause no fluorescence or fluorescence of one to three colors and carrying out fluorescent color analysis; or adapting the respective labels to exhibit fluorescence intensities different from each other and measuring the difference in fluorescence intensity.

[33] The method described in the item [28], wherein
the amplification reaction of the target nucleic acid is caused by an isothermal amplification method.

[34] The method described in any one of the items [28] to [33], wherein
two or more spots on the primer are immobilized on the solid phase in an arbitrary positional relationship.

[35] The method described in any one of the items [28] to [34], wherein
the target nucleic acid is RNA,
the method further includes the step of causing a reverse transcription reaction of the RNA, and
the reverse transcription reaction is caused prior to the amplification reaction or at the same time with the amplification reaction on the solid phase having the primer immobilized thereon.

[36] The method described in any one of the items [28] to [35], wherein
the amplification reaction is caused using DNA polymerase, RNA polymerase, reverse transcriptase (reverse transcription polymerase), or RNA-dependent RNA polymerase.

[37] The method described in any one of the items [28] to [36], wherein
the presence or absence of a mutation in the target nucleic acid is detected by carrying out melting curve analysis after the amplification reaction.

[38] The method described in the item [37], wherein
the melting curve analysis is carried out using a probe, and
the probe includes a fluorescent dye moiety that exhibits an exciton effect.

[39] The method described in the item [38], wherein
two or more kinds of the probes each including a fluorescent dye moiety that exhibits an exciton effect are used.

[40] The method described in any one of the items [1] to [27], wherein
the "primer or probe" is the probe.

[41] The method described in the item [40], wherein
the sample contains the target nucleic acid that has been amplified beforehand.

[42] The method described in the item [40] or 41, wherein
the presence or absence of a mutation in the target nucleic acid is detected by further carrying out melting curve analysis.

[43] A kit for carrying out the method described in any one of the items [1] to [42], the kit including:
the primer or probe;
the label; and
a support on which the primer or probe is to be immobilized,
wherein the support includes the solid phase.

[44] An analyzer for carrying out the method described in any one of the items [1] to [42], the analyzer including:
a light emission detection unit for detecting light emitted from the label.

[45] The analyzer described in the item [44], further including:
a unit for acquiring at least one piece of snapshot data.

[46] The analyzer described in the item [44] or [45], further including:
a unit for acquiring data over time.

[Terms]

Some of the terms of the present invention (i.e., the terms used in the present specification) will be described below. The terms not defined specifically herein should be interpreted as having the same meaning as commonly understood by those skilled in the art. The abbreviations used for indicating DNAs, RNAs, nucleotides, polynucleotides, etc. are based on abbreviations specified in the "Guideline for Preparing Specifications Including Base Sequences and Amino Acid Sequences" (edited by the Japan Patent Office) and those commonly used in the art.

In the present invention, the term "polynucleotide" or "oligonucleotide" means a nucleic acid, which encompasses both DNA and RNA. The DNA encompasses cDNA, genomic DNA, and synthetic DNA. The RNA encompasses total RNA, mRNA, rRNA, siRNA, miRNA, snRNA, snoRNA, non-coding RNA, and synthetic RNA. Furthermore, in the present specification, the term "polynucleotide" or "oligonucleotide" is used interchangeably with the term "nucleic acid".

It is intended that the term "gene" used in the present invention not only means double-stranded DNA or double-stranded RNA but also encompasses the respective single-stranded DNAs included therein, such as a positive strand (or a sense strand) and a complementary strand (or an antisense strand). Also, the term "gene" is not particularly limited by the base sequence or the length of the sequence of the gene.

In the present invention, unless otherwise stated, the term "gene" encompasses: double-stranded DNA including human genomic DNA; single-stranded DNA (positive strand) including cDNA; single-stranded DNA having a complementary sequence (complementary strand) to the positive strand; fragments thereof; and human genomes. The "gene" as used herein does not necessarily mean the "gene" represented by a specific base sequence (or a specific sequence identification number), but also encompasses a "nucleic acid" encoding: RNA having an equivalent biological function to RNA encoded by the specific base sequence (e.g., a homolog); a mutant such as a polymorphism; and a derivative. Examples of the "nucleic acid" encoding such a homolog, a mutant, or a derivative include "nucleic acids"

each having a base sequence that hybridizes, under specific stringent conditions, to a sequence complementary to a certain base sequence or a base sequence in which u is t in the certain base sequence. The term "gene" does not specify the kind of a functional region, and also encompasses, for example, expression regulatory regions, coding regions, exons, and introns.

In the present invention, the term "transcription product" means RNA synthesized from the DNA sequence of a gene as a template. When RNA polymerase binds to a site called a "promoter" located on an upstream side of the gene, it causes ribonucleotides to bind to the base sequence of the DNA from the 3' end of the DNA so as to be complementary to the DNA. Thus, RNA is synthesized. Such RNA encompasses not only the gene itself but also the complete sequence from the transcription start point to the end of the poly A sequence including various regions such as coding regions, expression regulatory regions, exons, and introns.

In the present invention, the term "microRNA (miRNA)" means RNA that is first transcribed as an RNA precursor having a hairpin-like structure, then cleaved with dsRNA cleavage enzyme having RNase III cleavage activity, and incorporated into a protein complex called RISC, where it is involved in inhibition of mRNA translation. The term "miRNA" as used herein not only means an "miRNA" represented by a specific base sequence (or a specific sequence identification number) but also includes precursors (pre-miRNA, pri-miRNA) of the "miRNA", and thus encompasses "miRNA" encoding miRNA having an equivalent biological function to miRNA encoded by these precursors (e.g., homologs); mutants such as polymorphisms; and derivatives.

In the present invention, the term "probe" is not particularly limited, and means, for example: an Eprobe; a polynucleotide used for specifically detecting an RNA produced by the expression of a gene or a polynucleotide derived from the RNA; and/or a polynucleotide complementary thereto.

The term "primer" is not particularly limited, and means, for example: an Eprimer; a polynucleotide composed of successive nucleotides, which specifically recognizes and amplifies an RNA produced by the expression of a gene or a polynucleotide derived from the RNA; and/or a polynucleotide complementary thereto.

In the present invention, the term "complementary polynucleotide (complementary strand, reverse strand)" refers to a polynucleotide that is in a complementary relationship in terms of nucleotides (on the basis of a base pair relationship such as A:T (U) and G:C) with the full-length sequence or a partial sequence of a polynucleotide having a base sequence defined by a sequence identification number or a base sequence obtained by substituting u with t in this base sequence (for the sake of convenience, the full-length sequence or the partial sequence is referred to as "positive strand" herein). Such a complementary strand may not only be perfectly complementary to the base sequence of a target positive strand, but also may be in a complementary relationship to the extent that it can hybridize to the target positive strand under stringent conditions.

In the present invention, the term "stringent conditions" means conditions under which a probe hybridizes to a target sequence to a detectably greater degree than other sequences (e.g., at least twice greater than the background). The stringent conditions are sequence-dependent, and vary widely depending on the environment in which the hybridization is caused. By controlling the stringency of the hybridization and/or washing conditions, it is possible to identify a target sequence that is 100% complementary to the probe.

In the present invention, the term "mutant" means, in the case of a nucleic acid, a naturally occurring mutant caused by polymorphism, mutation, or the like; a mutant including deletion, substitution, addition, and/or insertion of 1, 2, 3, or more bases, preferably 1 or 2 bases in a base sequence obtained by substituting u with t in the base sequence or in a partial sequence thereof, a mutant including deletion, substitution, addition, and/or insertion of 1 or 2 or more bases, preferably 1 or a few bases in a base sequence of a precursor RNA of miRNA, a base sequence obtained by substituting u with t in the base sequence, or a partial sequence thereof, a mutant showing a sequence identity of at least about 50%, at least about 70%, at least about 80%, at least about 90%, at least about 95%, at least about 97%, at least about 98%, or at least about 99% to each of the above-described base sequences or partial sequences thereof, or a nucleic acid that hybridizes to a polynucleotide or oligonucleotide that includes each of the above-described base sequences or partial sequences thereof under the stringent conditions as defined above.

In the present invention, the "% identity" can be determined using a protein or gene search system such as BLAST or FASTA used commonly, with or without introducing a gap to a sequence of interest.

In the present invention, the term "derivative" encompasses an Eprobe, an Eprimer, and a modified nucleic acid, and examples thereof include, but not limited to: derivatives labeled with a fluorophore or the like; derivatives including a modified nucleotide (for example, a nucleotide including a group such as halogen, alkyl such as methyl, alkoxy such as methoxy, thio, or carboxymethyl; and a nucleotide that has undergone reconstitution of the base, saturation of a double bond(s), deamination, substitution of an oxygen molecule(s) with a sulfur molecule(s), or the like); and PNAs (peptide nucleic acids).

The term "analysis" used in the present invention encompasses, for example, qualitative analysis, quantitative analysis, semi-quantitative analysis, and mutation detection.

In the present invention, the "prediction, determination, detection, or diagnosis (and grammatical variations thereof)" is not particularly limited, and means, for example, prediction, determination, detection, or diagnosis of a substance used directly or indirectly for screening a candidate substance that is useful for the prevention, improvement, or treatment of a cancer or any other disease, for the purposes of diagnosing whether or not a subject has the cancer or any other disease, the degree of the seriousness of the cancer or the disease, whether or not the cancer or the disease has been improved, or the degree of the improvement. Examples of the substance include a nucleotide, an oligonucleotide, and a polynucleotide that specifically recognizes and binds to a gene whose expression level in vivo, especially in a tissue or in blood, varies when a subject suffers from a cancer or any other disease. Owing to the above-described properties, the above-described nucleotide, oligonucleotide, and polynucleotide can be used effectively as a probe for detecting the gene expressed in vivo, in a tissue, or in a cell or as a primer for amplifying the gene expressed in vivo.

In the present invention, the "sample" to be subjected to prediction, determination, detection, or diagnosis is not particularly limited, and may be, for example, any biological sample that exhibits change in gene or in expressed gene accompanying the onset of a cancer or any other disease or the change in physical conditions. Specifically, examples of the sample include: tissues and vessels around the tissues; lymph nodes and organs; organs suspected to have the metastasis of cancer cells; blood, urine, saliva, feces, hair, skin, and sweat; and any other substance that can be collected from a living organism.

[Target Nucleic Acid Analysis Method of the Present Invention]

The target nucleic acid analysis method of the present invention has the following features, for example. It is to be noted, however, that the descriptions regarding these features are merely illustrative and do not limit the present invention by any means.

In light of the above-described problems relevant to the Basin Network and the like, it is required that a target nucleic acid analysis method satisfies the following conditions (1) to (3), for example:
(1) the analysis method should be a technique that can quantitatively measure a plurality of loci at the same time;
(2) the analysis method should achieve high sensitivity so that a very low expression level of RNA such as a transcription factor can measured; and
(3) the analysis method can analyze a target nucleic acid very rapidly and easily so that the analysis method actually can be used in clinical practice.

In recent years, a drug cannot be approved easily without a marker with which a responder and a non-responder to the drug can be discriminated, and this makes practical application of many drugs difficult. As specifically described below, the reactivity of a drug, the prognosis, etc. are controlled by networks. Thus, as a matter of course, predicting clinically useful information by examining only one gene is very difficult and theoretically unreasonable. There is a trend toward utilization of system biology to collect information regarding clinical predictions.

Under these circumstances, there is a demand for a technique that can measure multiple loci in a sample collected from a single individual. Furthermore, in order to achieve measurement and determination in terms of system biology, it is necessary to analyze multiple loci at a time. Besides, in clinical sites, POCT (Point of Care Testing) is expected, and it becomes more and more important that information can be obtained from a patient sample right away in an outpatient department, a hospital ward, an operating room, etc. Thus, a technique that allows the measurement to be carried out easily is expected.

To these ends, a microarray generally is used. In the detection utilizing the microarray, a label such as a fluorescent dye is introduced to RNA (DNA) of a specimen using reverse transcription polymerase (DNA polymerase), and this labeled nucleic acid is caused to hybridize to a chip having a primer or probe immobilized thereon. However, in order to remove the background, an operation of removing the surplus labeled nucleic acid is necessary, which takes a lot of labor and time. Besides, scanning also is necessary. Thus, the detection utilizing the microarray has a problem in that the time required for the whole process is long. In order to analyze a large number of genes at a time, a technique using such a microarray or the like is necessary. However, such a technique has some problems such that: it is necessary to wash and remove the surplus labeled nucleic acid, so that the operation process takes labor and time; required operations are complicated; and the reproducibility of results is not very high.

On the other hand, qRT-PCR and qPCR are used as methods with high sensitivity. However, according to these methods, different primers have to be designed for respective target sequences of genes (loci). Because these primers are reacted separately in different reaction solutions (contained in tubes), RNA or DNA used as a template has to be divided into the number of the reaction solutions and then added to the respective reaction solutions. Therefore, in the case where there is only a very small amount of nucleic acid sample, the number of genes (multiple loci) measurable by these methods is limited as a matter of course.

That is, in the case of qRT-PCR or qPCR, the template has to be shared among as many reaction solutions as target regions (loci) to be measured, and when the template is divided and distributed into the reaction solutions, the occurrence of variation in distributed amount is physically inevitable, which results in measurement errors. Furthermore, because the respective reaction solutions contain different primer sequences and target sequences, the amplification efficiencies in these reaction solutions are not the same. As described above, owing to the errors in the distribution among the reaction solutions, the current qRT-PCR or qPCR cannot accurately measure the errors caused by the amplification factors.

On a microarray, a probe or primer utilizing a base sequence that can target several thousands to several tens of thousands of kinds of genes is immobilized. If a test sample is added to the microarray, the gene contained in the sample binds to the probe or primer. By measuring the amount of this binding by some means, it is possible to know the amount of the gene in the test sample. Genes to which the probe or probe immobilized on the microarray can target can be selected freely.

Also, by providing a cancer lesion site (a sample collected during surgery or endoscopy) of a cancer patient and a normal tissue site of the cancer patient and comparing the gene expression levels in these samples, it is possible to estimate the group of genes that can serve as cancer markers. Furthermore, by comparing the gene expression pattern when a subject is in good physical conditions with the gene expression pattern when the subject is in poor physical conditions in order to know the physical conditions of the subject, the subject can have an opportunity to undergo a test and diagnosis even if the subject is a prospective patient without any subjective symptom of a disease.

The microarray is advantageous in that: it can examine multiple loci; and the measurement of the multiple loci can be carried out in one labeled nucleic acid solution. However, the microarray requires cumbersome operations of amplifying a target nucleic acid and introducing a label to the target nucleic acid, and also, it takes time to cause hybridization of the target nucleic acid to the primer or probe. Besides, the detection sensitivity of the microarray is not so high. In addition, the microarray has narrow spectral coverage and can detect known sequences only. Furthermore, in the mutation detection, the microarray exhibits a low S/N ratio, so that the accuracy of determination is not very high. As described above, the microarray has many problems.

In contrast, multiplex quantitative PCR (qRT-PCR) is advantageous in that: the multiplex qRT-PCR can achieve high sensitivity and broad spectral coverage; the amount of a template gene can be measured in the rise time (Ct) while the amplification is being performed; and information regarding mutation can be obtained by plotting a melting curve. On the contrary, it is necessary to design different primers for each one of target nucleic acids, which requires a complicated process that takes time and labor. Also, in order to provide different reaction systems, the respective loci have to be reacted separately in different tubes. It takes labor to measure and provide as many reaction solutions as loci to be detected. Besides, a nucleic acid (RNA, DNA) to be used as a template and the like have to be divided into the number of reactions to be caused. This poses a problem in that a large amount of the template nucleic acid is necessary.

In order to make up for these disadvantages, employing bridge multiple qRT-PCR brings about considerable merits. Bridge PCR to be performed on a chip does not require different reaction systems, because a primer is immobilized on the chip (regarding the bridge PCR, see JP 10(1998)-505492 A, for example). The reaction can be performed in one liquid phase, so that it is not necessary to cause reactions for the respective loci in separate tubes. In the bridge PCR, cumbersome operations of measuring and providing as many reaction solutions as loci are not necessary. Besides, a nucleic acid (RNA, DNA) to be used as a template and the like need not be divided into the number of reactions, so that the bridge PCR can be carried out using a small amount of template nucleic acid. In particular, a large number of loci can be measured using RNA collected from a single cell, and it is possible to cause a reaction even if the total amount of RNA is not more than 1 µl (in the case of a 1 mm×1 mm chip, 50 nl of RNA probably would work). Depending on the purpose of the bridge PCR, it would be effective to add RNaseH beforehand.

Furthermore, when an exciton primer (Eprimer, see Japanese Patent Nos. 4761086 and 4370385, for example) is applied to the bridge multiple qRT-PCR, it is not necessary to label a target nucleic acid, and a sample to be measured, such as RNA or DNA, can be detected merely by adding the sample onto the chip as it is. The sensitivity of the bridge multiple qRT-PCR is improved as compared with that of the multiple qRT-PCR, and other advantages of the bridge multiple qRT-PCR also are considered to be equal or superior to those of the multiple qRT-PCR. Unlike methods utilizing a liquid phase, according to the bridge multiple qRT-PCR, it is possible to measure a plurality of samples using a single chip or to measure different genes or different regions in a single gene at the same time by providing dyes with different absorption wavelengths. This allows an internal control to be provided in every reaction, so that essential conditions for clinical test kits are satisfied. In particular, a microarray using an exciton probe (Eprobe) is advantageous in that: it is not necessary to fluorescently label a substance to be detected such as, for example, a PCR amplification product; and by washing the microarray after the detection of hybridization and then adding a subsequent specimen, the microarray can be used repeatedly without requiring any special labeling or color-developing reaction. Also in view of today's ecology, a reusable microarray is greatly in demand.

More specifically, by utilizing the present invention, it becomes possible to quantify a large number of specimens using a single array, whereas qRT-PCR requires one tube for one sample. Thus, in the bridge multiple qRT-PCR, it is not necessary to separately perform amplification and labeling steps including cRNA preparation on a microarray, and all the steps can be carried out on the array. Furthermore, clusters formed by the bridge PCR are much smaller than spots on an array. Thus, clusters can be counted digitally when they are present at a low density, and this enables not only the counting of the clusters but also quantification of the clusters based on fluorescence intensity. Moreover, the fluorescence intensity is maintained by the clusters even in a low fluorescence range (because the fluorescence does not become less concentrated by spreading throughout the spot). Thus, it is expected that, as compared with a microarray, a broader dynamic range can be achieved in a trace amount range. In particular, by utilizing an Eprimer, only amplified clusters emit fluorescence, which can be measured easily without requiring any special operation.

In the present invention, at the time of detecting and measuring fluorescence, an amplification process (i.e., cluster formation) using bridge PCR is observed on the basis of fluorescence. Thus, a laser beam source for excitation is not required, and the detection can be achieved with a simple lamp light source. Also, as a fluorescence detection camera, it is not necessary to provide a supersensitive EMCCD camera, and an ordinary CCD camera is sufficient for the measurement. That is, there is an advantage in that the measurement devices to be used can be simplified. In the present invention, because only amplified clusters emit fluorescence, background light can be reduced, so that it is possible to obtain clearer images. Also, it is possible to use a line scanning method in the case where a broader region is to be scanned at a high speed. By using this method, it becomes possible to obtain motion images while moving a stage at a constant speed, and then prepare one still image that shows a broader region. According to this method, the analysis can be achieved no matter how much the number of the kinds of specimens increases (no matter how broad is the measurement region) in principle, although this may be affected by the limit of movement of the stage.

The nucleic acid analysis method of the present invention can be carried out using a DNA chip, for example. Hereinafter, the DNA chip will be described with reference to an illustrative example.

The DNA chip (or microarray) has, for example, at least one or more of the above-described oligonucleotide derivatives immobilized thereon. The immobilization is a concept that encompasses adsorption. This concept also encompasses bonding by covalent bond or the like.

The diameter of each DNA spot on a substrate surface at the time of preparing the DNA chip (or microarray) is not particularly limited, and generally is about 0.5 to about 20000 µm, more preferably about 5 to about 2000 µm, and still more preferably about 50 to about 200 µm. Also, the spot pitch is not particularly limited, and generally is about 1 to about 50000 µm, more preferably about 10 to about 5000 µm, and still more preferably about 100 to about 500 µm.

Examples of a carrier to be used in the DNA chip (or microarray) include, but not limited to: glass such as microporous glass or porous glass; polystyrene; a metal; and a magnetic bead having a ferrite core coated with glycine methacrylate. The carrier may have any shape, such as a shape like a plate (like a substrate) or a shape like a bead.

The DNA chip may be the one utilizing a probe-on-carrier method. The probe-on-carrier method is a method in which a DNA probe is synthesized on a microporous glass (CPG), which is considered to be the most suitable material for DNA synthesis, and then, without separating the probe molecule from the CPG carrier, the DNA probe bound to the CPG is used to detect SNPs. The CPG to be used preferably has a particle diameter from 50 Å to 50000 Å, more preferably from 500 Å to 5,000 Å. By using this probe-on-carrier method, an operation of immobilizing the DNA probe on the substrate can be omitted, thus enhancing the throughput of the DNA chip synthesis. Because the probe-on-carrier method can achieve a very high DNA synthesis reaction efficiency of 99.8% or more, it is possible to provide a DNA probe with high purity, which brings about an advantageous effect in that the accuracy of the DNA chip is improved greatly. Moreover, CPG provided with a necessary DNA probe can be mass-produced, which allows the reduction in cost and better quality control. In most of conventional DNA chips, detection is carried out two-dimensionally on a flat surface of a microscope slide. In contrast, according to the probe-on-carrier method in which CPG is employed, three-dimensional detection and high-density arrangement of DNA probe are possible, so that detection with high sensitivity becomes possible.

When an already-existing DNA synthesis system is applied to the above-described probe-on-carrier method, in the process of removing a protecting group of a nucleobase moiety (an ammonia treatment), a phenomenon may be observed in which the Si—O binding in the linker moiety is cleaved, and about 90% of the DNA probe is detached from the carrier surface.

Immobilization of an oligonucleotide derivative on a surface of a carrier can be achieved by binding the oligonucleotide derivative to the surface via a suitable linker by way of, for example, metal-sulfur binding or the like. Not only one kind of oligonucleotide derivative but also two or more kinds of oligonucleotide derivative may be immobilized on the carrier surface. To the substituent not bound to the carrier, a fluorescent molecule, a quenching molecule, or the like may be bound, so that it can be detected when the carrier is used as a DNA chip or the like.

The DNA chip (or microarray) can be used in a method for identifying a nucleic acid in a sample, etc. The identification method is carried out by, first, hybridizing a sample to the DNA chip (or microarray). The hybridization can be caused by, for example, adding about 0.01 µM to about 1000 µM of the sample to the oligonucleotide derivative immobilized on the DNA chip (or microarray). The conditions for hybridization are about several seconds to about several tens of hours at a temperature of, for example, 0° C. to 100° C., more preferably 20° C. to 90° C., and still more preferably 30° C. to 80° C., although the conditions vary depending on the kind of the polynucleotide derivative. It is to be noted, however, that the conditions for hybridization are not limited to the above-described ranges.

After the completion of the hybridization, the chip is washed 2 to 5 times with a suitable washing solution depending on the kind of the chip. The oligonucleotide derivative can be used in a method for identifying a nucleic acid or gene detection in the above-described manner. Examples of the gene detection technique include, but are not limited to, real-time PCR, in addition to the above described techniques using the DNA chip or microarray.

In the present invention, the term "detect (and grammatical variations thereof)" is not particularly limited, and means, for example, to detect exhaustively the fluorescence signal of a probe or primer amplified in the form of spots on a chip substrate with reference to a fluorescence image. As a detection device, a commonly used fluorescence microscope is necessary. In particular, it is desirable that the fluorescence microscope includes a light source for exciting an Eprobe or an Eprimer, a dichroic mirror, an excitation filter, a fluorescence filter, and a camera for detection. Furthermore, in order to measure the fluorescence intensity of an Eprobe or Eprimer on a time-series basis, it is necessary to scan the same image over and over again with high accuracy and in a broad range, so that a controllable stage with a high positional accuracy is necessary. Examples of the detection camera include those that do not amplify or can amplify a fluorescence signal, and line scan cameras that can obtain images successively over a broad range.

The method for identifying a nucleotide in a target nucleic acid includes the steps of causing hybridization, annealing, or an extension reaction between an oligonucleotide derivative or the like and the target nucleic acid in a sample; and detecting the hybridization product or the amplification product. In the method for identifying a nucleotide in a target nucleic acid according to the present invention, first, an oligonucleotide derivative is hybridized to the target nucleic acid in a sample. The sample to be used is not particularly limited as long as it contains a nucleic acid. Examples of the sample include cell extracts, body fluids such as blood, PCR products, and oligonucleotides. Conditions for hybridizing a primer or a probe are as described above.

Examples of a method for amplifying a biological sample include a bridge PCR method. In the bridge PCR method, the 5' end of a primer used therein is immobilized on a support, and an extension reaction occurs when the primer anneals to a target product. Furthermore, by repeating heat denaturation, annealing, and an extension reaction on a support, an amplification product of a target amplification region in a target biological sample is obtained, if the target amplification region is present. In particular, in the present invention, by immobilizing an Eprimer that includes a sequence specific to a target amplification region on a microarray, only in the case where target amplification occurs, an amplification reaction occurs only at the site where the Eprimer is immobilized, so that the fluorescence signal of the Eprimer can be measured directly.

The "exciton effect" (exciton coupling) is an effect in which, for example, a plurality of dyes aggregate in parallel to form an H-aggregate and thereby hardly exhibit fluorescence emission. Conceivably, this effect is obtained as follows. That is, the excitation state of the dye is split into two energy levels by Davydov splitting, excitation to the higher energy level and then internal conversion into the lower energy level occur, and thereby the emission is thermodynamically forbidden. However, these descriptions do not limit the present invention by any means. The possible occurrence of the exciton effect can be confirmed by the appearance of the absorption band of the dyes that have formed the H-aggregate, in a shorter wavelength as compared to the absorption band of a single dye. Examples of the dyes that exhibit such an effect include thiazole orange and derivatives thereof, oxazole yellow and derivatives thereof, cyanine and derivatives thereof, hemicyanine and derivatives thereof, and methyl red and derivatives thereof, as well as dye groups generally referred to as cyanine dyes and azo dyes. According to the exciton effect, for example, in the case where the fluorescent dye of the present invention binds to a nucleic acid, the fluorescence intensity in a single-stranded state is suppressed and thereby allows a double helix structure to be detected further effectively.

The Eprimer or Eprobe may be, for example, a nucleic acid molecule having a structure described in Japanese Patent No. 4370385, or may be a nucleic acid molecule having a structure to be described below, for example.

In the nucleic acid probe of the present invention, the structure of the nucleic acid molecule may be, for example, a labeled nucleic acid containing at least one of the structures represented by the following formulae (16), (16b), (17), (17b), (18), and (18b). In the present invention, the labeled nucleic acid also encompasses tautomers and stereoisomers of these structures, as well as salts of these structures, tautomers, and stereoisomers. Hereinafter, the structures represented by the following respective formulae and having dye moieties $Z^{11}$ and $Z^{12}$ that exhibit fluorescence each may be referred to as a "labeled structure". The labeled nucleic acid containing the labeled structure may be referred to as a "labeled probe".

In the present invention, the term "target nucleic acid sequence" not only refers to a nucleic acid sequence to be amplified, but also encompasses a sequence complementary thereto.

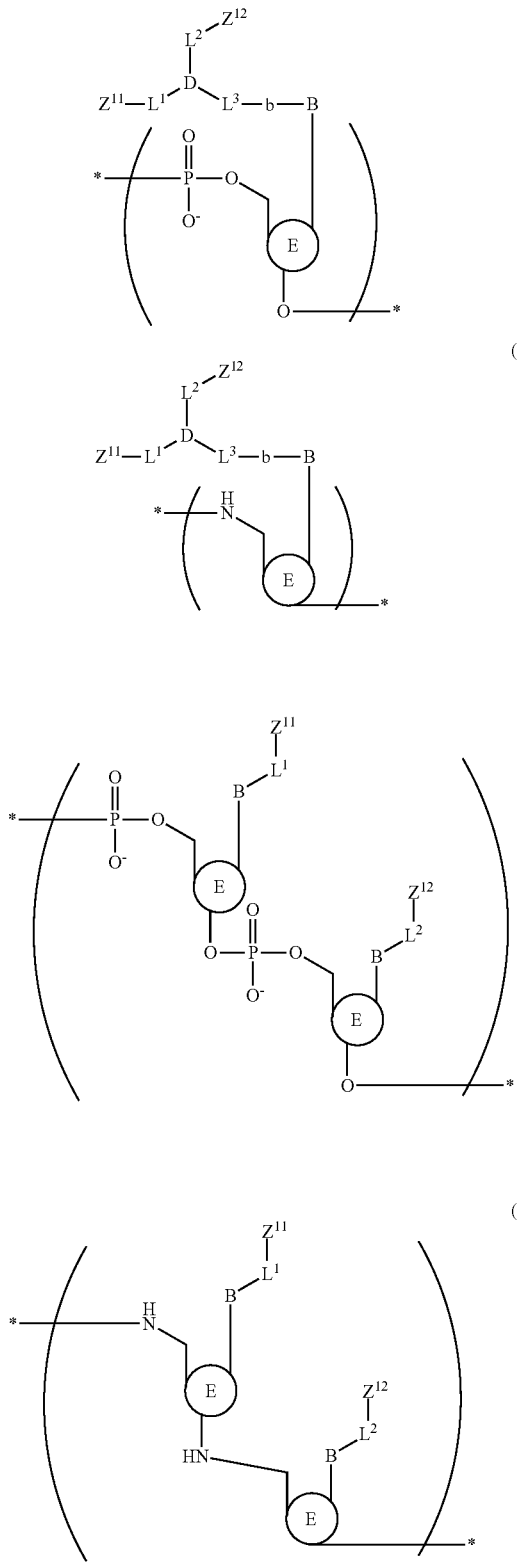

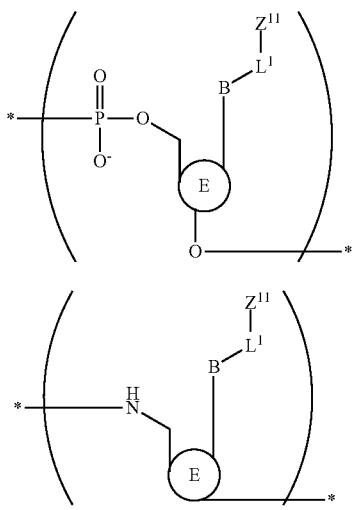

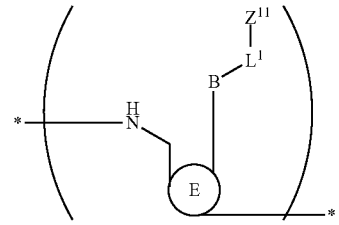

In the formulae (16), (16b), (17), (17b), (18), and (18b),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each an atomic group exhibiting fluorescence, and may be identical to or different from each other, $L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other, D is CR, N, P, P=O, B, or SiR, and R is a hydrogen atom, an alkyl group, or an arbitrary substituent, and b is a single bond, a double bond, or a triple bond, or alternatively, in the formulae (16) and (16b), $L^1$ and $L^2$ are each the linker, $L^3$, D, and b may not be present, and $L^1$ and $L^2$ may be bonded directly to B, provided that:

in the formulae (16), (17), and (18), E is an atomic group described in the item (i), and at least one O atom in a phosphoric acid linkage may be substituted with an S atom;

in the formulae (16b), (17b), and (18b), E is an atomic group described in the item (ii); and in the formulae (17) and (17b), the respective Bs may be identical to or different from each other, and the respective Es may be identical to or different from each other.

In the formulae (16), (17), (16b), (17b), (18), and (18b), the main chain length (the number of main chain atoms) of each of $L^1$, $L^2$, and $L^3$ preferably is an integer of 2 or more. The upper limit thereof is not particularly limited, and is, for example, 100 or less, more preferably 30 or less, and particularly preferably 10 or less.

$Z^{11}$ and $Z^{12}$ are fluorescent dye moieties that exhibit an exciton effect. With this configuration, change in environment around the fluorescent dyes upon binding with a target sequence, e.g., increase in fluorescence when a double helix structure is formed, becomes greater, so that the target sequence can be detected more effectively.

$Z^{11}$ and $Z^{12}$ are not particularly limited as long as they are fluorescent dye moieties that exhibit an exciton effect. More preferably, $Z^{11}$ and $Z^{12}$ are, for example, each independently a group derived from any one of thiazole orange, oxazole yellow, cyanine, hemicyanine, other cyanine dyes, methyl red, azo dyes, and derivatives thereof. Furthermore, a group derived from any other known dye also can be used as appropriate. Many fluorescent dyes that change the fluorescence intensity by binding to nucleic acids such as DNA have been reported. In a typical example, it has been known that ethidium bromide exhibits strong fluorescence by intercalating into a double helix structure of DNA, and it is used frequently for DNA detection. Furthermore, fluorescent dyes whose fluorescence intensity can be controlled according to the microscopic polarity, such as pyrenecarboxyamide and prodan, also are known. The thiazole orange is a fluorescent dye with a benzothiazole ring and quinoline ring linked to each other with a methine group. It usually exhibits weak fluorescence but gives strong fluorescence emission by intercalating into DNA having a double helix structure. Other examples include dyes such as fluorescein, Cy5, and Cy3.

More preferably, $Z^{11}$ and $Z^{12}$ are each independently a dye moiety represented by any one of the following formulae (7) to (9).

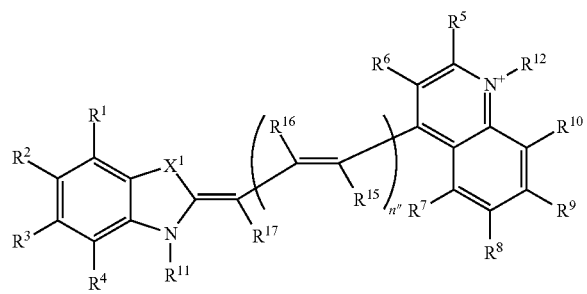

(7)

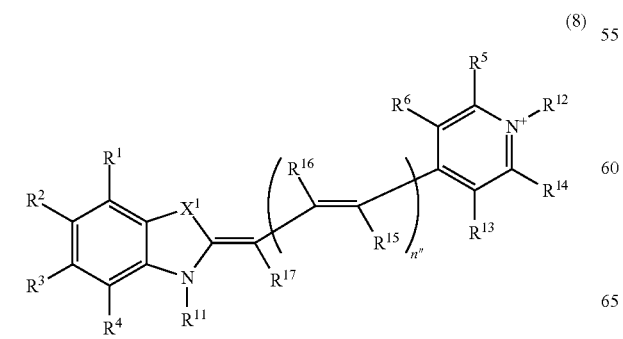

(8)

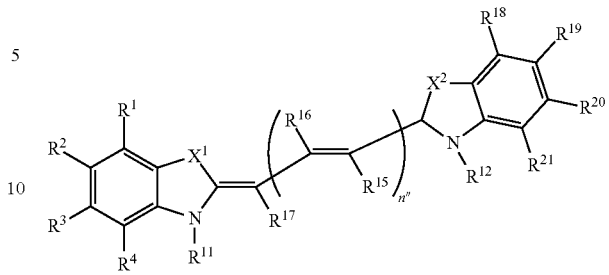

(9)

In the formulae (7) to (9), $X^1$ and $X^2$ are S, Se, or O, n" is 0 or a positive integer, $R^1$ to $R^{10}$ and $R^{13}$ to $R^{21}$ are each independently a hydrogen atom, a halogen atom, a lower alkyl group, a lower alkoxy group, a nitro group, or an amino group, one of $R^{11}$ and $R^{12}$ is a linking group that is bound to $L^1$ or $L^2$ in the formulae (16), (17), (16b), (17b), (18), and (18b), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively.

In the formulae (7) to (9), it is more preferable that, in $R^1$ to $R^{21}$, the lower alkyl group is a linear or branched alkyl group with a carbon number of 1 to 6, and the lower alkoxy group is a linear or branched alkoxy group with a carbon number of 1 to 6.

In the formulae (7) to (9), it is more preferable that in $R^{11}$ and $R^{12}$, the linking group is a polymethylene carbonyl group with a carbon number of at least 2 and is bound to $L^1$ or $L^2$ in the formula in the formula (16), (17), (16b), (17b), (18) or (18b) in the carbonyl group moiety. The upper limit of the carbon number of the polymethylene carbonyl group is not particularly limited, and is, for example, 100 or less, preferably 50 or less more preferably 30 or less, and particularly preferably 10 or less.

When $Z^{11}$ and $Z^{12}$ are each represented by any one of the formulae (7) to (9), it is more preferable that they are, for example, each independently a group represented by formula (19) or (20).

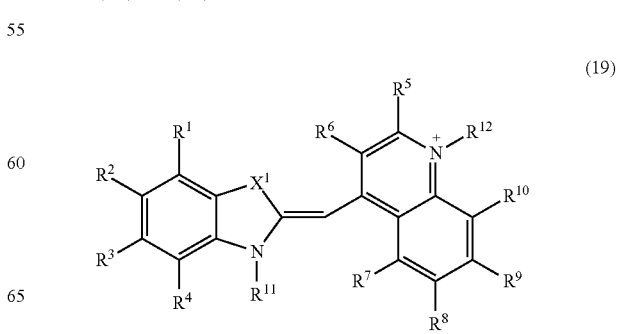

(19)

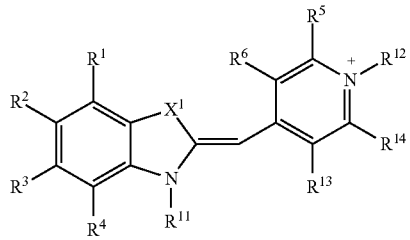
(20)

In the formulae (19) and (20), $X^1$ denotes —S— or —O—. $R^1$ to $R^{10}$ and $R^{13}$ and $R^{14}$ each independently indicates a hydrogen atom, a halogen atom, a lower alkyl group, a lower alkoxy group, a nitro group, or an amino group. One of $R^{11}$ and $R^{12}$ is a linking group that is bound to $L^1$ or $L^2$ in the formulae (16), (17), (16b), (17b), (18), and (18b), and the other is a hydrogen atom or a lower alkyl group.

Particularly preferably, $Z^{11}$ and $Z^{12}$ are each independently a dye moiety represented by any one of the following chemical formulae.

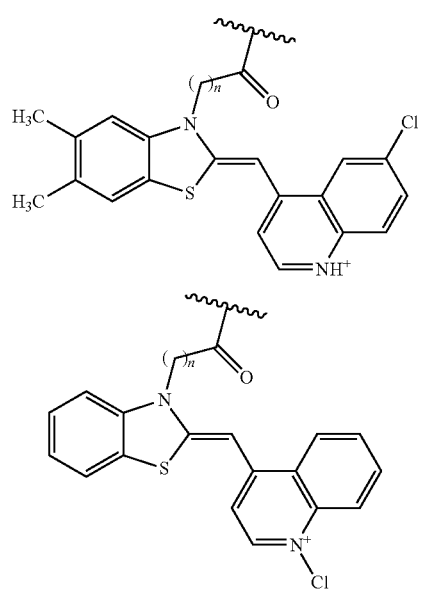

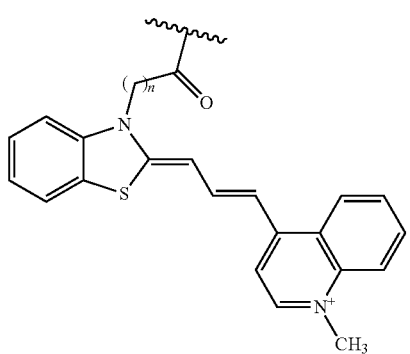

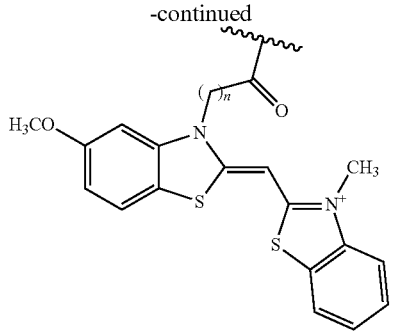

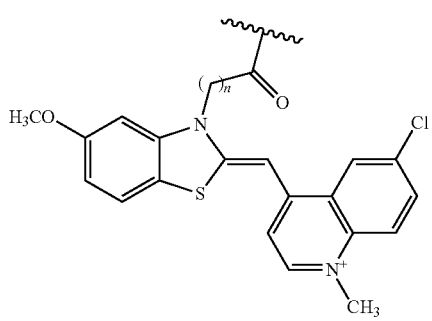

In each of the above chemical formulae, it is particularly preferable that n is a positive integer and in the range from 2 to 6.

In the formulae (16), (17), (16b), (17b), (18), and (18b), B may have a natural nucleobase skeleton, and also, as described above, may have an artificial nucleobase skeleton. For example, B preferably is a structure represented by Py (pyrimidine ring), Py der., Pu (purine ring), or Pu der. The Py is an atomic group having a covalent bond to E in the 1-position and a covalent bond to a linker moiety in the 5-position in a six-membered ring represented by the following formula (11). The Py der. is an atomic group in which at least one of all the atoms of the six-membered ring of the Py has been substituted with an N, C, S, or O atom, and the N, C, S, or O atom optionally may have an electric charge, a hydrogen atom, or a substituent. The Pu is an atomic group having a covalent bond to E in the 9-position and a covalent bond to a linker moiety in the 8-position in a condensed ring represented by the following formula (12). The Pu der. is an atomic group in which at least one of all the atoms of a five-membered ring of the Pu has been substituted with an N, C, S, or O atom, and the N, C, S, or O atom optionally may have an electric charge, a hydrogen atom, or a substituent.

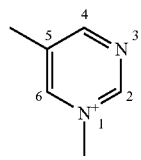
(11)
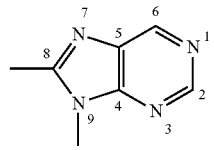
(12)
The nucleic acid molecule in the nucleic acid probe of the present invention may include, for example, at least one of nucleotide structures represented by the following chemical formulae 106, 110, 113, 117, 120, 122, 123, 124, and 114-2, geometric isomers and stereoisomers thereof, and salts thereof.
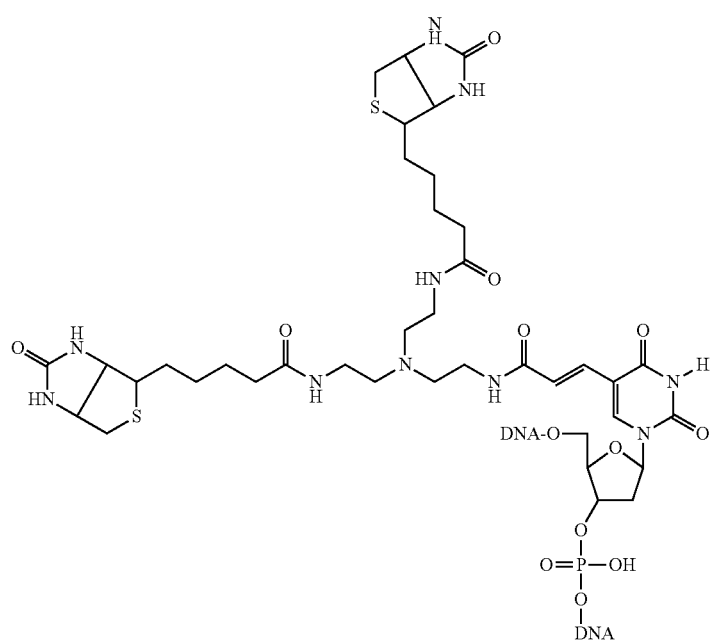
106

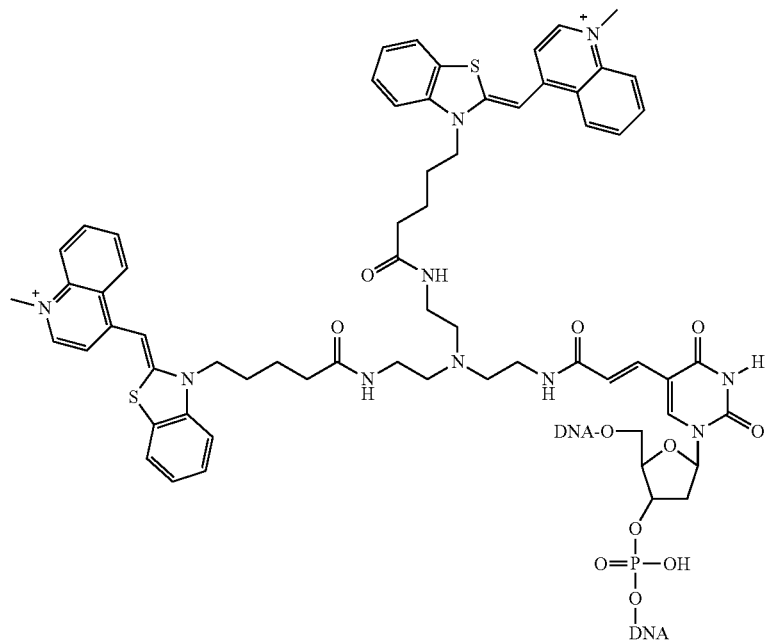
110
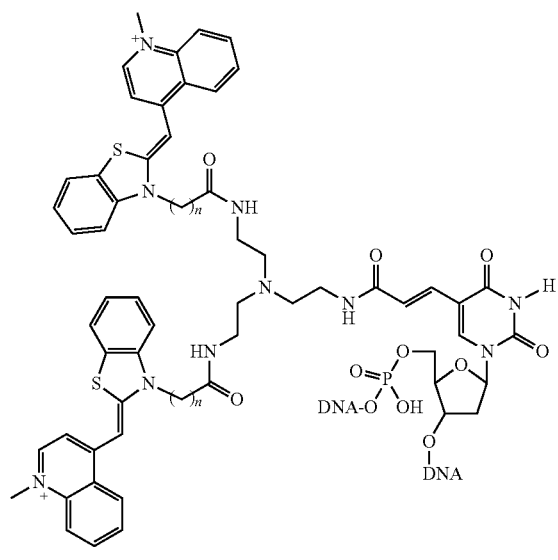
113
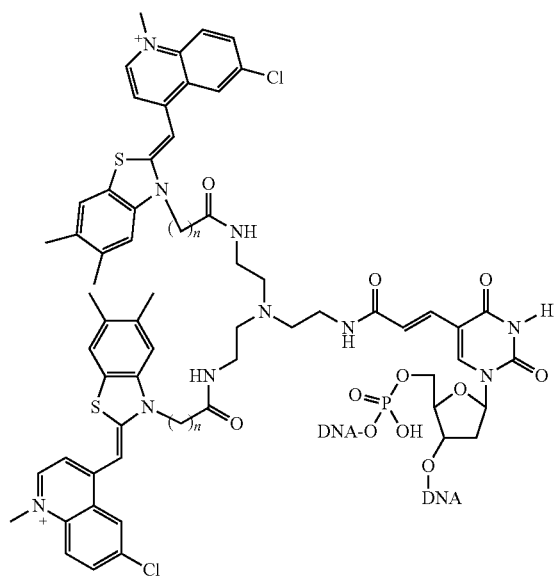
117

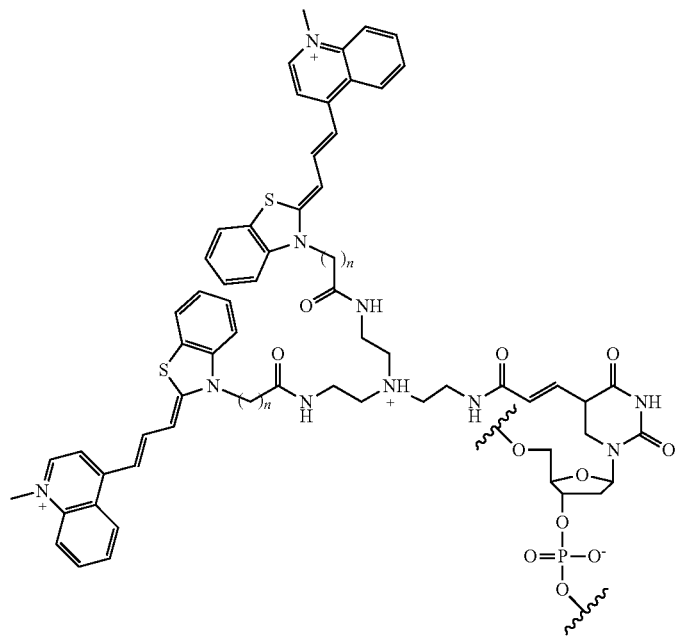
(120)
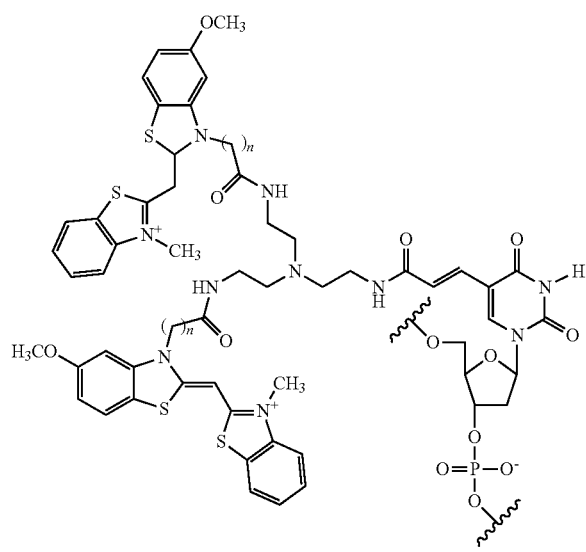
(122)
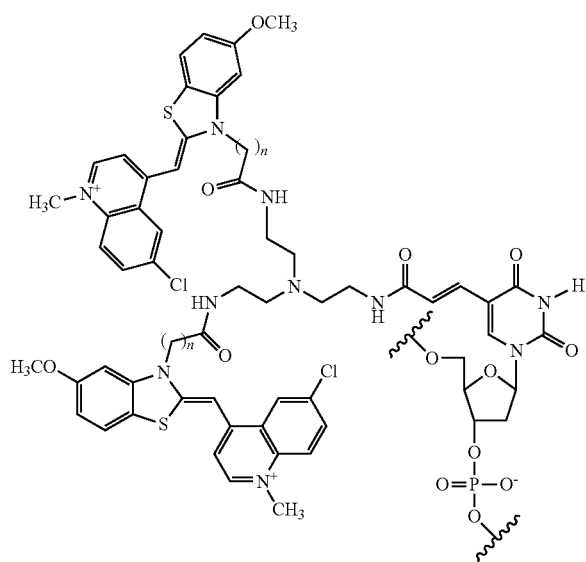
(123)

-continued (124)
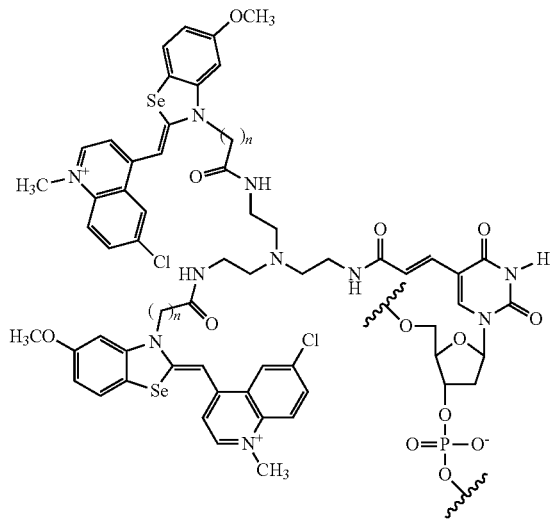

(114-2)
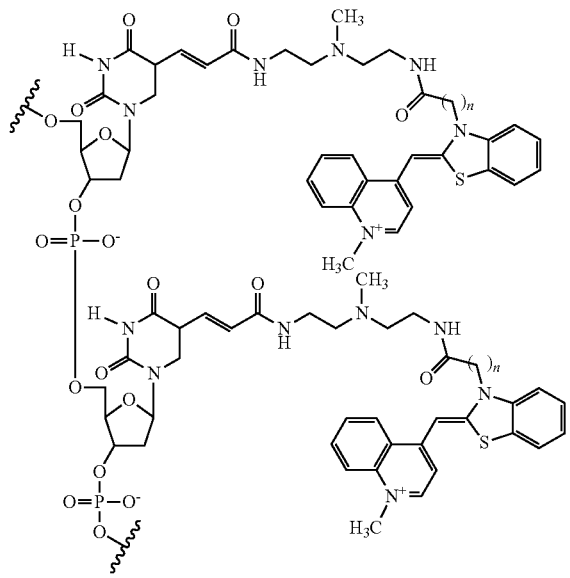

In the chemical formulae 106, 110, 113, 117, 120, 122, 123, 124, and 114-2, the linker length n preferably is a positive integer and in the range from 2 to 6.

The number of the labeled structures included in the nucleic acid probe of the present invention is not particularly limited, and is, for example, about 1 to about 100, preferably about 1 to about 20. In the labeled probe, the site at which the labeled structure is included also is not particularly limited.

In the nucleic acid probe (labeled nucleic acid) of the present invention, the basic skeleton of each nucleic acid is not particularly limited. Examples thereof include oligonucleotides, modified oligonucleotides, oligonucleosides, modified oligonucleosides, polynucleotides, modified polynucleotides, polynucleosides, modified polynucleosides, DNAs, modified DNAs, RNAs, modified RNAs, LNAs, PNAs (peptide nucleic acids), chimeric molecules thereof, and other structures. Furthermore, the basic skeleton of each nucleic acid may be a natural one or an artificially synthesized one. In the case of the nucleic acid probe of the present invention, the nucleic acid is not particularly limited as long as it can provide base pairing, for example. In the case of a nucleic acid sample or a target nucleic acid sequence, the nucleic acid is not particularly limited as long as, for example, it serves as a template for synthesizing a complementary strand. Therefore the nucleic acid may be a nucleotide derivative, a part or the whole of which is formed of a completely artificial structure, for example. Examples of artificial bases that compose the nucleic acid include, but are not limited to, 2-amino-6-(N,N-dimethylamino)purine pyridin-2-one, 5-methylpyridin-2-one, 2-amino-6-(2-thienyl)purine, pyrrole-2-carbaldehyde, 9-Methylimidazo[(4,5)-b]pyridine, 5-iodo-2-oxo(1H)pyridine 2-oxo-(1H)pyridine, 2-amino-6-(2-thiazolyl)purine, and 7-(2-thienyl)-imidazo[4,5-b]pyridine. In the nucleic acid probe of the present invention, the basic skeleton preferably is an oligonucleotide, a polynucleotide, a DNA, or a modified product thereof. In the present invention, the "nucleotide" may be either deoxynucleotide or ribonucleotide, for example, and the "oligonucleotide" and "polynucleotide" each may be composed of either one of deoxynucleotide and ribonucleotide or may contain both of them. In the present invention, the number of bases that compose the nucleic acid is not particularly limited. Generally, the term "nucleic acid" is synonymous with the term "polynucleotide". Generally, the term "oligonucleotide" is used as a term indicating a polynucleotide composed of a particularly small number of bases, among polynucleotides. In general, a polynucleotide of, for example, 2- to 100-mer, more generally about 2- to 50-mer is referred to as "oligonucleotide", but it is not limited by these numerical values. In the present invention, the term "polynucleotide" also should be interpreted to encompass, for example, polynucleotide and oligonucleotide, as well as artificially synthesized nucleic acids such as peptide nucleic acid, morpholine nucleic acid, methylphosphonate nucleic acid, and S-oligonucleic acid.

Generally, the peptide nucleic acid (PNA) has a structure in which a deoxyribose main chain of oligonucleotide has been substituted with a peptide main chain. Examples of the peptide main chain include a repeating unit of N-(2-aminoethyl)glycine bound by an amide bond. Examples of the base to be bounded to the peptide main chain of PNA include, but not limited to: naturally-occurring bases such as thymine, cytosine, adenine, guanine, inosine, uracil, 5-methylcytosine, thiouracil, and 2,6-diaminopurine; and artificial bases such as bromothymine, azaadenine, and azaguanine.

Generally, LNA is a nucleic acid having two cyclic structures in which, in a sugar-phosphoric acid skeleton, an oxygen atom in the 2'-position and a carbon atom in the 4'-position of ribose are bound to each other by methylene crosslinking. When oligonucleotide containing LNA anneals to DNA, the double-stranded conformation is changed, whereby the thermal stability is improved. LNA has a stronger binding affinity to a nucleic acid than common oligonucleotide. Thus, for example, depending on the conditions for designing the oligonucleotide, more reliable and stronger hybridization can be achieved.

The number of bases contained in the Eprimer or Eprobe is not particularly limited, and may be, for example, about 3 to about 100, preferably 6 to 50, and more preferably 6 to 25.

The raw material of the Eprimer or Eprobe is not particularly limited, and may be a compound, a nucleic acid, or a labeling substance to be described below, for example.

The compound is a compound having a structure derived from a mononucleoside or a mononucleotide, and the structure is a compound represented by the following formula (1), (1b), or (1c), a tautomer or stereoisomer thereof, or a salt thereof.

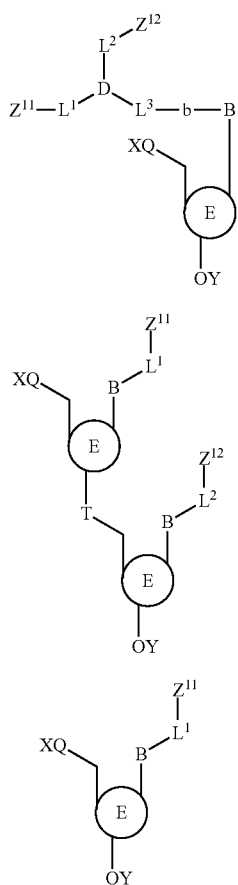

In the formulae (1), (1b) and (1c),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each a hydrogen atom, a protecting group, or an atomic group that exhibits fluorescence, and may be identical to or different from each other, Q is:
O, when E is an atomic group described in the item (i), or
NH, when E is an atomic group described in the item (ii), X is:
a hydrogen atom, a protecting group of a hydroxyl group that can be deprotected with acid, a phosphate group (a monophosphate group), a diphosphate group, or a triphosphate group, when E is an atomic group described in the item (i) or a hydrogen atom or a protecting group of an amino group, when E is an atomic group described in the item (ii), Y is:
a hydrogen atom, a protecting group of a hydroxyl group, or a phosphoramidite group, when E is an atomic group described in the item (i), or
a hydrogen atom or a protecting group, when E is an atomic group described in the item (ii), $L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other, D is CR, N, P, P=O, B, or SiR, and R is a hydrogen atom, an alkyl group, or an arbitrary substituent, b is a single bond, a double bond, or a triple bond,
or alternatively, in the formula (1), $L^1$ and $L^2$ are each a linker, $L^3$, D, and b may not be present, and $L^1$ and $L^2$ may be bonded directly to B, and in the formula (1b), T is:
a phosphoric acid linkage ($PO_4$) in which at least one oxygen atom (O) may be substituted with a sulfur atom (S), when E is an atomic group described in the item (i), or
NH, when E is an atomic group described in the item (ii).

In the formulae (1), (1b) and (1c), E preferably is an atomic group having a main chain structure of, for example, DNA, modified DNA, RNA, modified RNA, LNA, or PNA (peptide nucleic acid).

In the formulae (1) and (1c), preferably, the atomic group represented by:

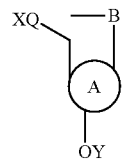

is an atomic group represented by any one of the following formulae (2) to (4),

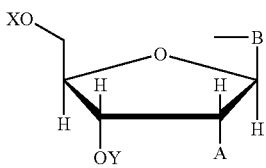

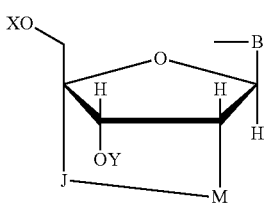

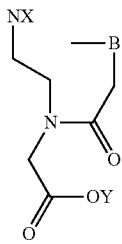
(4)

and in the formula (1b), preferably, an atomic group represented by:

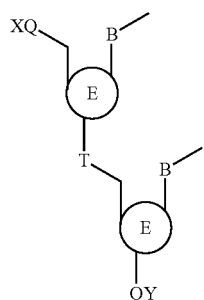

is an atomic group represented by any one of the following formulae (2b) to (4b).

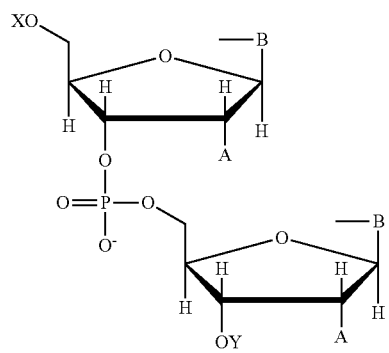
(2b)

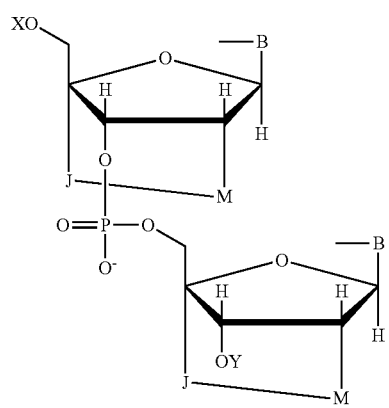
(3b)

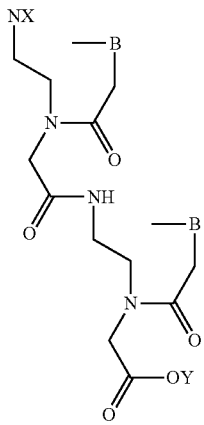
(4b)

In the formulae (2) to (4) and (2b) to (4b),

A is a hydrogen atom, a hydroxyl group, an alkyl group, an alkoxy group, or an electron-withdrawing group, M and J are each $CH_2$, NH, O, or S and may be identical to or different from each other, B, X, and Y are identical to those, respectively, in the formula (1), (1b), or (1c), and in the formulae (2), (3), (2b), and (3b), at least one O atom contained in a phosphoric acid linkage may be substituted with an S atom.

E preferably is an atomic group having a main chain structure of, for example, DNA, modified DNA, RNA, or modified RNA from the viewpoint of easy synthesis, for example. However, E may be an atomic group having a main chain structure of LNA or PNA (peptide nucleic acid).

In the formulae (2) and (2b), it is preferable that, in A, the alkyl group is a methyl group, the alkoxy group is a methoxyl group, and the electron-withdrawing group is halogen, for example.

In the formula (1), (1b), or (1c), it is preferable that the main chain length (the number of main chain atoms) of each of $L^1$, $L^2$, and $L^3$ is an integer of 2 or more. The upper limit of the main chain length (the number of main chain atoms) of each of $L^1$, $L^2$, and $L^3$ is not particularly limited as described above, and is, for example, 100 or less.

Preferably, the compound is a compound represented by the following formula (5), (6), (6b), or (6c), a tautomer or stereoisomer thereof, or a salt thereof.

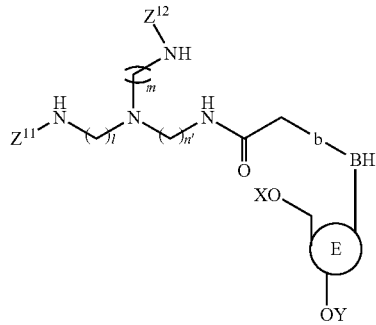
(5)

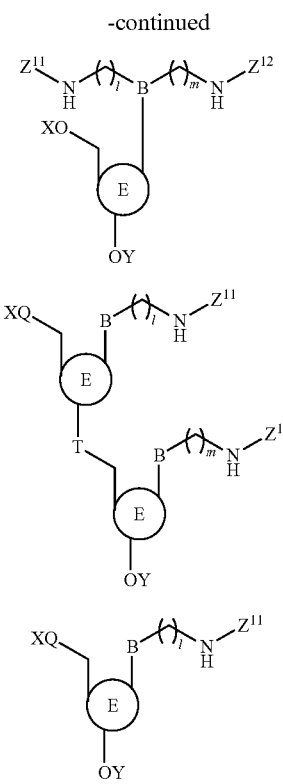

(6)

(7)

(8)

In the formulae (5), (6), (6b) and (6c), l, m and n' are arbitrary, l, m and n' may be identical to or different from each other, l, m and n' each may or may not contain each of C, N, O, S, P, and Si in a main chain thereof, and l, m and n' each may or may not contain each of a single bond, a double bond, a triple bond, an amide bond, an ester bond, a disulfide bond, an imino group, an ether bond, a thioether bond, and a thioester bond in the main chain. B, E, $Z^{11}$, $Z^{12}$, b, X, Y, and T are identical to those in the formulae (1) and (1b), respectively. In the formulae (5), (6), (6b), and (6c), l, m, and n are each preferably an integer of 2 or more. The upper limits of l, m, and n are not particularly limited, and are, for example 100 or less, more preferably 30 or less, and particularly preferably 10 or less.

In the compound, it is preferable that $Z^{11}$ and $Z^{12}$ are dye moieties that exhibit an exciton effect. This allows fluorescence to be increased greatly when, for example, a double helix structure is formed, so that the double helix structure can be detected more effectively. It is to be noted, however, that, in the compound, even when $Z^{11}$ and $Z^{12}$ are not dye moieties that exhibit an exciton effect or even when only one dye moiety (dye) that exhibits fluorescence is introduced into one molecule, it is still possible to detect the double helix structure effectively.

Preferably, $Z^{11}$ and $Z^{12}$ are, for example, dye moieties having fluorescence properties, as described above. The dye moieties having fluorescence properties are not particularly limited. More preferably, $Z^{11}$ and $Z^{12}$ are, for example, each independently a group derived from any one of thiazole orange, oxazole yellow, cyanine, hemicyanine, other cyanine dyes, methyl red, azo dyes, and derivatives thereof. Furthermore, a group derived from any other known dye also can be used as appropriate. Many fluorescent dyes that change the fluorescence intensity by binding to nucleic acids such as DNA have been reported. In a typical example, it has been known that ethidium bromide exhibits strong fluorescence by intercalating into a double helix structure of DNA, and it is used frequently for DNA detection. Furthermore, fluorescent dyes whose fluorescence intensity can be controlled according to the microscopic polarity, such as pyrenecarboxyamide and prodan, also are known. The thiazole orange is a fluorescent dye with a benzothiazole ring and quinoline ring being linked to each other with a methine group. It usually exhibits weak fluorescence but gives strong fluorescence emission by intercalating into DNA having a double helix structure. Other examples include dyes such as fluorescein and Cy3.

More preferably, $Z^{11}$ and $Z^{12}$ are, for example, each independently an atomic group represented by any one of the following formulae (7) to (9).

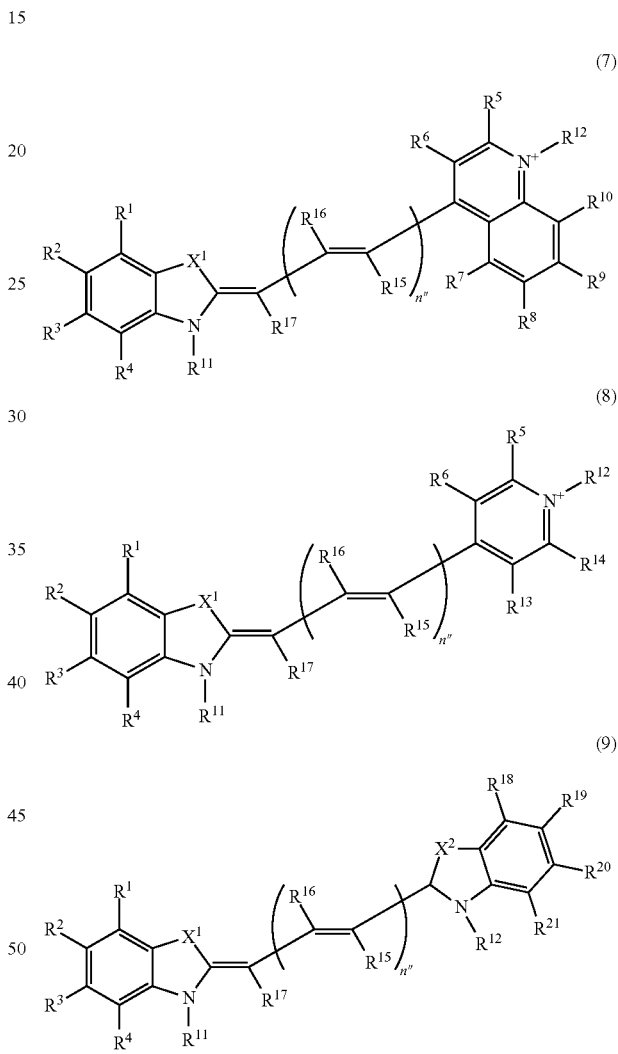

In the formulae (7) to (9),
$X^1$ is S, O, or Se,
n'' is 0 or a positive integer,
$R^1$ to $R^{10}$ and $R^{13}$ to $R^{21}$ are each independently a hydrogen atom, a halogen atom, a lower alkyl group, a lower alkoxy group, a nitro group, or an amino group,
one of $R^{11}$ and $R^{12}$ is a linking group that is bound to $L^1$ or $L^2$ in the formula (1), (1b), or (1c) or NH in the formula (5), (6), (6b), or (6c), and the other is a hydrogen atom or a lower alkyl group,
when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$ and $R^1$ to $R^{21}$ in $Z^{11}$ and $X^1$ and $R^1$ to $R^{21}$ in $Z^{12}$ may be identical to or different from each other, respectively.

In the formulae (7) to (9), it is more preferable that, in $R^1$ to $R^{21}$, the lower alkyl group is a linear or branched alkyl group with a carbon number of 1 to 6, and the lower alkoxy group is a linear or branched alkoxy group with a carbon number of 1 to 6.

In the formulae (7) to (9), it is more preferable that, in $R^{11}$ and $R^{12}$, the linking group is a polymethylene carbonyl group with a carbon number of at least 2 and binds to $L^1$ or $L^2$ in the formula (1), (1b), or (1c) or NH in the formula (5), (6), (6b), or (6c) in the carbonyl group moiety. The upper limit of the carbon number of the polymethylene carbonyl group is not particularly limited, and is, for example, 100 or less.

When $Z^{11}$ and $Z^{12}$ each are represented by any one of the formulae (7) to (9), it is more preferable that they are, for example, each independently a group represented by formula (19) or (20).

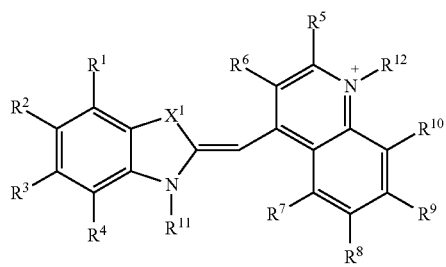
(19)

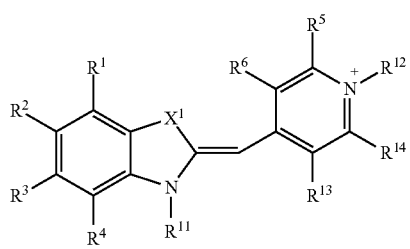
(20)

In the formulae (19) and (20), $X^1$ denotes —S— or —O—. $R^1$ to $R^{10}$ and $R^{13}$ and $R^{14}$ each independently indicates a hydrogen atom, a halogen atom, a lower alkyl group, a lower alkoxy group, a nitro group, or an amino group. One of $R^{11}$ and $R^{12}$ is a linking group that is bound to $L^1$ or $L^2$ in the formula (1), (1b), or (1c) or NH in the formula (5), (6), (6b), or (6c), and the other is a hydrogen atom or a lower alkyl group.

The compound may be, for example, a compound having a structure represented by the following formula (10), a tautomer or stereoisomer thereof, or a salt thereof.

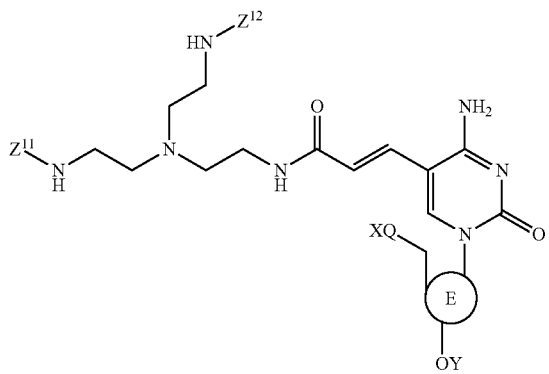
(10)

In the formula (10),

E, $Z^{11}$, $Z^{12}$, Q, X, and Y are identical to those in the formula (1), respectively.

In the formulae (1), (1b), and (1c), B may have a natural nucleobase skeleton, and also, as described above, may have an artificial nucleobase skeleton. For example, B preferably is a structure represented by Py, Py der., Pu, or Pu der. The Py is an atomic group having a covalent bond to E in the 1-position and a covalent bond to a linker moiety in the 5-position in a six-membered ring represented by the following formula (11). The Py der. is an atomic group in which at least one of all the atoms of the six-membered ring of the Py has been substituted with an N, C, S, or O atom, and the N, C, S, or O atom optionally may have an electric charge, a hydrogen atom, or a substituent. The Pu is an atomic group having a covalent bond to E in the 9-position and a covalent bond to a linker moiety in the 8-position in a condensed ring represented by the following formula (12). The Pu der. is an atomic group in which at least one of all the atoms of a five-membered ring of the Pu has been substituted with an N, C, S, or O atom, and the N, C, S, or O atom optionally may have an electric charge, a hydrogen atom, or a substituent.

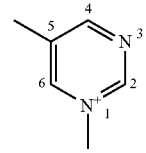
(11)

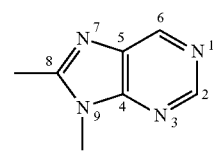
(12)

The compound may be, for example, a compound represented by the following formula (13) or (14), a tautomer or stereoisomer thereof, or a salt thereof.

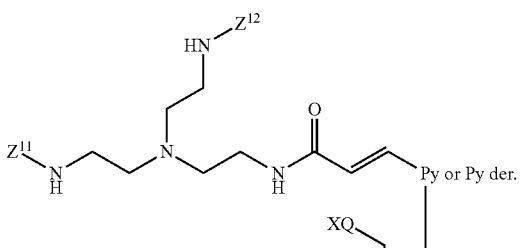

(13)

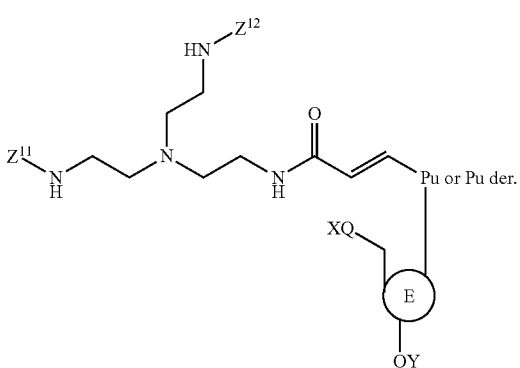

(14)

In the formulae (13) and (14), E, $Z^{11}$, $Z^{12}$, Q, X, and Y are identical to those in the formula (1), respectively, and Py, Py der., Pu, and Pu der. are as defined above.

When the compound has a phosphoramidite group, it is preferable that the phosphoramidite group is represented by, for example, the following formula (15):

(15)

In the formula (15), $R^{22}$ is a protecting group of a phosphate group, and $R^{23}$ and $R^{24}$ are each an alkyl group or an aryl group.

In the formula (15), it is more preferable that $R^{15}$ is a cyanoethyl group and that, in $R^{16}$ and $R^{17}$, the alkyl group is an isopropyl group and the aryl group is a phenyl group.

In the compound, for example, the compound represented by the above formula (1) may be a compound represented by the following formula (21).

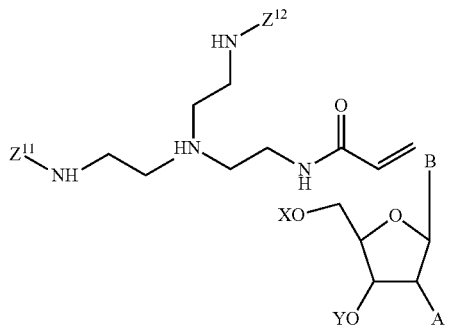

(21)

In the formula (21), A is a hydrogen atom or a hydroxyl group. Preferably, A is a hydrogen atom. B is a residue of adenine, guanine, cytosine, thymine, or uracil. For example, adenine and guanine have been bonded to a double bond in the 8-position, and cytosine, thymine, or uracil has been bonded to a double bond in the 5-position. $Z^{11}$ and $Z^{12}$ are each independently a dye moiety that exhibits fluorescence, a hydrogen atom, or a protecting group of an amino group. Particularly preferably, they are each independently a residue of a thiazole orange derivative or an oxazole yellow derivative. X is a hydrogen atom, a protecting group of a hydroxyl group that can be deprotected with acid, a monophosphate group, a diphosphate group, or a triphosphate group. Y is a hydrogen atom, a protecting group of a hydroxyl group, or a phosphoramidite group.

It is more preferable that the compound represented by the formula (21) is represented by the following formula (22).

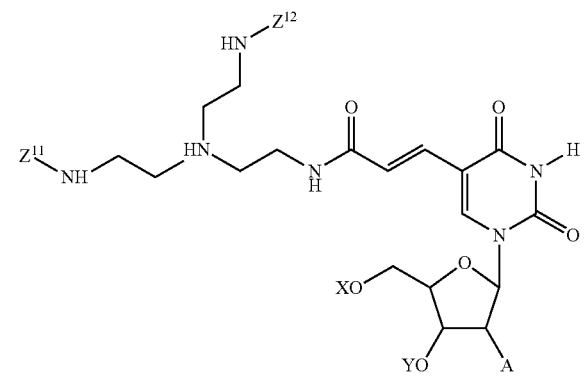

(22)

In the formula (22), A is a hydrogen atom or a hydroxyl group. $Z^{11}$ and $Z^{12}$ are each independently a dye moiety that exhibits fluorescence, a hydrogen atom, or a protecting group of an amino group, and particularly preferably a residue of a thiazole orange derivative or an oxazole yellow derivative. X is a hydrogen atom, a protecting group of a hydroxyl group that can be deprotected with acid, a monophosphate group, a diphosphate group, or a triphosphate group. Y is a hydrogen atom, a protecting group of a hydroxyl group, or a phosphoramidite group.

In the compound of the formula (21) or (22), when $Z^{11}$ and $Z^{12}$ are each a hydrogen atom or a protecting group of an amino group, two amino groups (or protected amino groups) are contained in one molecule. Thus, by utilizing these amino groups, two labeled molecules can be introduced into one molecule. For example, when a labeled nucleic acid is produced with, for example, a fluorescent substance or a chemiluminescent substance being bound thereto, the nucleic acid detection sensitivity can be improved. Furthermore, as in the case where $Z^{11}$ and $Z^{12}$ are each a dye moiety that exhibits fluorescence, labeling a nucleic acid with a specific fluorescent substance makes it possible to detect it easily.

Furthermore, the compound of the formula (21) or (22) in which $Z^{11}$ and $Z^{12}$ are each a dye moiety that exhibits fluorescence is nucleoside or nucleotide modified with two fluorescence molecules, each of which is, for example, a thiazole orange derivative or an oxazole yellow derivative. When a probe composed of a single-stranded nucleic acid containing such a compound is used by itself, it emits very weak fluorescence owing to quenching caused by exciton coupling. However, it emits strong fluorescence when it hybridizes with DNA or RNA. That is, for example, the fluorescence of the thiazole orange derivative or the oxazole yellow derivative is suppressed strongly by the distorted structure thereof, but when the thiazole orange derivative or oxazole yellow derivative binds to DNA, the structural distortion is cancelled and fixed, thus allowing strong fluorescence to be emitted. The fluorescence can be detected by, for example, excitation performed using an Ar laser with a wavelength of 488 nm or 514 nm, but the detection method is not limited thereto.

The compound represented by the formula (1), (1b), or (1c) can be used for synthesizing the Eprimer or Eprobe (labeled nucleic acid), for example. That is, the compound can be used as a labeling substance for nucleic acid (nucleic acid labeling reagent). For example, by using the compound represented by the formula (1), (1b), or (1c) as a nucleotide substrate and carrying out a nucleic acid synthesis reaction using a single-stranded nucleic acid as a template, or by chemically synthesizing a single-stranded nucleic acid (for example, a chemical synthesis method such as a phosphoramidite method that is carried out using an automated nucleic acid synthesizer) using a compound represented by the formula (1), (1b), or (1c), a nucleic acid containing at least one molecule of the compound in one molecule can be produced. In this case, the dye moieties $Z^{11}$ and $Z^{12}$ may be each a dye moiety that exhibits fluorescence but also may be a hydrogen atom or a protecting group. When the dye moieties $Z^{11}$ and $Z^{12}$ are, for example, each a dye moiety that exhibits fluorescence, the labeled probe of the present invention can be produced. When each of the dye moieties $Z^{11}$ and $Z^{12}$ is a hydrogen atom or a protecting group, the labeled probe of the present invention can be produced by further substituting the atom or group with a dye moiety that exhibits fluorescence.

The number of compounds represented by the formula (1), (1b), or (1c) that are included in the Eprimer or Eprobe is not particularly limited. It is, for example, about 1 to about 100, preferably about 1 to about 20.

The compound or nucleic acid (the labeled probe) may have a structure represented by any one of the following formulae (23) to (25), for example. With this configuration, it can be used suitably as a fluorescencEprobe with dyes introduced therein. However, the compound suitable as a fluorescencEprobe is not limited thereto.

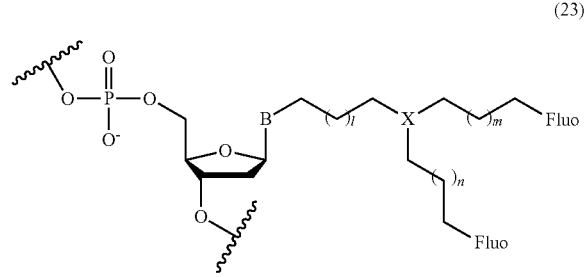

(23)

In the formula (23), two dyes (Fluo) are linked to a base B. The site at which the base B binds to a linker is not particularly limited. For example, the base B is linked to the linker at one position selected from the 4-position, the 5-position, and the 6-position of pyrimidine and the 2-position, the 3-position, the 6-position, the 7-position, and the 8-position of purine. The linker has one base linkage site. The linker branches into at least two along the path, and is linked to the dyes at the ends thereof. The method to be employed for linking it to the base or dye may be not only a bond formed by a metal-catalyzed reaction, a ring formation condensation reaction, a Michael addition reaction, or the like to a double bond or a triple bond, but also an amide bond, an ester bond, a disulfide bond, or a bond formed by an imine formation reaction or the like. With respect to the linker, the lengths (l, m, and n) are arbitrary, and it may contain a single bond, a double bond, a triple bond, an amide bond, an ester bond, a disulfide bond, amine, imine, an ether bond, a thioether bond, a thioester bond, or the like. Furthermore, it is preferable that the linker does not interfere with the exciton effect caused by dimerization. The branched portion (X) is each atom of carbon, silicon, nitrogen, phosphorus, and boron, and protonation (for example, $NH^+$) or oxidation (for instance, $P=O$) may occur. It is preferable that the dye is a dye that exhibits an exciton effect by dimerization, and the site at which the dye is linked to the linker may be any portion thereof. The formula (23) shows deoxyribonucleotide, which is a partial structure of DNA. However, instead of the deoxyribonucleotide, the nucleic acid skeleton may be ribonucleotide (RNA), or also may be a sugar-modified nucleic acid such as 2'-O-methyl RNA or 2'-fluoro DNA, a phosphoric acid modified nucleic acid such as phosphorothioate nucleic acid, or a functional nucleic acid such as PNA or LNA (BNA).

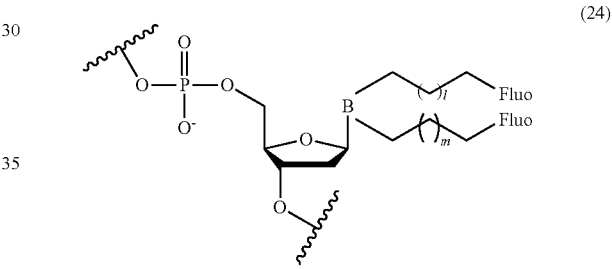

(24)

In the formula (24), two dyes (Fluo) are linked to a base B. The sites at which the base B binds to linkers are not particularly limited. For example, the base B is linked to the linkers at two positions selected from the 4-position, the 5-position, and the 6-position of pyrimidine and the 2-position, the 3-position, the 6-position, the 7-position, and the 8-position of purine. Each of the two linkers has one base linkage site, and is linked to the dye at the other end thereof. The method to be employed for linking it to the base or dye may be not only a bond formed by a metal-catalyzed reaction, a ring formation condensation reaction, a Michael addition reaction, or the like to a double bond or a triple bond, but also an amide bond, an ester bond, a disulfide bond, or a bond formed by an imine formation reaction or the like. With respect to the linkers, the lengths (l and m) are arbitrary, and they may contain a single bond, a double bond, a triple bond, an amide bond, an ester bond, a disulfide bond, amine, imine, an ether bond, a thioether bond, a thioester bond, or the like. Furthermore, it is preferable that the linkers do not interfere with the exciton effect caused by dimerization. It is preferable that the dye is a dye that exhibits an exciton effect by dimerization, and the site at which the dye is linked to the linker may be any portion thereof. The formula (24) shows deoxyribonucleotide, which is a partial structure of DNA. However, instead of the deoxyribonucleotide, the nucleic acid skeleton may be ribonucleotide (RNA), or also may be a sugar-modified nucleic acid such as 2'-O-methyl RNA or 2'-fluoro DNA, a phosphoric acid modified nucleic acid such as phosphorothioate nucleic acid, or a functional nucleic acid such as PNA or LNA (BNA).

(25)

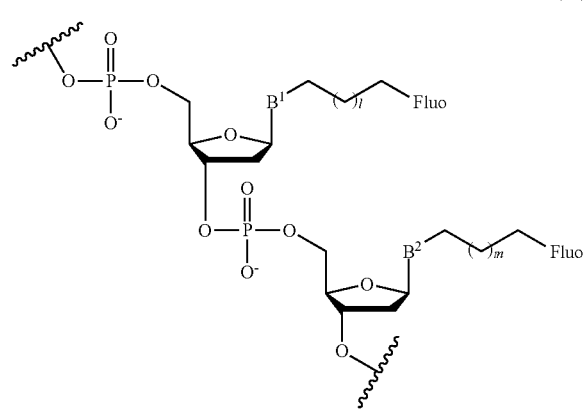

In the formula (25), one dye (Fluo) is linked to each base ($B^1$, $B^2$) of contiguous nucleotides. The site at which each base binds to a linker is not particularly limited. For example, each base is linked to the linker at one position selected from the 4-position, the 5-position, and the 6-position of pyrimidine and the 2-position, the 3-position, the 6-position, the 7-position, and the 8-position of purine. Each of the two linkers has one base linkage site, and is linked to the dye at the other end thereof. The method to be employed for linking them to bases or dyes is not only a bond formed by, for example, a metal-catalyzed reaction, a ring formation condensation reaction, or a Michael addition reaction to a double bond or a triple bond, but also, for example, an amide bond, an ester bond, a disulfide bond, or a bond formed by, for instance, an imine formation reaction. With respect to the linkers, the lengths (l and m) are arbitrary, and they may contain a single bond, a double bond, a triple bond, an amide bond, an ester bond, a disulfide bond, amine, imine, an ether bond, a thioether bond, a thioester bond, or the like. Furthermore, it is preferable that the linkers do not interfere with the exciton effect caused by dimerization. It is preferable that the dye is a dye that exhibits an exciton effect by dimerization, and the site at which the dye is linked to the linker may be any portion thereof. The formula (25) shows deoxyribonucleotide, which is a partial structure of DNA. However, instead of the deoxyribonucleotide, the nucleic acid skeleton may be ribonucleotide (RNA), or also may be a sugar-modified nucleic acid such as 2'-O-methyl RNA or 2'-fluoro DNA, a phosphoric acid modified nucleic acid such as phosphorothioate nucleic acid, or a functional nucleic acid such as PNA or LNA (BNA).

When the compound or nucleic acid (for example, the labeled nucleic acid of the present invention) has an isomer such as a tautomer or a stereoisomer (e.g., a geometric isomer, a conformer, or an optical isomer), any of the isomers can be used for the present invention. The salt of the compound or nucleic acid may be an acid addition salt, and also may be a base addition salt. Furthermore, the acid that forms the acid addition salt may be an inorganic acid or an organic acid, and the base that forms the base addition salt may be an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxide, alkali metal hydroxide, alkaline earth metal hydroxide, carbonate, and hydrogen carbonate. More specific examples thereof include sodium hydroxide, potassium hydroxide, potassium carbonate, sodium carbonate, sodium bicarbonate, potassium hydrogencarbonate, calcium hydroxide, and calcium carbonate. The organic base also is not limited, and examples thereof include ethanolamine, triethylamine, and tris(hydroxymethyl)aminomethane. The method of producing salts thereof also is not particularly limited. They can be produced by a method in which, for example, the acids or bases as described above are added as appropriate to the electron donor/receptor binding molecule by a known method. Furthermore, when the substituent or the like has an isomer, any of the isomers can be used. For instance, in the case of a "naphthyl group", it may be a 1-naphthyl group or a 2-naphthyl group.

Furthermore, in the present invention, the alkyl group is not particularly limited. Examples thereof include a methyl group, an ethyl group, an n-propyl group, an isopropyl group, an n-butyl group, an isobutyl group, a sec-butyl group, and a tert-butyl group. The same applies to groups containing alkyl groups in their structures (for example, an alkylamino group and an alkoxy group). Moreover, the perfluoroalkyl group is not particularly limited. Examples thereof include perfluoroalkyl groups derived from a methyl group, an ethyl group, an n-propyl group, an isopropyl group, an n-butyl group, an isobutyl group, a sec-butyl group, and a tert-butyl group. The same applies to groups containing perfluoroalkyl groups in their structures (for example, a perfluoroalkylsulfonyl group and a perfluoroaryl group). In the present invention, the acyl group is not particularly limited. Examples thereof include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group. The same applies to groups containing acyl groups in their structures (for example, an acyloxy group and an alkanoyloxy group). In the present invention, the number of carbon atoms in the acyl group includes a carbon atom of a carbonyl group. For example, an alkanoyl group (an acyl group) with a carbon number of 1 indicates a formyl group. Furthermore, in the present invention, "halogen" refers to an arbitrary halogen element, and examples thereof include fluorine, chlorine, bromine, and iodine. In the present invention, the protecting group of an amino group is not particularly limited. Examples thereof include a trifluoroacetyl group, a formyl group, a C1-6 alkyl-carbonyl group (for example, acetyl and ethylcarbonyl), a C1-6 alkyl sulfonyl group, a tert-butyloxycarbonyl group (hereinafter also referred to as "Boc"), a benzyloxycarbonyl group, an allyloxycarbonyl group, a fluorenylmethyloxy carbonyl group, an arylcarbonyl group (for example, phenylcarbonyl and naphthylcarbonyl), an arylsulfonyl group (for example, phenylsulfonyl and naphthylsulfonyl), a C1-6 alkyloxycarbonyl group (for example, methoxycarbonyl and ethoxycarbonyl), a C7-10 aralkylcarbonyl group (for example, benzylcarbonyl), a methyl group, and an aralkyl group (for example, benzyl, diphenylmethyl, and trityl group). These groups may be substituted with, for example, one to three halogen atoms (for example, fluorine, chlorine, or bromine) or nitro groups. Specific examples thereof include a p-nitrobenzyloxycarbonyl group, a p-chlorobenzyloxycarbonyl group, an m-chlorobenzyloxycarbonyl group, and a p-methoxybenzyloxycarbonyl group. In the present invention, the protecting group of a hydroxyl group (including one capable of being deprotected with acid) is not particularly limited. Examples thereof include a dimethoxytrityl group, a monomethoxytrityl group, and a pixyl group.

The method for producing the Eprimer or Eprobe is not particularly limited. For example, the Eprimer or Eprobe may be produced with reference to a known synthesis method (production method) as appropriate. Specifically, the Eprimer or Eprobe may be produced with reference to the method disclosed in Japanese Patent No. 4370385, for example.

As one illustrative example, the compound represented by the above formula (21) may be produced by a production method including the steps of reacting tris(2-aminoethyl)amine with a compound represented by the following formula (26) after a carboxyl group of the compound is activated; protecting an amino group: and carrying out a reaction for protecting a hydroxyl group present in the compound obtained above with a protecting group and a reaction for adding phosphoric acid or a phosphoramidite group to the hydroxyl group present in the compound obtained above.

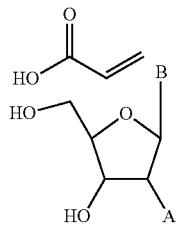

(26)

In the formula (26), A is a hydrogen atom or a hydroxyl group. B is a residue of adenine, guanine, cytosine, thymine, or uracil.

For example, the following production method (synthesis method) can be used for the production of the Eprimer or Eprobe. That is, as an easy DNA labeling method, a method in which an active amino group contained in DNA and an activated carboxyl group in a labeling agent are reacted with each other in a buffer solution has been used widely. This method can be used for the production of both the compound and the nucleic acid of the present invention, and can be used particularly for introduction of a linker or a dye. Examples of the method for introducing an amino group include a method using an amino modifier phosphoramidite commercially available from GLEN RESEARCH.

Each of the dye moieties $Z^{11}$ and $Z^{12}$ can be converted, for example, from a protecting group to a hydrogen atom (i.e., a protecting group is removed), and further the hydrogen atom can be substituted with a dye moiety (dye) having fluorescence properties. The method for removing the protecting group is not particularly limited, and a known method can be used as appropriate. The method for substituting with a dye moiety (dye) having fluorescence properties also is not particularly limited. For example, the compound or nucleic acid of the present invention in which $Z^{11}$ and $Z^{12}$ are each a hydrogen atom may be reacted with a fluorescence molecule (dye) as appropriate. For instance, it is preferable that at least one of $Z^{11}$ and $Z^{12}$ is an active amino group, because it allows the compound or nucleic acid of the present invention to react with a fluorescence molecule (dye) more easily. It is more preferable that both of $Z^{11}$ and $Z^{12}$ are active amino groups. The fluorescence molecule (dye) also is not particularly limited, and may be, for example, a compound represented by any one of the formulae (7) to (9) (where $R^{11}$ and $R^{12}$ are both hydrogen atoms or lower alkyl groups, or carboxypolymethylene groups). Furthermore, in the case of the nucleic acid (polynucleotide, polynucleoside, oligonucleotide, or oligonucleoside), the step of removing the protecting group and the step of substituting with the dye moiety (dye) having fluorescence properties may be carried out either before or after polymerization (nucleic acid synthesis). For example, from the viewpoint of preventing a dye portion from being damaged in the synthesis process, it is preferable that the dye moiety (dye) having fluorescence properties is introduced after polymerization (nucleic acid synthesis).

As described above, the dye is not particularly limited and any dyes can be used. For example, it is preferably a cyanine dye and particularly preferably thiazole orange. The cyanine dye has a chemical structure in which, for example, two heterocycles having hetero atoms are linked to each other with a methine linker. It is possible to synthesize fluorescent dyes with various excitation/emission wavelengths by, for example, changing the kind of the heterocycles or the length of the methine linker, or introducing a substituent into the heterocycles. Furthermore, the introduction of a linker for introducing DNA also is relatively easy. Although thiazole orange hardly emits fluorescence in water, it emits strong fluorescence through an interaction with DNA or RNA. It is considered that, owing to the interaction with the nucleic acid, the interaction between dye molecules is prevented and the rotation around the methine linker located between the two heterocycles of dye molecules is prevented, which leads to an increase in fluorescence intensity. The method of using a thiazole orange dye is well known. It can be used with reference to, for example, H. S. Rye, M. A. Quesada, K. Peck, R. A. Mathies and A. N. Glazer, High-sensitivity two-color detection of double-stranded DNA with a confocal fluorescence gel scanner using ethidium homodimer and thiazole orange, Nucleic Acids Res., 1991, 19, 327-33; and L. G. Lee, C. H. Chen and L. A. Chiu, Thiazole orange: a new dye for reticulocyte analysis, Cytometry, 1986, 7, 508-17.

In the present invention, the basic skeleton of the Eprimer or Eprobe is not particularly limited, as described above. It may be, for example, any of oligonucleotides, modified oligonucleotides, oligonucleosides, modified oligonucleosides, polynucleotides, modified polynucleotides, polynucleosides, modified polynucleosides, DNAs, modified DNAs, RNAs, modified RNAs, LNAs, PNAs (peptide nucleic acids), and other structures. The basic skeleton preferably is DNA, a modified DNA, RNA, or a modified RNA, because the nucleic acid probe can be synthesized easily and also, for example, substitution with a dye (introduction of a dye molecule) can be carried out easily. The method for introducing a dye molecule into LNA or PNA is not particularly limited and a known method can be used as appropriate. Specifically, for example, Analytical Biochemistry 2000, 281, 26-35. Svanvik, N., Westman, G., Wang, D., Kubista, M (2000) Anal Biochem. 281, 26-35. Hrdlicka, P.

J., Babu, B. R., Sorensen, M. D., Harrit, N., Wengel, J. (2005) J. Am. Chem. Soc. 127, 13293-13299 can be referred to.

A method for synthesizing a nucleic acid having, as a basic skeleton, an oligonucleotide, a modified oligonucleotide, an oligonucleoside, a modified oligonucleoside, a polynucleotide, a modified polynucleotide, a polynucleoside, a modified polynucleoside, DNA, a modified DNA, RNA, or a modified RNA is well known. For example, it can be synthesized by a so-called phosphoramidite method. A phosphoramidite reagent to serve as a raw material thereof also can be synthesized easily by a known method. When the nucleic acid of the present invention is DNA, particularly a short oligo-DNA, it can be synthesized easily with an automated DNA synthesizer or the like, for example. Furthermore, it is also possible to synthesize a long-chain nucleic acid (DNA) etc. by, for instance, PCR. As described above, the position where DNA and a dye molecule are bonded to each other is not particularly limited, and particularly preferably is the 5-position of thymidine, for example. Triphosphoric acid of a nucleotide derivative with various substituents being extended from the 5-position of thymidine is known to have a relatively high efficiency of introduction carried out with DNA polymerase. Accordingly, the nucleic acid of the present invention can be synthesized easily, for example, not only when it is a short oligo-DNA but also when it is a long-chain DNA.

Particularly, a fluorescencEprobe (labeled nucleic acid) of the present invention, which is a single-stranded DNA, with, for example, thiazole orange used therein has the following advantages, for example: (1) it can be synthesized easily because it can be prepared merely by introducing, in a buffer solution, a dye into DNA synthesized with an automated DNA synthesizer; and (2) it is also possible to produce a long-chain fluorescencEprobe by reacting a dye with a long-chain DNA prepared enzymatically. Furthermore, it can be excited with light having a relatively long wavelength around, for example, 500 nm.

Next, fluorescent dye moieties of the Eprimer or Eprobe will be described. The fluorescent dye moieties each may be, for example:
(i) the one that emits fluorescence, with two planar chemical structures contained in one molecule, which exist not in the same plane but with a certain angle formed therebetween, being located so as to be arranged in the same plane when the molecule undergoes intercalation into or groove binding to a nucleic acid;
(ii) the one formed of at least two dye molecule groups that do not exhibit fluorescence emission due to the exciton effect obtained when at least two dye molecules aggregate in parallel to each other but exhibit fluorescence emission with the aggregation state being resolved when the molecules undergo intercalation into or groove binding to a target molecule, e.g. a nucleic acid, or
(iii) the one characterized in having a chemical structure of at least two dye molecules contained in one molecule, with the at least two dye molecules not exhibiting fluorescence emission due to the exciton effect obtained when they aggregate in parallel to each other but exhibiting fluorescence emission with the aggregation state being resolved when the molecules undergo intercalation into or groove binding to a target molecule, e.g. a nucleic acid. In the case of (ii) or (iii), it is preferable that the dye molecules are as defined in (i).

In the above formulae, $Z^{11}$ and $Z^{12}$ are dye moieties that exhibit an exciton effect. With this configuration, change in environment around the fluorescent dyes upon binding with a target molecule, e.g., increase in fluorescence when DNA is double-stranded, becomes greater, so that the target molecule can be detected more effectively.

As described above, the dye is not particularly limited and any dyes can be used. For example, it is preferably a cyanine dye and particularly preferably thiazole orange. The cyanine dye has a chemical structure in which, for example, two heterocycles having hetero atoms are linked to each other with a methine linker. It is possible to synthesize fluorescent dyes with various excitation/emission wavelengths by, for example, changing the kind of the heterocycles or the length of the methine linker, or introducing a substituent into the heterocycles. Furthermore, the introduction of a linker for introducing DNA also is relatively easy. Although thiazole orange hardly emits fluorescence in water, it emits strong fluorescence through an interaction with DNA or RNA. It is considered that, owing to the interaction with the nucleic acid, the interaction between dye molecules is prevented and the rotation around the methine linker located between the two heterocycles of dye molecules is prevented, which leads to an increase in fluorescence intensity. The method of using a thiazole orange dye is well known. It can be used with reference to, for example, H. S. Rye, M. A. Quesada, K. Peck, R. A. Mathies and A. N. Glazer, High-sensitivity two-color detection of double-stranded DNA with a confocal fluorescence gel scanner using ethidium homodimer and thiazole orange, Nucleic Acids Res., 1991, 19, 327-33; and L. G. Lee, C. H. Chen and L. A. Chiu, Thiazole orange: a new dye for reticulocyte analysis, Cytometry, 1986, 7, 508-17.

Examples of the present invention will be described below. It is to be noted, however, that the present invention is by no means limited or restricted by the following examples.

EXAMPLES

Nucleic acid molecules were synthesized on the basis of the manners described in the following synthesis examples or in manners equivalent thereto. These synthesis methods (production methods) are the same as those described in the examples of Japanese Patent No. 4370385.

Intermediate Synthesis Examples 1 to 3

According to the following Scheme 1, Compounds 102 and 103 including two active amino groups each protected with a trifluoroacetyl group were synthesized (produced), and further phosphoramidite 104 was synthesized.

Scheme 1

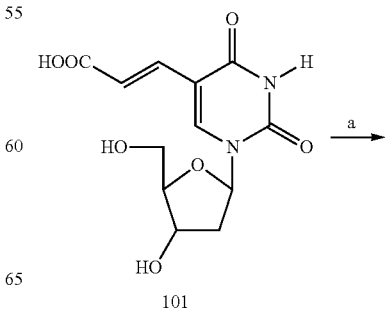

101

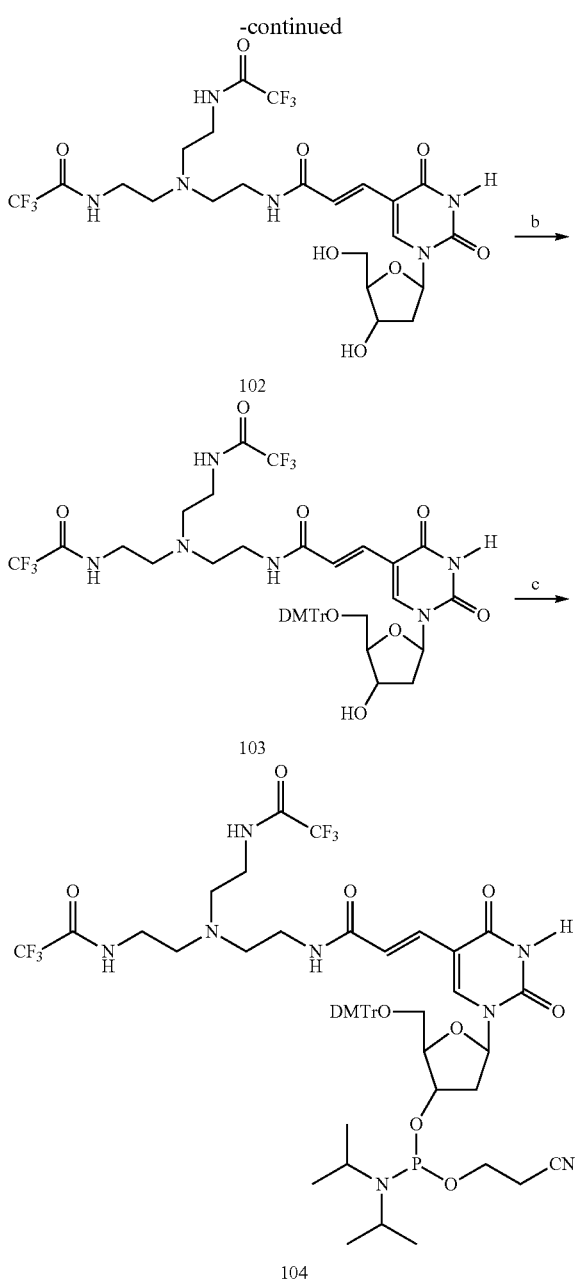

- Reaction reagent and reaction conditions:
(a) (i) N-hydroxysuccinimide, EDC/DMF,
   (ii) tris(2-aminoethyl)-amine/CH₃CN,
   (iii) CF₃COOEt, Et₃N;
(b) DMTrCl/pyridine;
(c) 2-cyanoethyl-N,N,N'-N'-tetraisopropyl phosphoramidite, 1H-tetrazole/CH₃CN.

Scheme 1 will be described below in further detail.

Intermediate Synthesis Example 1: Synthesis of 2-[2-[N,N-bis(2-trifluoroacetamidoethyl)]-aminoethyl]carbamoyl-(E)-vinyl)-2'-deoxyuridine (Compound 102)

The starting material, (E)-5-(2-carboxyvinyl)-2'-deoxyuridine (Compound 101), was synthesized according to Tetrahedron 1987, 43, 20, 4601-4607. That is, first, 71 ml of 1,4-dioxane was added to 430 mg of palladium acetate (II) (FW 224.51) and 1.05 g of triphenylphosphine (FW 262.29), and further 7.1 ml of triethylamine (FW 101.19, d=0.726) was added thereto. This was heated and stirred at 70° C. After the reaction solution changed from reddish brown to blackish brown, 14.2 g of 2'-deoxy-5-iodouridine (FW 354.10) and 7.0 ml of methyl acrylate (FW 86.09, d=0.956) that were suspended in 1,4-dioxane were added thereto. This was heat-refluxed at 125° C. for 1 hour. Thereafter, it was filtered while still hot, the residue was washed with methanol, and then the filtrate was recovered. After the solvent was evaporated from the filtrate under reduced pressure, the product thus obtained was purified with a silica gel column (5-10% methanol/dichloromethane). The solvent of the collected fraction was evaporated under reduced pressure, and the residual white solid was dried under reduced pressure. About 100 ml of ultrapure water was added to the dried solid, and 3.21 g of sodium hydroxide (FW 40.00) was added thereto. This was stirred at 25° C. overnight. Thereafter, concentrated hydrochloric acid was added thereto to acidize the solution. The precipitate thus produced was filtered, washed with ultrapure water, and then dried under reduced pressure. Thus, 8.10 g (yield: 68%) of the desired compound (Compound 101) was obtained in the form of white powder. The white powder was confirmed to be the desired Compound 101 since the ¹HNMR measured value agreed with the reference value. The ¹³CNMR measured value is described below.

(E)-5-(2-carboxy vinyl)-2'-deoxyuridine (Compound 101)

¹³CNMR (DMSO-d6): δ 168.1, 161.8, 149.3, 143.5, 137.5, 117.8, 108.4, 87.6, 84.8, 69.7, 60.8, 40.1.

Next, 1.20 g of (E)-5-(2-carboxy vinyl)-2'-deoxyuridine 101 (with a molecular weight of 298.25), 925 mg of N-hydroxysuccinimide (with a molecular weight of 115.09), and 1.54 g of 1-ethyl-3-(3-dimethylaminopropyl)carbodiimide (with a molecular weight of 191.70) were placed in a recovery flask containing a stirring bar, and 20 ml of DMF was added thereto, which then was stirred at 25° C. for 16 hours. About 1 ml of acetic acid was added thereto and 300 ml of methylene chloride and 100 ml of ultrapure water were added thereto, which then was stirred vigorously. The aqueous layer was removed and further 100 ml of ultrapure water was added, which then was washed twice in the same manner. The precipitate thus produced was filtered, washed with methylene chloride, and then dried under reduced pressure. The solvent was evaporated from the filtrate, methylene chloride was added to the precipitate thus produced, and the precipitate then was recovered in the same manner as described above. The precipitates thus recovered were collected and then suspended in 80 ml of acetonitrile. This was stirred vigorously. Then, 3.0 ml of tris(2-aminoethyl)amine (with a molecular weight of 146.23, d=0.976) was added all at once, which further was stirred at 25° C. for 10 minutes. Thereafter, 4.8 ml of ethyl trifluoroacetate (with a molecular weight of 142.08, d=1.194) was added thereto, and further 5.6 ml of triethylamine (with a molecular weight of 101.19, d=0.726) was added thereto. This was stirred at 25° C. for 3 hours. The solvent was evaporated and the product thus obtained was purified with a silica gel column (5-10% MeOH/CH₂Cl₂). The solvent was evaporated, the product thus obtained was dissolved in a small amount of acetone, and ether then was added thereto. As a result, white precipitate was produced. This was filtered and then washed with ether. Thereafter, this was dried under reduced pressure. Thus, 884 mg (33.5%) of the desired substance (Compound 102) was obtained.

The same synthesis as described above was carried out except for slight changes in the amounts of, for example, raw materials and solvents to be used, the reaction time, and the steps to be taken. As a result, the yield was improved up to 37%. More specifically, 597 mg (2.0 mmol) of (E)-5-(2-carboxy vinyl)-2'-deoxyuridine 101 (with a molecular weight of 298.25), 460 mg (4.0 mmol) of N-hydroxysuccinimide (with a molecular weight of 115.09), and 767 mg (4.0 mmol) of 1-ethyl-3-(3-dimethylaminopropyl)carbodiimide hydrochloride (with a molecular weight of 191.70) were placed in a recovery flask containing a stirring bar. Thereafter, 5.0 ml of DMF was added thereto, which was stirred at 25° C. for 3 hours. About 0.5 ml of acetic acid was added thereto, and 100 ml of methylene chloride and 100 ml of ultrapure water further were added thereto. This was stirred vigorously. The precipitate thus produced was filtered, washed with water, and then dried under reduced pressure overnight. The resultant white residue was suspended in 50 ml of acetonitrile, which was stirred vigorously. Then, 3.0 ml (20 mmol) of tris(2-aminoethyl)amine (with a molecular weight of 146.23, d=0.976) was added thereto all at once, which further was stirred at 25° C. for 10 minutes. Thereafter, 4.8 ml of ethyl trifluoroacetate (with a molecular weight of 142.08, d=1.194) was added and further 5.6 ml (40 mmol) of triethylamine (with a molecular weight of 101.19, d=0.726) was added thereto, which was then stirred at 25° C. for 16 hours. The solvent was evaporated and the product thus obtained was purified with a silica gel column (5-10% MeOH/$CH_2Cl_2$). The solvent was evaporated, the product thus obtained was dissolved in a small amount of acetone, and ether was then added thereto. As a result, white precipitate was produced. This was filtered and then washed with ether. Thereafter, this was dried under reduced pressure. Thus, 453 mg (37%) of the desired substance (Compound 102) was obtained in the form of white powder. The instrumental analytical values of Compound 102 are indicated below.

2-[2-[N,N-bis(2-trifluoroacetamidoethyl)]-aminoethyl]carbamoyl-(E)-vinyl)-2'-deoxyuridine (Compound 102)

$^1$HNMR ($CD_3OD$): δ 8.35 (s, 1H), 7.22 (d, J=15.6 Hz, 1H), 7.04 (d, J=15.6 Hz, 1H), 6.26 (t, J=6.6 Hz, 1H), 4.44-4.41 (m, 1H), 3.96-3.94 (m, 1H), 3.84 (dd, J=12.2, 2.9 Hz, 1H), 3.76 (dd, J=12.2, 3.4 Hz, 1H), 3.37-3.30 (m, 6H), 2.72-2.66 (m, 6H), 2.38-2.23 (m, 2H). $^{13}$CNMR ($CD_3OD$): δ169.3, 163.7, 159.1 (q, J=36.4 Hz), 151.2, 143.8, 134.3, 122.0, 117.5 (q, J=286 Hz), 110.9, 89.1, 87.0, 71.9, 62.5, 54.4, 53.9, 41.7, 38.9, 38.7. HRMS (ESI) calcd for $C_{22}H_{29}F_6N_6O_8$ ([M+H]$^+$) 619.1951, found 619.1943.

Intermediate Synthesis Example 2: Synthesis of 5-O-dimethoxytrityl-(2-[2-[N,N-bis(2-trifluoroacetamidoethyl)]-aminoethyl]carbamoyl-(E)-vinyl)-2'-deoxyuridine (5'-O-DMTr-(2-[2-[N,N-bis(2-trifluoroacetamidoethyl)]-aminoethyl]carbamoyl-(E)-vinyl)-2'-deoxyuridine, Compound 103)

The 5'-hydroxyl group of Compound 102 was protected with a DMTr group. Thus, Compound 103 was obtained. More specifically, first, 618 mg of Compound 102 (with a molecular weight of 618.48) and 373 mg of 4,4'-dimethoxytritylchloride (with a molecular weight of 338.83) were placed in a recovery flask containing a stirring bar. Then, 10 ml of pyridine was added thereto, which was stirred at 25° C. for 16 hours. A small amount of water was added thereto, the solvent was evaporated, and the product thus obtained was purified with a silica gel column (2-4% MeOH, 1% $Et_3N/CH_2Cl_2$). The solvent of the fraction containing the desired compound 103 was evaporated. Thus, 735.2 mg (79.8%) of the desired substance (Compound 103) was obtained. The instrumental analytical values of Compound 103 are indicated below.

5'-O-DMTr-(2-[2-[N,N-bis(2-trifluoroacetamidoethyl)]-aminoethyl]carbamoyl-(E)-vinyl)-2'-deoxyuridine (Compound 103)

$^1$HNMR ($CD_3OD$): δ 7.91 (s, 1H), 7.39-7.11 (m, 9H), 7.02 (d, J=15.6 Hz, 1H), 6.93 (d, J=15.6 Hz, 1H), 6.80-6.78 (m, 4H), 6.17 (t, J=6.6 Hz, 1H), 4.38-4.35 (m, 1H), 4.06-4.04 (m, 1H), 3.68 (s, 6H), 3.32-3.22 (m, 8H), 2.66-2.55 (m, 6H), 2.40 (ddd, J=13.7, 5.9, 2.9 Hz, 1H), 2.33-2.26 (m, 1H). $^{13}$CNMR ($CD_3OD$): δ 168.9, 163.7, 160.1, 159.1 (q, J=36.9 Hz), 151.0, 146.1, 143.0, 137.0, 136.9, 134.1, 131.24, 131.16, 129.2, 128.9, 128.0, 122.5, 117.5 (q, J=286.7 Hz), 114.2, 110.9, 88.1, 87.9, 87.6, 72.6, 65.0, 55.7, 54.2, 53.9, 41.7, 38.9, 38.6. HRMS (ESI) calcd for $C_{43}H_{47}F_6N_6O_{10}$ ([M+H]$^+$) 921.3258, found 921.3265.

Intermediate Synthesis Example 3: Synthesis of 5'-O-dimethoxytrityl-(2-[2-[N,N-bis(2-trifluoroacetamidoethyl)]-aminoethyl]carbamoyl-(E)-vinyl)-2'-deoxyuridine, 3'-[(2-cyanoethyl)-(N,N-diisopropyl)]-phosphoramidite (5'-O-DMTr-(2-[2-[N,N-bis(2-trifluoroacetamidoethyl)]-aminoethyl]carbamoyl-(E)-vinyl)-2'-deoxyuridine, 3'-[(2-cyanoethyl)-(N,N-diisopropyl)]-phosphoramidite, Compound 104)

First, 188 mg (0.20 mmol) of Compound 103 (with a molecular weight of 920.85) was allowed to form an azeotrope with $CH_3CN$, and 28.6 mg (0.40 mmol) of 1H-tetrazole (with a molecular weight of 70.05) was added thereto. This was vacuum-dried with a vacuum pump overnight. Then, 5.1 ml of $CH_3CN$ was added thereto to dissolve the reagent therein, which then was stirred. Thereafter, 194 μl (0.60 mmol) of 2-cyanoethyl-N,N,N',N'-tetraisopropylphosphoramidite (with a molecular weight of 301.41, d=0.949) was added thereto all at once, which was stirred at 25° C. for 2 hours. After that, a mixture of 50 ml of ethyl acetate and 50 ml of saturated sodium bicarbonate water was added thereto, and liquid separation was carried out. The organic layer thus obtained was washed with saturated saline, and then, it was dried with magnesium sulfate. The magnesium sulfate was removed by filtration, and the solvent was then evaporated. The crude product obtained by this liquid separation was allowed to form an azeotrope with $CH_3CN$. Thereafter, assuming that the product (Compound 104) was obtained with a yield of 100%, 0.1 M of $CH_3CN$ solution was prepared and was used for DNA synthesis. The fact that Compound 104 had been obtained was confirmed from $^{31}$PNMR ($CDCl_3$) and HRMS (ESI) of the crude product. The values thereof are indicated below.

Compound 104:

$^{31}$PNMR ($CDCl_3$) δ 149.686, 149.430; HRMS (ESI) calcd for $C_{52}H_{64}F_6N_8O_{11}P$ ([M+H]$^+$) 1121.4336, found 1121.4342.

Intermediate Synthesis Example 4: DNA Oligomer Synthesis

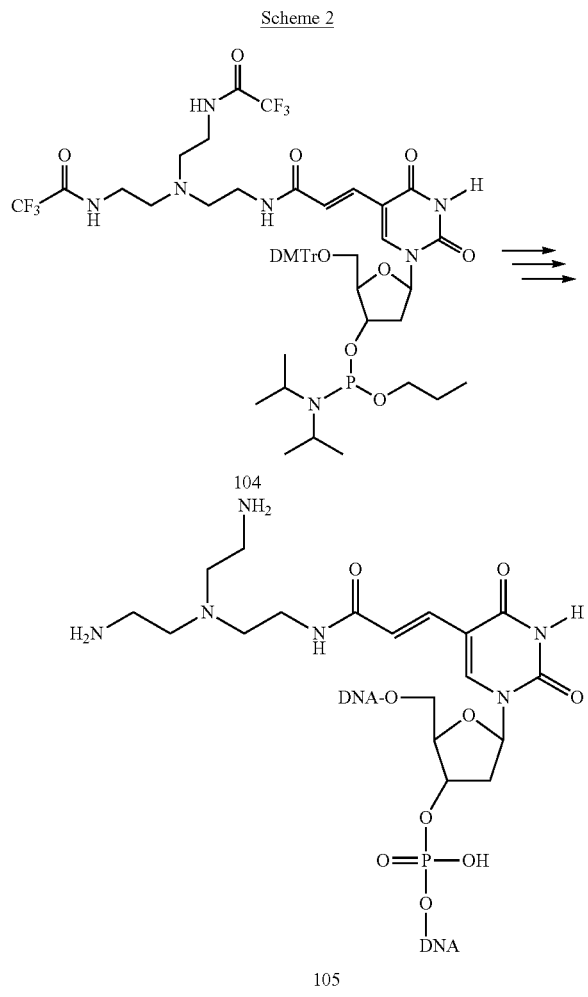

The synthesis of oligo-DNA with an automated DNA synthesizer using Compound 104 was carried out by an ordinary phosphoramidite method (DMTr OFF) on a 1 μmol scale. Thus, each of DNA oligomers with sequences shown in the examples described below was synthesized. Deprotection was carried out with concentrated ammonia water (28 mass %) at 55° C. for 16 hours. Ammonia was volatilized with a speed vac, and the product thus obtained was passed through a 0.45-μm filter. Thereafter, DNA oligomer cut out therefrom was analyzed by reversed-phase HPLC, and the peak that had appeared after about 10.5 minutes was purified (CHEMCOBOND 5-ODS-H (trade name); 10×150 mm, 3 ml/min, 5-30% $CH_3CN$/50 mM TEAA buffer pH 7 (20 minutes), detected at 260 nm). The molecular weight of the product thus purified was measured with a MALDI TOF mass spectrometer in its negative mode. As a result, it was confirmed that the product had a desired sequence.

In order to determine the concentration of each DNA thus synthesized, each purified DNA was digested completely at 25° C. for 16 hours using calf intestinal alkaline phosphatase (50 U/ml), snake venom phosphodiesterase (0.15 U/ml), and P1 nuclease (50 U/ml). The digested liquids thus obtained were analyzed by HPLC with a CHEMCOBOND 5-ODS-H (trade name) column (4.6×150 mm). In this analysis, 0.1 M TEAA (pH 7.0) was used as a developer, and the flow rate was set to 1.0 ml/min. The concentration of the synthesized DNA was determined based on comparison with the peak area of the standard solution containing dA, dC, dG, and dT, the concentration of each of which was 0.1 mM. Furthermore, the synthesized DNA was identified also with a MALDI TOF mass spectrum.

Nucleic Acid Molecule Synthesis Example: Synthesis of Nucleic Acid Molecule Having, in One Molecule, Structures Derived from Thiazole Orange in Two Places

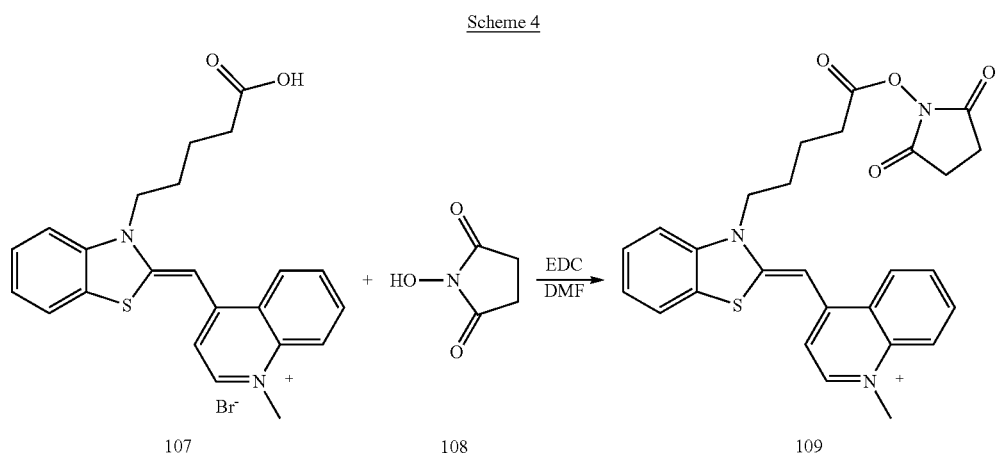

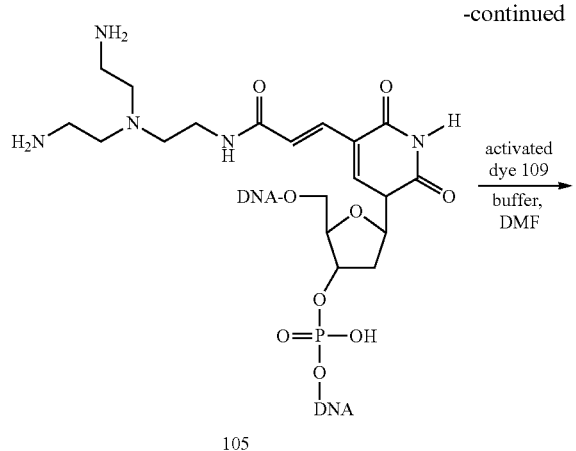
105
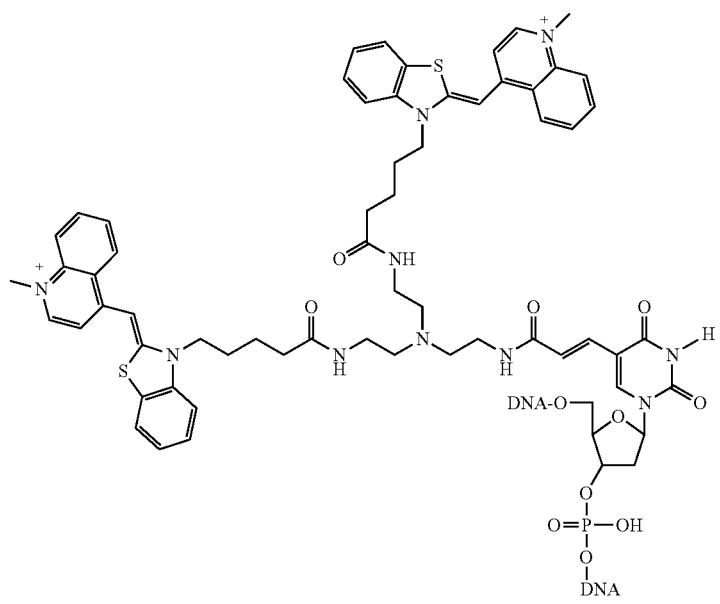
110
As shown in Scheme 4, DNA oligomer (oligonucleotide) 110 was synthesized that has, in one molecule, structures derived from thiazole orange in two places. A more specific description thereof is given below.
The thiazole orange derivative 107 was synthesized as indicated below in Scheme 5 with reference to Organic Letters 2000, 6, 517-519.
Scheme 5
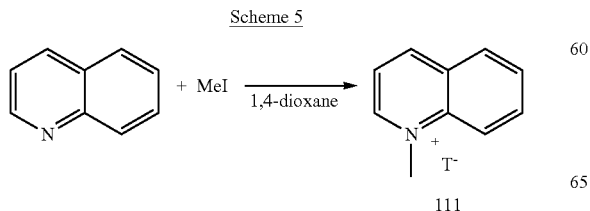
111
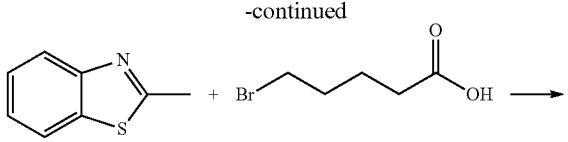
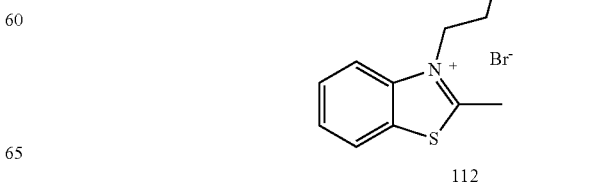
112

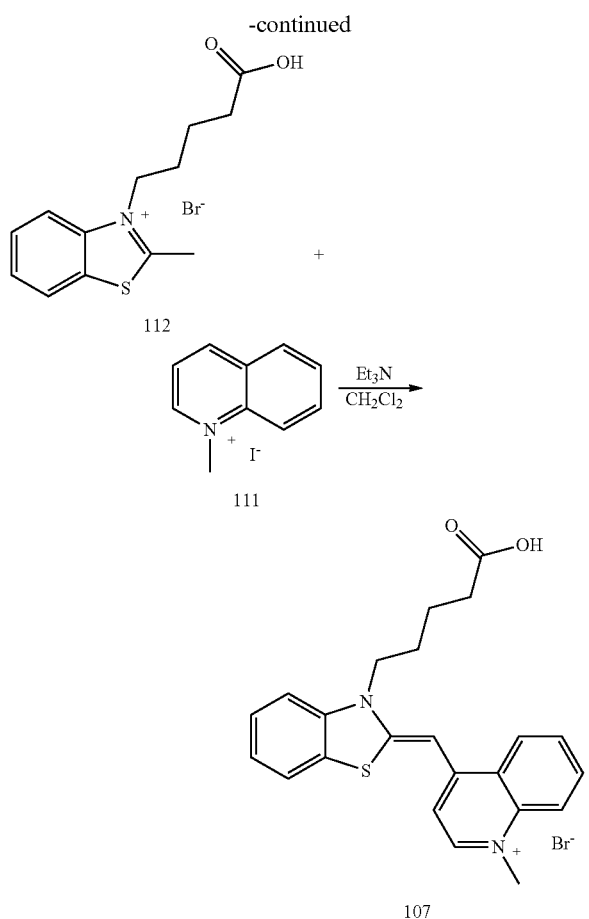

(1) Synthesis of N-methylquinolinium iodide (Compound 111)

First, N-methylquinolinium iodide (Compound 111) was synthesized according to the description in the aforementioned reference. Specifically, 2.4 ml of quinoline and 4 ml of methyl iodide were added to 42 ml of anhydrous dioxane, which was stirred at 150° C. for 1 hour. Thereafter, it was filtered and a precipitate was collected. Then, the precipitate was washed with ether and petroleum ether, and then dried. Thus, N-methylquinolinium iodide (Compound 111) was obtained.

(2) Synthesis of 3-(4-carboxybutyl)-2-methylbenzothiazolium bromide (Compound 112)

8 ml of 2-methylbenzothiazole (FW 149.21, d=1.173) and 9.4 g of 5-bromovaleric acid (5-bromopentanoic acid) (FW 181.03) were stirred at 110° C. for 16 hours. The crude product was cooled to room temperature and a solid thus produced was suspended in 20 ml of methanol, and 40 ml of ether further was added thereto. The precipitate thus produced was filtered and then washed with dioxane until the odor of 2-methylbenzothiazole was removed. This further was washed with ether and then dried under reduced pressure. Thus 9.8 g of white powder was obtained. Thereafter, $^1$HNMR of this white powder was measured. As a result, it was found to be a mixture of 3-(4-carboxybutyl)-2-methylbenzothiazolium bromide (Compound 112), which was the desired substance whose 2-position had been alkylated, and 3-(4-carboxybutyl)-benzothiazolium bromide whose 2-position had not been alkylated. The peak ratio of proton was as follows: non-alkylated: alkylated=10:3. This crude product was used for the next reaction without further being treated.

(3) Synthesis of 1-methyl-4-[{3-(4-carboxybutyl)-2(3H)-benzothiazolylidene}methyl]quinolinium bromide (Compound 107)

2.18 g of the crude product containing 3-(4-carboxybutyl)-2-methylbenzothiazolium bromide (Compound 112) obtained in (2) above and 700 mg of N-methylquinolinium iodide (Compound 111) (FW 271.10) were stirred in 10 ml of methylene chloride at 25° C. for 2 hours in the presence of 3.6 ml of triethylamine (FW 101.19, d=0.726). Thereafter, 50 ml of ether was added thereto and a precipitate produced thereby was filtered, washed with ether, and then dried under reduced pressure. The precipitate was suspended in 50 ml of ultrapure water, which was filtered, washed with ultrapure water, and then dried under reduced pressure. Further, the precipitate was suspended in 50 ml of acetonitrile, which was filtered, washed with acetonitrile, and then dried under reduced pressure. Thus, 307.5 mg of red powder was obtained (yield: 25.3%). This red powder was confirmed to be the desired substance (Compound 107) through a comparison in $^1$HNMR spectrum with the reference value.

Moreover, it was also possible to synthesize 3-(4-carboxybutyl)-2-methylbenzothiazolium bromide (Compound 112) and 1-methyl-4-[{3-(4-carboxybutyl)-2(3H)-benzothiazolylidene}methyl]quinolinium bromide (Compound 107) in the following manner. More specifically, first, 11.7 ml (92 mmol) of 2-methylbenzothiazole (FW 149.21, d=1.173) and 13.7 g (76 mmol) of 5-bromovaleric acid (5-bromopentanoic acid) (FW 181.03) were stirred at 150° C. for 1 hour. The crude product was cooled to room temperature and the solid thus produced was suspended in 50 ml of methanol. Further, 200 ml of ether was added thereto. The precipitate thus produced was filtered, washed with ether, and then dried under reduced pressure. Thus, 19.2 g of light purple powder was obtained. This powder was a mixture of the desired compound 112 (3-(4-carboxybutyl)-2-methylbenzothiazolium bromide) and 2-methylbenzothiazolium bromide. This mixture was subjected to $^1$HNMR (in DMSO-d6) measurement, and the yield of the desired compound 112 was calculated to be 9.82 g (14 mmol, 32%) from the peak area ratio between the peak at 8.5 ppm (derived from the desired compound 112) and the peak at 8.0 ppm (derived from the 2-methylbenzothiazolium bromide). This mixture (crude product) was used for the next reaction without being purified. In the same manner as described above except that the 5-bromovaleric acid (5-bromopentanoic acid) was replaced with 4-bromobutyric acid (4-bromobutanoic acid), 3-(4-carboxypropyl)-2-methylbenzothiazolium bromide with a linker (a polymethylene chain linked to a carboxyl group) having a carbon number n of 3 was synthesized, which was obtained with a yield of 4%. Furthermore, in the same manner as described above except that 5-bromovaleric acid (5-bromopentanoic acid) was replaced with 6-bromohexanoic acid, 3-(4-carboxypentyl)-2-methylbenzothiazolium bromide with a linker (a polymethylene chain linked to a carboxyl group) having a carbon number n of 5 was synthesized, which was obtained with a yield of 35%. Still further, in the same manner as described above except that 5-bromovaleric acid (5-bromopentanoic acid) was replaced with 7-bromoheptanoic acid, 3-(4-carboxypropyl)-2-methylbenzothiazolium bromide with a linker (a polymethylene chain linked to a carboxyl group) having a carbon number n of 6 was synthesized, which was obtained with a yield of 22%.

Next, 1.36 g (5.0 mmol) of N-methylquinolinium iodide (Compound 111) (FW 271.10), 7.0 ml (50 mmol) of triethylamine (FW 101.19, d=0.726), and 100 ml of methylene chloride were added to 3.24 g of the mixture (crude product)

containing Compound 112 (3-(4-carboxybutyl)-2-methyl-benzothiazolium bromide) and 2-methylbenzothiazolium bromide. As a result, a transparent solution was obtained. This solution was stirred at 25° C. for 16 hours. Thereafter, the solvent was evaporated under reduced pressure. Acetone (200 ml) then was added to the residue and the precipitate obtained thereby was filtered, which then was washed with acetone. The residue thus obtained was dried under reduced pressure, and the red residue obtained after drying was washed with distilled water (50 ml). This further was filtered, which was washed with distilled water and then dried under reduced pressure. Thus, the desired substance (Compound 107) was obtained in the form of red powder (654 mg, 1.39 mmol, 28%). This red powder was confirmed to be the desired substance (Compound 107) through a comparison in $^1$HNMR spectrum with the reference value. Peak values from $^1$HNMR and $^{13}$CNMR (DMSO-d6) and the measured values of HRMS (ESI) are indicated below.

Compound 107:

$^1$HNMR (DMSO-d6): δ 8.74 (d, J=8.3 Hz, 1H), 8.51 (d, J=7.3 Hz, 1H), 7.94-7.89 (m, 3H), 7.74-7.70 (m, 1H), 7.65 (d, J=8.3 Hz, 1H), 7.55-7.51 (m, 1H), 7.36-7.32 (m, 1H), 7.21 (d, J=7.3 Hz, 1H), 6.83 (s, 1H), 4.47 (t, J=7.1 Hz, 2H), 4.07 (s, 3H), 2.22 (t, J=6.6 Hz, 1H), 1.77-1.63 (m, 4H); $^{13}$CNMR (DMSO-d6, 60° C.) δ 174.6, 158.8, 148.4, 144.5, 139.5, 137.6, 132.7, 127.9, 126.8, 125.5, 124.1, 123.7, 123.6, 122.4, 117.5, 112.6, 107.6, 87.4, 45.6, 42.0, 35.5, 26.2, 22.3; HRMS (ESI) calcd for $C_{23}H_{23}N_2O_2S$ ([M.Br]$^+$) 391.1480, found 391.1475.

4-((3-(3-carboxypropyl)benzo[d]thiazole-2(3H)-ylidene)methyl)-1-methylquinoliniumbromide with a linker (a polymethylene chain linked to a carboxyl group) having a carbon number n of 3 was synthesized from the mixture of 3-(4-carboxypropyl)-2-methylbenzothiazolium bromide and 2-methylbenzothiazolium bromide by the same method as that used for Compound 107. As a result, this compound was obtained with a yield of 43%. The instrumental analytical values of the compound are indicated below.

4-((3-(3-carboxypropyl)benzo[d]thiazole-2(3H)-ylidene)methyl)-1-methylquinoliniumbromide:

$^1$HNMR (DMSO-d6) δ 8.85 (d, J=8.3 Hz, 1H), 8.59 (d, J=7.3 Hz, 1H), 8.02.7.93 (m, 3H), 7.78.7.70 (m, 2H), 7.61.7.57 (m, 1H), 7.42.7.38 (m, 1H), 7.31 (d, J=6.8 Hz, 1H), 7.04 (s, 1H), 4.47 (t, J=8.1 Hz, 2H), 4.13 (s, 3H), 2.52.2.48 (m, 2H), 1.99.1.92 (m, 2H); $^{13}$CNMR (DMSO-d6, 60° C.) δ 174.3, 158.9, 148.6, 144.5, 139.5, 137.7, 132.7, 127.9, 126.7, 125.6, 124.1, 124.0, 123.7, 122.5, 117.5, 112.5, 107.6, 87.7, 45.6, 42.0, 31.6, 22.4; HRMS (ESI) calcd for $C_{22}H_{21}N_2O_2S$ ([M.Br]$^+$) 377.1324, found 377.1316.

Furthermore, 4-((3-(3-carboxypentyl)benzo[d]thiazole-2(3H)-ylidene)methyl)-1-methylquinoliniumbromide with a linker (a polymethylene chain linked to a carboxyl group) having a carbon number n of 5 was synthesized from the mixture of 3-(4-carboxypentyl)-2-methylbenzothiazolium bromide and 2-methylbenzothiazolium bromide by the same method as that used for Compound 107. As a result, this compound was obtained with a yield of 26%. The instrumental analytical values of the compound are indicated below.

4-((3-(3-carboxypentyl)benzo[d]thiazole-2(3H)-ylidene)methyl)-1-methylquinoliniumbromide:

$^1$HNMR (DMSO-d6) δ 8.70 (d, J=8.3 Hz, 1H), 8.61 (d, J=6.8 Hz, 1H), 8.05.8.00 (m, 3H), 7.80.7.73 (m, 2H), 7.60.7.56 (m, 1H), 7.41.7.35 (m, 2H), 6.89 (s, 1H), 4.59 (t, J=7.3 Hz, 2H), 4.16 (s, 3H), 2.19 (t, J=7.3 Hz, 1H), 1.82.1.75 (m, 2H), 1.62.1.43 (m, 4H); $^{13}$CNMR (DMSO-d6, 60° C.) δ 174.5, 159.0, 148.6, 144.7, 139.7, 137.8, 132.9, 127.9, 126.9, 125.2, 124.2, 123.8, 123.6, 122.6, 117.8, 112.6, 107.7, 87.4, 45.6, 42.1, 36.0, 26.3, 25.9, 24.9; HRMS (ESI) calcd for $C_{24}H_{25}N_2O_2S$ ([M.Br]$^+$) 405.1637, found 405.1632.

Furthermore, 4-((3-(3-carboxyhexyl)benzo[d]thiazole-2(3H)-ylidene)methyl)-1-methylquinoliniumbromide with a linker (a polymethylene chain linked to a carboxyl group) having a carbon number n of 6 was synthesized from the mixture of 3-(4-carboxyhexyl)-2-methylbenzothiazolium bromide and 2-methylbenzothiazolium bromide by the same method as that used for Compound 107. As a result, this compound was obtained with a yield of 22%. The instrumental analytical values of the compound are indicated below.

4-((3-(3-carboxyhexyl)benzo[d]thiazole-2(3H)-ylidene)methyl)-1-methylquinoliniumbromide;

$^1$HNMR (DMSO-d6) δ 8.72 (d, J=8.3 Hz, 1H), 8.62 (d, J=6.8 Hz, 1H), 8.07.8.01 (m, 3H), 7.81.7.75 (m, 2H), 7.62.7.58 (m, 1H), 7.42.7.38 (m, 2H), 6.92 (s, 1H), 4.61 (t, J=7.3 Hz, 2H), 4.17 (s, 3H), 2.18 (t, J=7.3 Hz, 1H), 1.82.1.75 (m, 2H), 1.51.1.32 (m, 6H); $^{13}$CNMR (DMSO-d6, 60° C.) δ 174.0, 159.1, 148.6, 144.7, 139.8, 137.8, 132.9, 127.9, 126.8, 125.0, 124.2, 123.8, 123.6, 122.6, 118.0, 112.7, 107.8, 87.4, 45.5, 42.1, 33.4, 27.9, 26.4, 25.5, 24.1; HRMS (ESI) calcd for $C_{25}H_{27}N_2O_2S$ ([M.Br]$^+$) 419.1793, found 419.1788.

(4) Synthesis of N-hydroxysuccinimidyl ester 109

9.4 mg (20 μmol) of 1-methyl-4-[{3-(4-carboxybutyl)-2(3H)-benzothiazolylidene}methyl]quinolinium bromide (Compound 107) (FW 471.41), 4.6 mg (40 μmol) of N-hydroxysuccinimide (Compound 108) (FW 115.09), and 7.6 mg (40 μmol) of EDC (1-ethyl-3-(3-dimethylaminopropyl)carbodiimide hydrochloride) (FW 191.70) were stirred in 1 ml of DMF at 25° C. for 16 hours. Thus, N-hydroxysuccinimidyl ester (Compound 109) was obtained, in which the carboxy group of the dye (Compound 107) had been activated. This reaction product was not purified, and the reaction solution (20 mM of a dye) was used for the reaction with oligomeric DNA (oligonucleotide) 105 without further being treated.

Furthermore, 4-((3-(4-(succinimidyloxy)-4-oxobutyl)benzo[d]thiazole-2(3H)-ylidene)methyl)-1-methylquinolinium bromide with a linker (a polymethylene chain) having a carbon number n of 3 was synthesized by the same method as that used for Compound 109 except that a compound with a linker (a polymethylene chain) having a different carbon number was used as a raw material instead of Compound 107. Moreover, 4-((3-(4-(succinimidyloxy)-4-oxohexyl)benzo[d]thiazole-2(3H)-ylidene)methyl)-1-methylquinolinium bromide with a linker (a polymethylene chain) having a carbon number n of 5 and 4-((3-(4-(succinimidyloxy)-4-oxoheptyl)benzo[d]thiazole-2(3H)-ylidene)methyl)-1-methylquinolinium bromide with a linker (a polymethylene chain) having a carbon number n of 6 were synthesized in the same manner.

(5) Synthesis of DNA Oligomer (Oligonucleotide) 110 Modified with Two Molecules of Thiazole Orange A DNA oligomer (oligonucleotide) 105 having two active amino groups was synthesized by an ordinary method with the use of an automated DNA synthesizer in the same manner as in Intermediate Synthesis Example 4. Next, this DNA oligomer (oligonucleotide) 105 was reacted with N-hydroxysuccinimidyl ester (Compound 109), thus synthesizing DNA oligomer (oligonucleotide) 110, which was a nucleic acid molecule having, in one molecule, structures derived from thiazole orange in two places. More specifically, first, 30 μl of the DNA oligomer 105 (with a strand concentration of 320 µM), 10 µl of Na$_2$CO$_3$/NaHCO$_3$ buffer (1 M, pH 9.0), and 60 µl of H$_2$O were mixed together. Thereafter, 100 µl of DMF solution (20 mM) of N-hydroxysuccinimidyl ester (Compound 109) was added thereto and mixed well. This was allowed to stand still at 25° C. for 16 hours. Thereafter, 800 µl of H$_2$O was added thereto. The resultant mixture then was passed through a 0.45-µm filter and subjected to purification by reversed-phase HPLC (CHEMCOBOND 5-ODS-H 10×150 mm, 3 ml/min, 5-30% CH$_3$CN/50 mM TEAA buffer (20 minutes), detected at 260 nm).

Example 1

Experiment in which Beta-Actin Messenger RNA Molecules Obtained by Bridge RT-PCR Using an Immobilized Specific Primer Set were Counted 1. Primers of the present example were synthesized by biotinylating the 5' ends of specific primers represented by the following SEQ ID NOs: 1 and 2.

```
Forward:
                                      (SEQ ID NO: 1)
5'-AAA AAA AAA AGG CAT GGG TCA GAA GGA TT-3'

Reverse:
                                      (SEQ ID NO: 2)
5'-AAA AAA AAA AAG GTG TGG TGC CAG ATT TTC-3'
```

2. An adhesive frame (TAKARA BIO INC.) was attached to a biotin-coated surface of a biotin-coated microscope slide (Alliance Technology) to provide a reaction chamber. A 20 µg/ml avidin protein solution prepared using physiological saline containing glycerol was added to the chamber so that the biotin-coated surface of the microscope slide in the chamber was entirely coated with the solution. In order to prevent the surface from being dried, the chamber was covered with the lid of a petri dish. The chamber was then allowed to stand at 37° C. for 30 minutes, thereby immobilizing the avidin protein on the surface of the microscope slide. After the immobilization, the microscope slide was washed three times with physiological saline, thus removing the surplus avidin protein.

3. Glycerol was added to physiological saline so that the concentration thereof became 10%, and the biotinylated primers were added thereto so that the concentration of each of the primers became 3.3 µmol. At this time, not only the solution containing the primer pair but also a solution containing only the forward primer was prepared. To the reaction chamber on the avidin immobilized microscope slide, the primer pair solution or the forward primer solution was added so that the surface of the microscope slide in the chamber was entirely coated with the solution. In order to prevent the surface from being dried, the chamber was covered with the lid of a petri dish. The chamber then was allowed to stand at 37° C. for 30 minutes, thereby immobilizing the biotinylated primer(s). After the immobilization, the microscope slide was washed three times with physiological saline, thus removing the surplus primer(s).

4. 1.6 mM magnesium sulfate, 0.2 mM dNTP, SYBR Green solution, 200 units of SuperScript III, and 2 units of Platinum Taq were mixed with a buffer solution for Platinum Taq. Thus, a reaction solution that allows both reverse transcription and PCR to be carried out therein was prepared. To this reaction solution, beta-actin messenger RNA was added so that the concentration thereof became 100 pM. To the chamber on the microscope slide having the primer pair or only the forward primer immobilized thereon, 25 µl of the reaction solution was added, and the chamber was closed with a cover film (TAKARA BIO INC.).

5. Each microscope slide was placed in a reaction chamber of a GenePro Thermal Cycler (Bioer Technology Co., Ltd.) equipped with a GenePro Insitu "Japanese Version" B-4 block. The microscope slide was heated at 55° C. for 30 minutes and 94° C. for 4 minutes, and then was subjected to 40 cycles of the following thermal treatment: 94° C. for 1 minute, 60° C. for 1 minute, and 68° C. for 1 minute. Thereafter, the microscope slide was incubated at 68° C. for 5 minutes to terminate the reaction.

6. The microscope slide after the termination of the reaction was excited at an excitation wavelength of 470 nm using a fluorescence microscope, and the fluorescence at 525 nm was observed.

Figure 2:
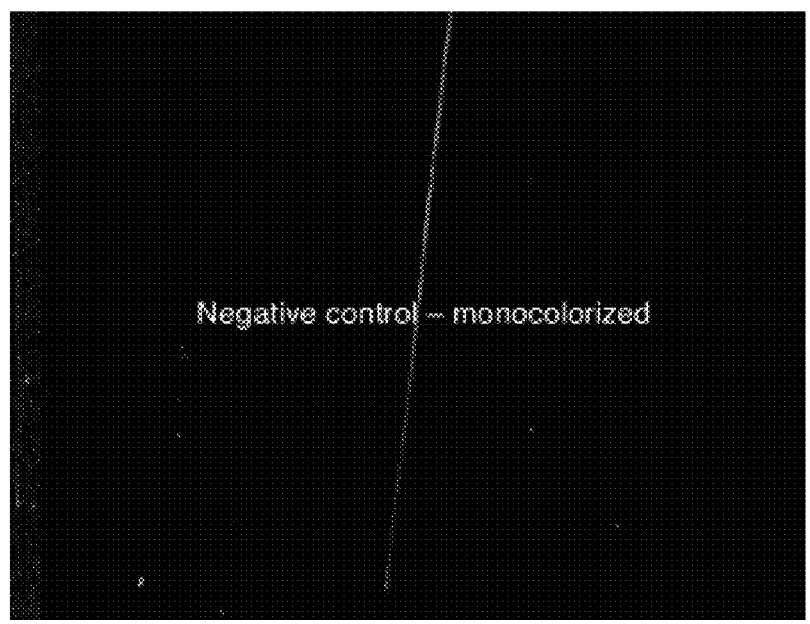
FIG. 2 is a photograph showing that the production of an amplification product of the target nucleic acid was not observed when only a forward primer was used in Example 1.

7. As a result, in the case where the primer pair was used, fluorescence of a large number of clusters was observed, which demonstrates that an amplification product of the target nucleic acid had been produced (FIG. 1). In contrast, in the case where only the forward primer was used, such fluorescence was not observed (FIG. 2).

Example 2

Example 2-A: Designing of Primers and Checking of their Qualities

For the human beta-actin messenger gene sequence (NCBI reference sequence: NM_001101.3), the following primer oligos were designed. The term "primer oligo (which may be referred to simply as "oligo" hereinafter)" refers to an oligonucleotide serving as a primer. The same applies hereinafter.

TABLE 1

| Name of primer oligo | Sequence (5' → 3') | Intended Use |
|---|---|---|
| ACTB-T7RNAF | <u>CTAATACGACTCACTATAGGGAGA</u>ATGGATGATGATATCGCCGCGCT | For RNA synthesis |
| ACTB-RNAR | CATTTTTAAGGTGTGCACTTTTATTCAACTGGTC | For RNA synthesis |
| ACTB-5'F | GGCATGGGTCAGAAGGATT | For PCR |
| ACTB-5'R | AGGTGTGGTGCCAGATTTTC | For PCR |
| ACTB-5'F_5'Bio | [Bio-ON] GGCATGGGTCAGAAGGATT | To be bound to microscope slide |

TABLE 1-continued

| Name of primer oligo | Sequence (5' → 3') | Intended Use |
|---|---|---|
| ACTB-5'R_5'Bio | [Bio-ON] AGGTGTGGTGCCAGATTTTC | To be bound to microscope slide |
| ACTB-5'F_5'BioM | [Bio-ON] AAAAAAAAAAGGCATGGGTCAGAAGGATT | To be bound to microscope slide |
| ACTB-5'R_5'BioM | [Bio-ON] AAAAAAAAAAGGTGTGGTGCCAGATTTTC | To be bound to microscope slide |
| ACTB-5'F_ExS | GGCATGGGUCAGAAGGATT | For PCR |
| ACTB-5'R_ExS | AGGTGTGGUGCCAGATTTTC | For PCR |
| ACTB-5'F_ExL | GGCATGGGZCAGAAGGATT | For PCR |
| ACTB-5'R_ExL | AGGTGTGGZGCCAGATTTTC | For PCR |
| ACTB-5'F_5'BioM_Cy5 | [Bio-ON] AAAAAAAAAAGGCATGGGTCAGAAGGATT[Cy5] | For checking oligo immobilization |

Bio-ON: the biotinylated 5' end
Cy5: the 3' end fluorescently labeled with Cy5
U: T labeled with a short wavelength (510/530) exciton dye
Z: T labeled with a long wavelength (570/590) exciton dye U (T labeled with a short wavelength (510/530) exciton dye) and Z (T labeled with a long wavelength (570/590) exciton dye) have the structures represented by the following chemical formulae, respectively.

U: T labeled with short wavelength (510/530) exciton dye (D514)

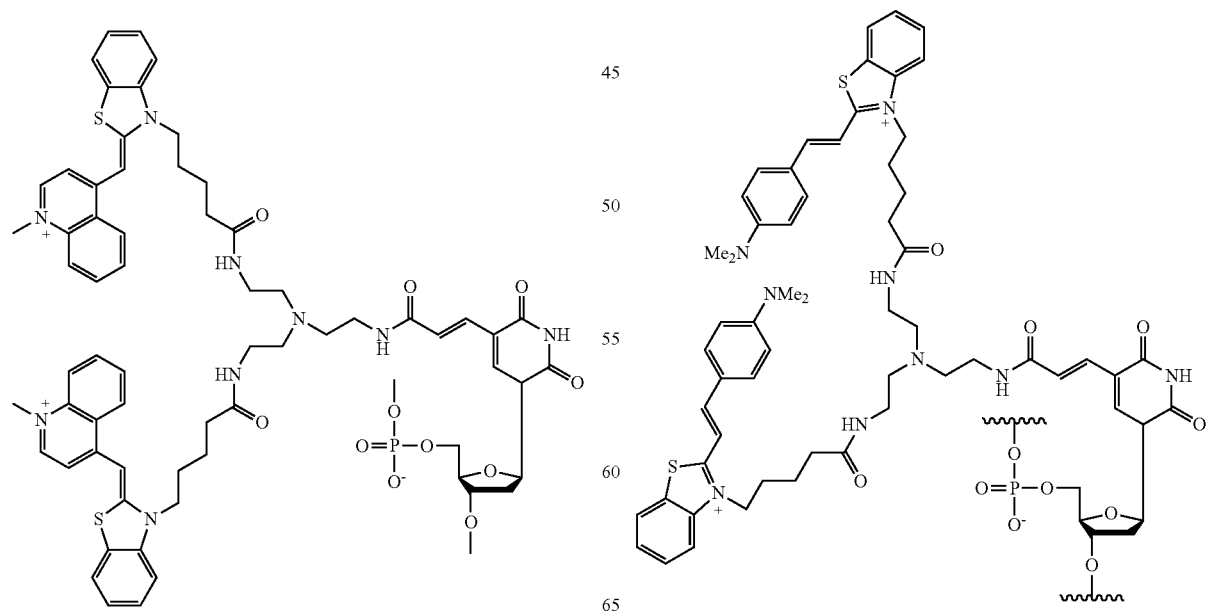

Z: T labeled with long wavelength (570/590) exciton dye (D570)

The structure of U (T labeled with a short wavelength (510/530) exciton dye) is the same as the structure of the exciton dye-labeled T in the above-described DNA oligomer (oligonucleotide) 110. The nucleic acids containing U (T labeled with a short wavelength (510/530) exciton dye) were synthesized in the same manner as in the synthesis example. The nucleic acids containing Z (T labeled with a long wavelength (570/590) exciton dye) were synthesized in a manner equivalent to those in the synthesis example.

The following sequence identification numbers are assigned to the primer oligos shown in Table 1 above.

```
ACTB-T7RNAF primer
(5'-CTAATACGACTCACTATAGGGAGAATGGATGATGATATCGCCGCG
CT-3': SEQ ID NO: 3)

ACTB-RNAR primer
(5'-CATTTTTAAGGTGTGCACTTTTATTCAACTGGTC-3': SEQ ID
NO: 4)

ACTB-5'F primer
(5'-GGCATGGGTCAGAAGGATT-3': SEQ ID NO: 5)

ACTB-5'R primer
(5'-AGGTGTGGTGCCAGATTTTC-3': SEQ ID NO: 6)

ACTB-5'F_5'Bio primer
(5'-GGCATGGGTCAGAAGGATT-3', with the 5'-end being
biotinylated: SEQ ID NO: 7)

ACTB-5'R_5'Bio primer
(5'-AGGTGTGGTGCCAGATTTTC-3', with the 5'-end being
biotinylated: SEQ ID NO: 8)

ACTB-5'F_5'BioM primer
(5'-AAAAAAAAAAGGCATGGGTCAGAAGGATT-3', with the
5'-end being biotinylated: SEQ ID NO: 9)

ACTB-5'R_5'BioM primer
(5'-AAAAAAAAAAAGGTGTGGTGCCAGATTTTC-3', with the
5'-end being biotinylated: SEQ ID NO: 10)

ACTB-5'F_ExS
(5'-GGCATGGGT*CAGAAGGATT-3', with the 5'-end
being biotinylated: SEQ ID NO: 11, T at the
position indicated with "T*" was labeled [the
above-described U])

ACTB-5'R_ExS
(5'-AGGTGTGGT*GCCAGATTTTC-3', with the 5'-end
being biotinylated: SEQ ID NO: 12, T at the
position indicated with "T*" was labeled [the
above-described U])

ACTB-5'F_ExL
(5'-GGCATGGGT*CAGAAGGATT-3', with the 5'-end
being biotinylated: SEQ ID NO: 13, T at the
position indicated with "T*" was labeled [the
above-described Z])

ACTB-5'R_ExL
(5'-AGGTGTGGT*GCCAGATTTTC-3', with the 5'-end
being biotinylated: SEQ ID NO: 14, T at the
position indicated with "T*" was labeled [the
above-described Z])

ACTB-5'F_5'BioM_Cy5
(5'-AAAAAAAAAAGGCATGGGTCAGAAGGATT-3', with the
5' end being biotinylated and the 3' end being
labeled with Cy5: SEQ ID NO: 15)
```

Operon Biotechnologies, Inc. was commissioned to synthesize the oligos. As described above, the synthesis methods of these oligos were the same as or equivalent to the synthesis method of the DNA oligomer (oligonucleotide) 110. The quality of each of the synthesized primer oligos was checked in the manner described below.

1. Human beta-actin cDNA-containing E. coli clone AK025375 in the cDNA clone collection owned by RIKEN Omics Science Center was streaked on an LB agar medium containing ampicillin, and cultured at 37° C. overnight. Thereafter, a single colony was obtained.

2. The single colony was scraped and suspended in 10 µl of sterile distilled water.

3. A 0.2 ml PCR tube was provided, in which a reaction solution was prepared by mixing 1 mM magnesium chloride, 0.16 mM dNTP, and 1.25 units of HotStar Taq DNA polymerase (QIAGEN) with a buffer solution for HotStar Taq. To the reaction solution, 1 µl of the above-described suspension of the beta-actin cDNA-containing E. coli clone was added. To the resultant mixture, one of the following primer pairs (A), (B), (C), and (D) was added: the primer pair (A) composed of 0.5 µM ACTB-5'F primer (5'-GGCATGGGTCAGAAGGATT-3': SEQ ID NO: 5) and 0.5 µM ACTB-5'R primer (5'-AGGTGTGGTGCCA-GATTTTC-3': SEQ ID NO: 6); the primer pair (B) composed of 0.5 µM ACTB-T7RNAF primer (5'-CTAATAC-GACTCACTATAGGGAGAATGGATGATGATATCGCC GCGCT-3' SEQ ID NO: 3) and 0.5 µM ACTB-RNAR primer (5'-CATTTTTAAGGTGTGCACTTTTAT-TCAACTGGTC-3': SEQ ID NO: 4); the primer pair (C) composed of 0.5 µM ACTB-5'F_5'Bio primer (5'-GGCATGGGTCAGAAGGATT-3', with the 5'-end being biotinylated SEQ ID NO: 7) and 0.5 µM ACTB-5'R_5'Bio primer (5'-AGGTGTGGTGCCAGATTTTC-3', with the 5'-end being biotinylated SEQ ID NO: 8); and the primer pair (D) composed of 0.5 µM ACTB-5'F_5'BioM primer (5'-AAAAAAAAAAGGCATGGGTCAGAAGGATT-3', with the 5'-end being biotinylated: SEQ ID NO: 9) and 0.5 µM ACTB-5'R_5'BioM primer (5'-AAAAAAAAAAAGGTGTGGTGCCAGATTTTC-3', with the 5'-end being biotinylated SEQ ID NO: 10). Thus, a PCR reaction solution with a total amount of 50 µl was prepared.

4. The 0.2 ml PCR tube containing the PCR reaction solution was placed in a GeneAmp PCR System 9700 thermal cycler (Applied Biosystems). The reaction solution was heated at 95° C. for 15 minutes, and then was subjected to 30 cycles of the following thermal treatment: 94° C. for 15 seconds, 60° C. for 30 seconds, and 72° C. for 2 minutes. Thereafter, the reaction solution was incubated at 72° C. for 10 minutes to terminate the reaction.

5. To 50 µl of the reaction solution after the termination of the reaction, 90 µl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 µl of 70% ethanol was added thereto. The resultant mixture was allowed to stand for 15 seconds, after which the ethanol was discarded. 200 µl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 41 µl of sterile distilled water was added thereto and mixed together well. The resultant mixture was placed on the magnet plate again, and allowed to stand still for 5 minutes. Thereafter, 40 µl of the supernatant was collected.

6. 100 µl of MPG Streptavidin beads (Takara Bio Inc.) were measured and collected. They were placed on the magnet plate, and allowed to stand still for 3 minutes. Thereafter, the supernatant was removed. 100 µl of a washing buffer (4.5 mol/l sodium chloride containing 50 mmol/l ethylenediaminetetraacetic acid) was added so as to suspend the beads. The thus-obtained suspension was placed on the magnet plate and allowed to stand still for 3 minutes. Thereafter, the supernatant was removed. The washing with the washing buffer was repeated to a total of three times. Lastly, 200 µl of the washing buffer was added to resuspend the beads.

7. 20 µl of the sample containing the primer pair (A), (C), or (D) was measured and collected. 2.2 µl of a 10×RnaseOne buffer was added thereto, and 51.8 µl of the MPG Streptavidin beads resuspended with the washing buffer further was added thereto. Thereafter, the resultant mixture was incubated at 37° C. for 30 minutes. During the incubation, the mixture was subjected to a suspension process using a pipetter 10 times with 5 minute intervals. After the completion of the incubation, the mixture was placed on a magnet plate and allowed to stand still for 5 minutes. The supernatant was collected, and the MPG Streptavidin beads were captured. Thereafter, the residue was used as a sample.

8. 1.0% agarose gel was prepared, and applied to electrophoresis in a TAE buffer at 100 V for 70 minutes. After the completion of the electrophoresis, the gel was stained with SYBR Gold for 10 minutes at room temperature while being shaken. After the completion of the staining, the gel was taken out, and the bands were observed under ultraviolet irradiation.

Figure 3:
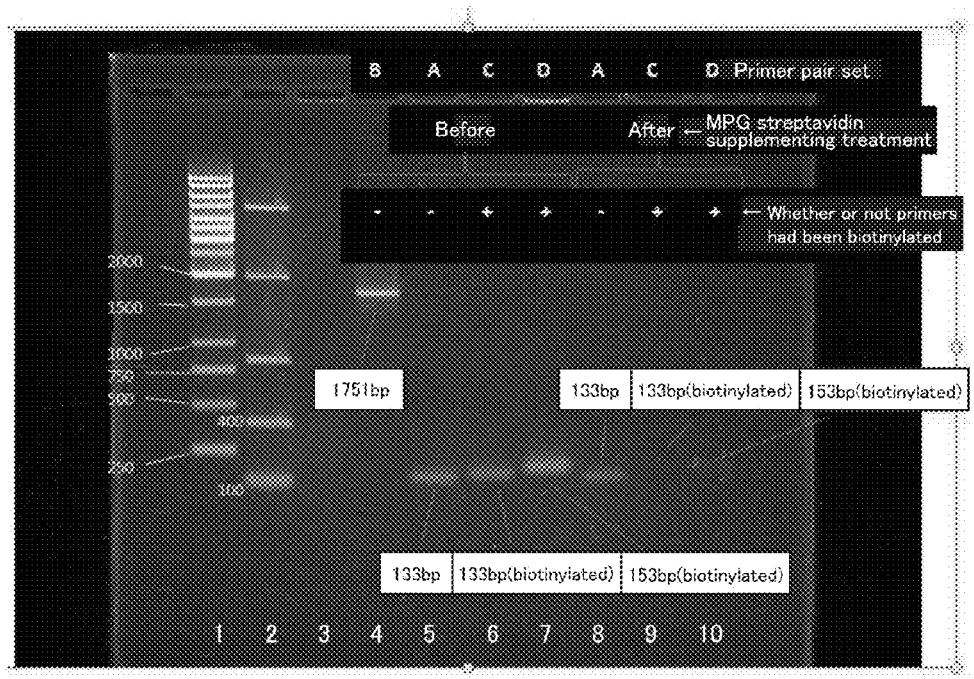
FIG. 3 is a photograph showing the result of checking the quality of oligos synthesized in Example 2-A.

FIG. 3 is a photograph showing the result of checking the quality of the synthesized oligos.

(Explanation of FIG. 3)
−: the primers had not been biotinylated
+: the primers had been biotinylated
Lane 1: marker
Lane 2: marker
Lane 3: empty lane
Lane 4: the sample after the PCR performed using the primer set B
Lane 5: the sample after the PCR performed using the primer set A
Lane 6: the sample after the PCR performed using the primer set C
Lane 7: the sample after the PCR performed using the primer set D
Lane 8: the supernatant sample obtained after bringing the sample after the
PCR performed using the primer set A into contact with the streptavidin beads
Lane 9: the supernatant sample obtained after bringing the sample after the PCR performed using the primer set C into contact with the streptavidin beads
Lane 10: the supernatant sample obtained after bringing the sample after the PCR performed using the primer set D into contact with the streptavidin beads From the result shown in Lane 4, it was confirmed that the primer oligo set for preparing a template for beta-actin messenger RNA synthesis works. From the results shown in Lanes 5 and 8, it was confirmed that the primer oligo set A for PCR experiments works. It was also confirmed that these primer oligos were synthesized properly so as not to be biotinylated, as designed. From the results shown in Lanes 6 and 9, it was confirmed that the primer oligo set C works. It was also confirmed that these primer oligos were synthesized properly so as to be biotinylated, as designed. From the results shown in Lanes 7 and 10, it was confirmed that the primer oligo set D works. It was also confirmed that these primer oligos were synthesized properly so as to be biotinylated, as designed.

Example 2-B: Preparation of Beta-Actin DNA

1. The single colony of the human beta-actin cDNA-containing *E. coli* clone AK025375 was scraped, and suspended in 10 µl of sterile distilled water.

2. A 0.2 ml PCR tube was provided, in which a reaction solution was prepared by mixing 1 mM magnesium chloride, 0.16 mM dNTP, 0.5 ACTB-5'F primer (5'-GGCATGGGTCAGAAGGATT-3': SEQ ID NO: 5), 0.5 ACTB-5'R primer (5'-AGGTGTGGTGCCAGATTTTC-3': SEQ ID NO: 6), and 1.25 units of HotStar Taq DNA polymerase (QIAGEN) with a buffer solution for HotStar Taq. To the reaction solution, 1 µl of the above-described suspension of the beta-actin cDNA-containing *E. coli* clone was added. Thus, a PCR reaction solution with a total amount of 50 µl was prepared.

3. The 0.2 ml PCR tube containing the PCR reaction solution was placed in a GeneAmp PCR System 9700 thermal cycler (Applied Biosystems). The reaction solution was heated at 95° C. for 15 minutes, and then was subjected to 30 cycles of the following thermal treatment: 94° C. for 15 seconds, 60° C. for 30 seconds, and 72° C. for 30 seconds. Thereafter, the reaction solution was incubated at 72° C. for 10 minutes to terminate the reaction.

4. To 50 µl of the reaction solution after the termination of the reaction, 90 µl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 µl of 70% ethanol was added thereto. The resultant mixture was allowed to stand for 15 seconds, after which the ethanol was discarded. 200 µl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 41 µl of sterile distilled water was added thereto and mixed together well. The resultant mixture was placed on the magnet plate again, and allowed to stand still for 5 minutes. Thereafter, 40 µl of the supernatant was collected.

5. The thus-obtained sample solution was subjected to measurement using a bioanalyzer DNA 1000 kit (Agilent Technologies, Inc.).

Figure 4:
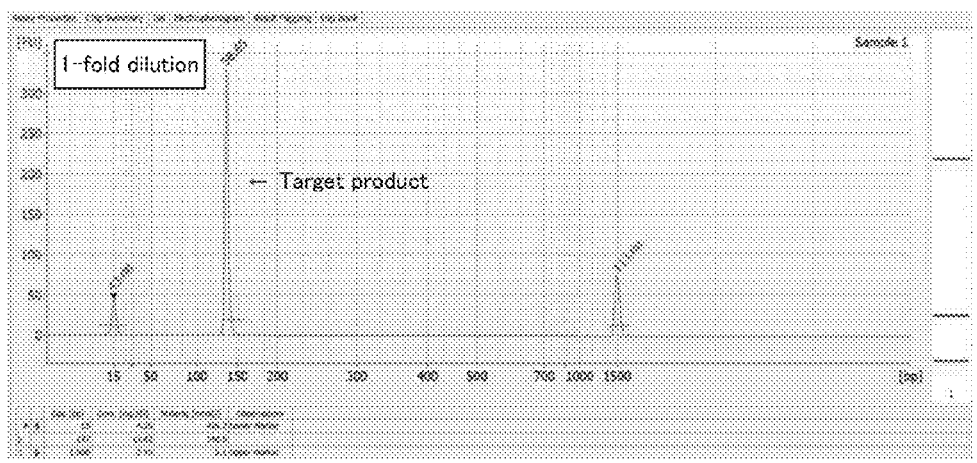
FIG. 4 shows the result of electrophoresis of a product obtained after PCR in Example 2-B.

FIG. 4 shows the result of electrophoresis of the product obtained after the PCR. As can be seen from FIG. 4, it was confirmed that the PCR product with a size of 133 bp could be synthesized as desired. This PCR product was used as a template in primer-immobilized PCR to be performed subsequently.

Example 2-C: Preparation of Beta-Actin Messenger RNA

1. The single colony of the human beta-actin cDNA-containing *E. coli* clone AK025375 was scraped, and suspended in 100 µl of sterile distilled water.

2. A 0.2 ml PCR tube was provided, in which a reaction solution was prepared by mixing 1.5 mM magnesium chloride, 0.2 mM dNTP, 0.3 µM ACTB-T7RNAF primer (5'-CTAATACGACTCACTATAGGGAGAATGGATGATGA- TATCGCCGCGCT-3' SEQ ID NO: 3), 0.3 μM ACTB-RNAR primer (5'-CATTTTTAAGGTGTGCACTTTTATTCAACTGGTC-3': SEQ ID NO: 4), and 1 unit of KOD-Plus-Neo DNA polymerase (TOYOBO) with a buffer solution for KOD-Plus-Neo. To the reaction solution, 1 μl, 2 μl, 5 μl, or 10 μl of the above-described suspension of the beta-actin cDNA-containing E. coli clone was added. Thus, four kinds of PCR reaction solutions, each having a total amount of 50 were prepared.

3. The 0.2 ml PCR tube containing the PCR reaction solution was placed in a GeneAmp PCR System 9700 thermal cycler (Applied Biosystems). The reaction solution was heated at 94° C. for 2 minutes, and then was subjected to 30 cycles of the following thermal treatment: 98° C. for 10 seconds, 60° C. for 30 seconds, and 68° C. for 1 minute. Thereafter, the reaction solution was incubated at 68° C. for 10 minutes to terminate the reaction.

4. To 50 μl of the reaction solution after the termination of the reaction, 90 μl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 μl of 70% ethanol was added thereto. The resultant mixture was allowed to stand for 15 seconds, after which the ethanol was discarded. 200 μl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 41 μl of sterile distilled water was added thereto and mixed together well. The resultant mixture was placed on the magnet plate again, and allowed to stand still for 5 minutes. Thereafter, 40 μl of the supernatant was collected. This was used as a template DNA for beta-actin messenger RNA synthesis.

5. The collected template DNA for beta-actin messenger RNA synthesis was applied to electrophoresis using 1.0% agarose gel and a TAE buffer at 100 V for 70 minutes. After the completion of the electrophoresis, the gel was stained with a TAE buffer containing SYBR Gold for 10 minutes at room temperature while being shaken. After the completion of the staining, the gel was taken out, and the bands were observed under ultraviolet irradiation. The concentration of the product obtained after the PCR was measured using a NanoDrop 8000 (Thermo SCIENTIFIC).

6. A 0.2 ml PCR tube was provided, in which a reaction solution was prepared by mixing 1 M dithiothreitol, 0.16 mM CTP, 0.16 mM UTP, 0.16 mM GTP, 0.16 mM ATP, and 1 μl of CUGA 7 Enzyme Solution (NIPPON GENE CO., LTD.) with a buffer solution for CUGA7 transcription. The template DNA for beta-actin messenger RNA synthesis was added thereto so that the concentration thereof became 0.1 pmol/l. Thus, a reaction solution with a total amount of 20 μl was prepared. The reaction solution was incubated at 37° C. for 2 hours. After the incubation, 2 μl of a DNase enzyme solution was added, and the resultant mixture was incubated at 37° C. for 30 minutes.

7. To 22 μl of the reaction solution after the termination of the reaction, 39.6 μl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 μl of 70% ethanol was added thereto. The resultant mixture was allowed to stand for 15 seconds, after which the ethanol was discarded. 200 μl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 21 μl of sterile distilled water was added thereto and mixed together well. The resultant mixture was placed on the magnet plate again, and allowed to stand still for 5 minutes. Thereafter, 20 μl of the supernatant was collected. Again, 21 μl of sterile distilled water was added thereto, and mixed together well. The mixture was placed on the magnet plate again, and allowed to stand still for 5 minutes. Thereafter, 20 μl of the supernatant was collected, which was mixed with the above-described collected sample. Thus, a beta-actin messenger RNA solution of 40 μl was obtained.

8. The beta-actin messenger RNA solution was subjected to measurement using a bioanalyzer RNA6000 pico kit (Agilent Technologies, Inc.). The concentration was measured using a NanoDrop 8000 (Thermo SCIENTIFIC).

Figure 5:
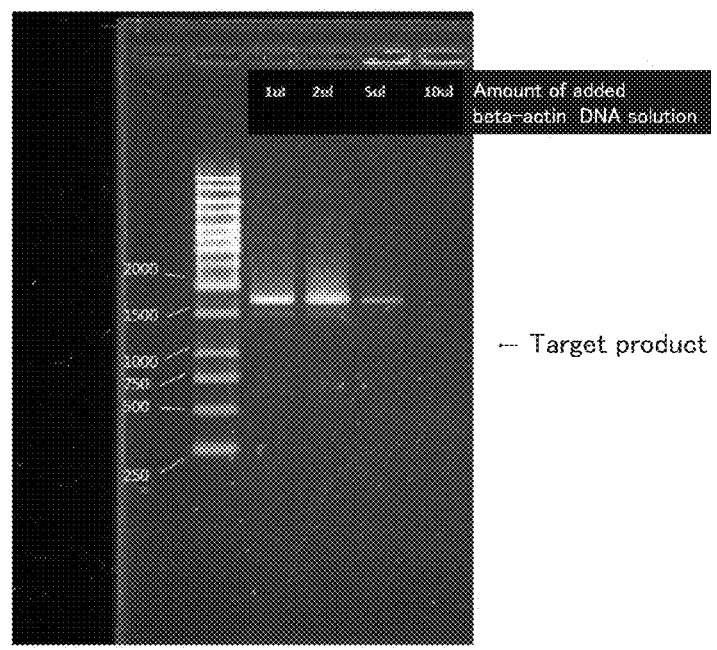
FIG. 5 is a photograph showing the result of synthesizing a template DNA for beta-actin messenger RNA synthesis in Example 2-C.

FIG. 5 is a photograph showing the result of synthesizing a template DNA for beta-actin messenger RNA synthesis. In the template DNA synthesis shown in FIG. 5, PCR was carried out while changing the amount of the suspension of the human beta-actin cDNA-containing E. coli clone AK025375 to be added (1 μl, 2 μl, 5 μl, and 10 μl). As can be seen from FIG. 5, when the added amount of the suspension was 1 μl to 5 μl, the template DNA for beta-actin messenger RNA synthesis with a desired size of 1751 bp could be synthesized.

Figure 6:
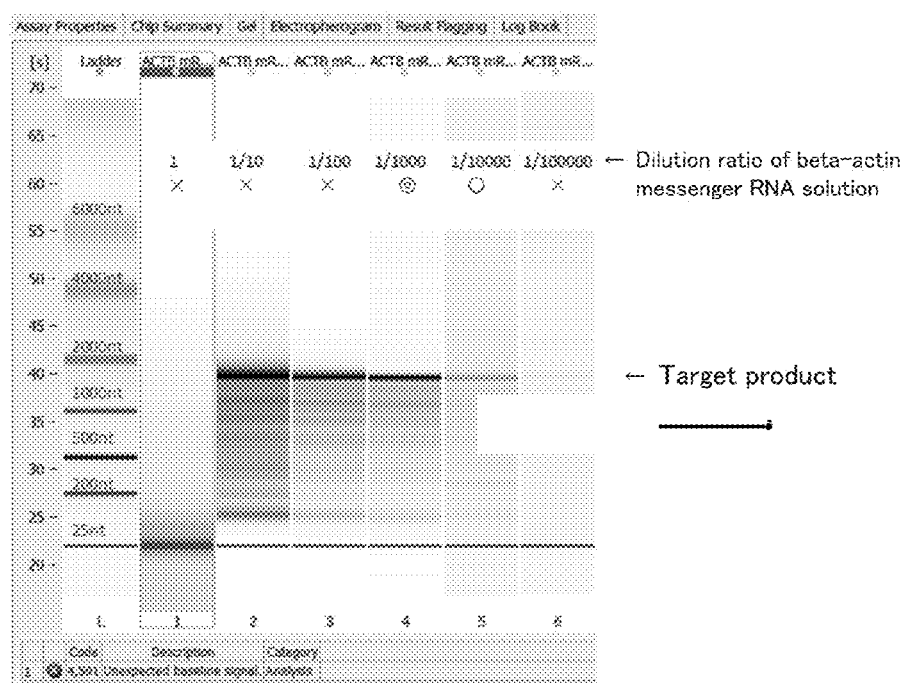
FIG. 6 shows the result of synthesizing beta-actin messenger RNA using a CUGA 7 in vitro Transcription Kit in Example 2-C.

FIG. 6 shows the result of synthesizing beta-actin messenger RNA using a CUGA 7 in vitro Transcription Kit. As can be seen from FIG. 6, the RNA product with a desired size of 1730 bp could be synthesized.
(Explanation of FIG. 6)
L: marker
Lane 1: the sample after the RNA synthesis (no dilution)
Lane 2: the sample after the RNA synthesis (diluted 10-fold with RNase free distilled water)
Lane 3: the sample after the RNA synthesis (diluted 100-fold with RNase free distilled water)
Lane 4: the sample after the RNA synthesis (diluted 1000-fold with RNase free distilled water)
Lane 5: the sample after the RNA synthesis (diluted 10,000-fold with RNase free distilled water)
Lane 6: the sample after the RNA synthesis (diluted 100,000-fold with RNase free distilled water)

Example 2-D: Experiment to Check the Operation of a Thermal Cycler and to Check PCR on a Microscope Slide Substrate 1. An adhesive frame (TAKARA BIO INC., Takara Slide Seal for in situ PCR) was attached to a microscope slide to provide a reaction chamber.

2. The single colony of the human beta-actin cDNA-containing E. coli clone AK025375 was scraped, and suspended in 100 μl of sterile distilled water.

3. A reaction solution was prepared by mixing 1.5 mM magnesium chloride, 0.2 mM dNTP, a primer mixture (Forward: 5'-GGCATGGGTCAGAAGGATT-3', Reverse: 5'-AGGTGTGGTGCCAGATTTTC-3', 0.2 μM each) specific to the beta-actin messenger RNA, and 1 unit of Platinum Taq DNA polymerase (Invitrogen) with a buffer solution for Platinum Taq. To the reaction solution, 1 μl of the above-described suspension of the beta-actin cDNA-containing *E. coli* clone was added. Thus, a PCR reaction solution with a total amount of 50 µl was prepared. 25 µl of the above-described PCR reaction solution was added to the reaction chamber, and the chamber was closed with a cover film (TAKARA BIO INC., Takara Slide Seal for in situ PCR).

```
Forward:
                                   (SEQ ID NO: 16)
5'-GGCATGGGTCAGAAGGATT-3'

Reverse:
                                   (SEQ ID NO: 17)
5'-AGGTGTGGTGCCAGATTTTC-3'
```

4. The microscope slide on which the above-described reaction solution was enclosed in the reaction chamber was placed in a reaction chamber of a GenePro Thermal Cycler (Bioer Technology Co., Ltd.) equipped with a GenePro Insitu "Japanese Version" B-4 block. The microscope slide was heated at 94° C. for 4 minutes, and then was subjected to 30 cycles of the following thermal treatment: 94° C. for 1 minute, 60° C. for 1 minute, and 72° C. for 1 minute. Thereafter, the microscope slide was incubated at 72° C. for 5 minutes to terminate the reaction.

5. The microscope slide after the termination of the reaction was taken out, and while peeling off the cover film, 20 µl of the reaction solution was collected using a pipetter. To 20 µl of the collected reaction solution, 36 µl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 µl of 70% ethanol was added thereto. The resultant mixture was allowed to stand for 15 seconds, after which the ethanol was discarded. 200 µl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 21 µl of sterile distilled water was added thereto and mixed together well. The resultant mixture was placed on the magnet plate again, and allowed to stand still for 5 minutes. Thereafter, 20 µl of the supernatant was collected.

6. The thus-obtained sample solution was subjected to measurement using a bioanalyzer DNA 1000 kit (Agilent Technologies, Inc.).

Figure 7:
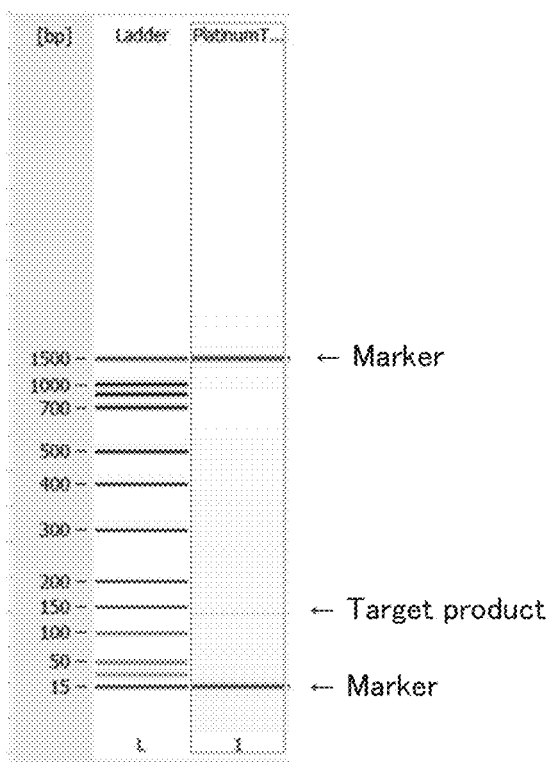
FIG. 7 shows the result of checking the operation of a GenePro Thermal Cycler (Bioer Technology Co., Ltd.) equipped with a GenePro Insitu "Japanese Version" B-4 block and the result of checking a PCR reaction in a reaction chamber prepared using a microscope slide in Example 2-D.

FIG. 7 shows the result of checking the operation of the GenePro Thermal Cycler (Bioer Technology Co., Ltd.) equipped with the GenePro Insitu "Japanese Version" B-4 block and the result of checking the PCR reaction in the reaction chamber prepared using the microscope slide. As can be seen from FIG. 7, as in the case of the PCR experiment carried out using the PCR tube (Example 2-A, Lane 5), the PCR product with a size of 133 bp could be synthesized (the line was pale, but could be recognized clearly). This confirmed the operation of the thermal cycler. Also, it was confirmed that a PCR reaction can proceed in a reaction chamber prepared using a microscope slide.

(Explanation of FIG. 7)
L: marker
Lane 1: the sample after the PCR

Example 2-E: Experiment to Check the Binding of Biotinylated Primers to a Biotin-Coated Cover Slip 1. A primer of the present example (ACTB-5'F_5'BioM_Cy5: SEQ ID NO: 15) was synthesized by modifying a specific primer (5'-AAAAAAAAAAGGCATGGGTCAGAAGGATT-3') so as to biotinylate the 5' end and label the 3' end with Cy5.

2. An adhesive frame (TAKARA BIO INC., Takara Slide Seal for in situ PCR) was attached to a biotin-coated surface of a biotin-coated cover slip (Alliance Technology, Biotin/cover slip/Bio_02-C) to provide a reaction chamber. A 20 µg/ml streptavidin protein solution prepared using physiological saline containing glycerol was added to the chamber so that the biotin-coated surface of the cover slip in the chamber was entirely coated with the solution. In order to prevent the surface from being dried, the chamber was covered with the lid of a petri dish. The chamber was then allowed to stand at 37° C. for 30 minutes, thereby immobilizing the streptavidin protein on the surface of the cover slip. After the immobilization, the cover slip was washed three times with physiological saline, thus removing the surplus streptavidin protein.

3. Glycerol was added to physiological saline so that the concentration thereof became 10%. The Cy5-labeled biotinylated primer was added thereto so that the final concentration of the primer became 50 pmol/l or 200 pmol/l. Thus, two kinds of Cy5-labeled biotinylated primer solutions of 50 µl were prepared in separate 0.5 ml tubes. To the reaction chamber on the streptavidin immobilized cover slip, each Cy5-labeled biotinylated primer solution was added so that the surface of the cover slip in the chamber was entirely coated with the solution. In order to prevent the surface from being dried, the chamber was covered with the lid of a petri dish. The chamber then was allowed to stand at 37° C. for 30 minutes, thereby immobilizing the Cy5-labeled biotinylated primer. After the immobilization, the cover slip was washed three times with physiological saline, thus removing the surplus primer.

4. 25 µl of physiological saline was added, and the chamber was closed with a cover film (TAKARA BIO INC., Takara Slide Seal for in situ PCR). Then, the cover slip was excited at an excitation wavelength of 640 nm using an Eclipse Ti fluorescence microscope (NIKON CORPORATION), and the fluorescence at 692±20 nm was observed.

Figure 8:
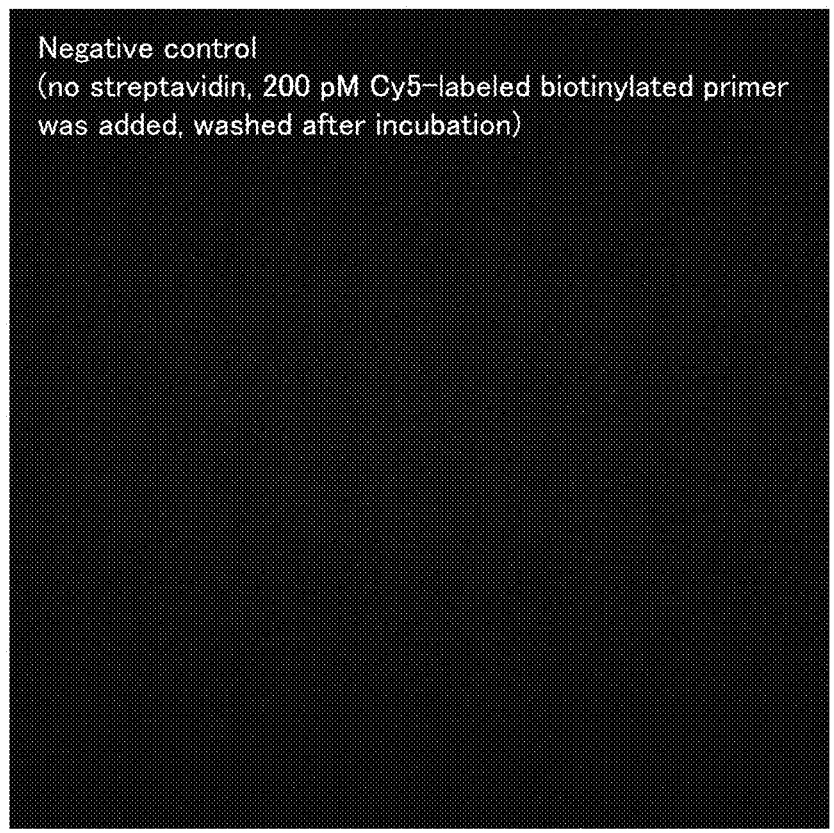
FIG. 8 is a photograph showing the result of observation using a fluorescence microscope in Example 2-E.
Figure 9:
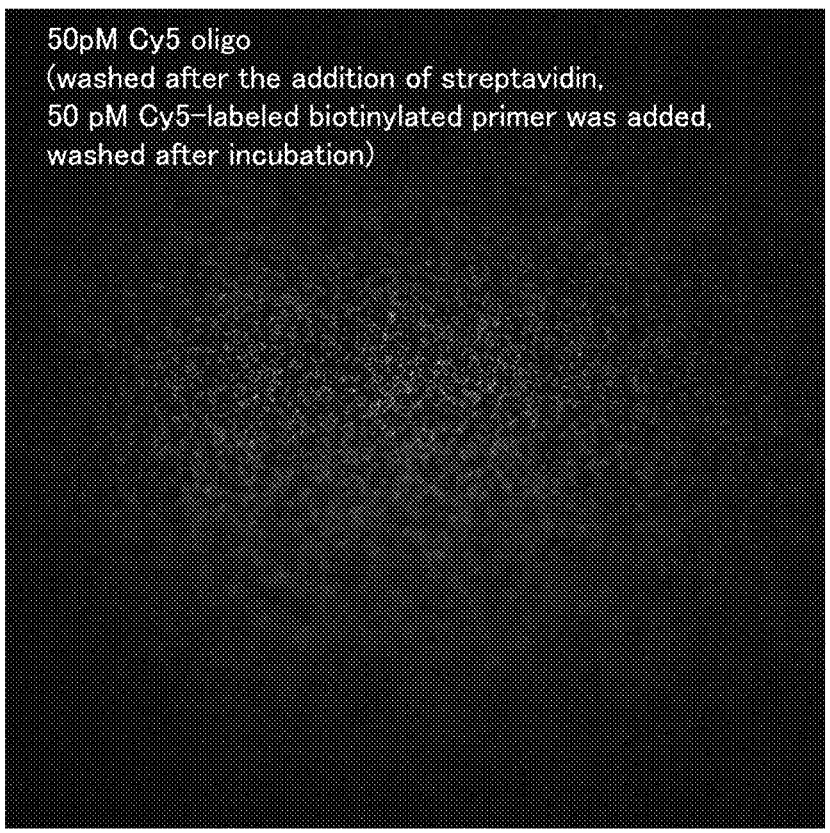
FIG. 9 is a photograph showing the result of observation using a fluorescence microscope in Example 2-E.
Figure 10:
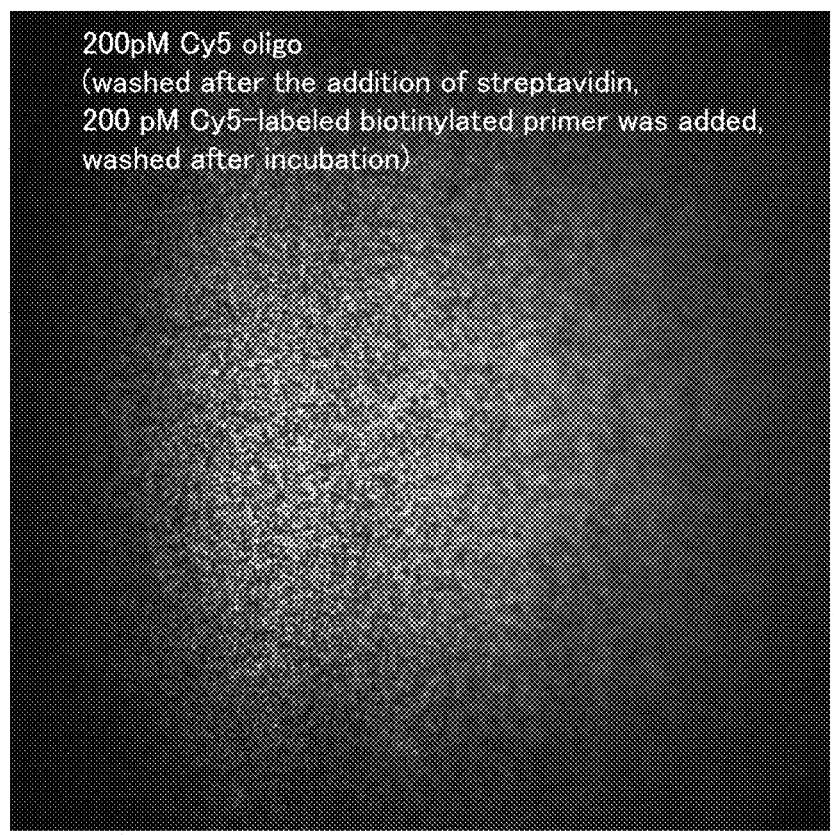
FIG. 10 is a photograph showing the result of observation using a fluorescence microscope in Example 2-E.

FIGS. 8, 9, and 10 are each a photograph showing the result of observation using the fluorescence microscope. FIG. 8 shows the result obtained regarding the negative control (no streptavidin, the 200 pM Cy5-labeled biotinylated primer was added, washed after the incubation); FIG. 9 shows the result obtained when the 50 pM Cy5 oligo was used (washed after the addition of streptavidin, the 50 pM Cy5-labeled biotinylated primer was added, washed after the incubation), and FIG. 10 shows the result obtained when the 200 pM Cy5 oligo was used (washed after the addition of streptavidin, the 200 pM Cy5-labeled biotinylated primer was added, washed after the incubation). As can be seen from FIGS. 8, 9, and 10, fluorescent spots derived from the Cy5 used as the label in the biotinylated primer changed in a concentration dependent manner, and in the image of the negative control in which streptavidin was not added, no fluorescent spot was observed. These results confirmed that the binding of the biotinylated primer was achieved successfully. Also, these results confirmed that the washing method employed in the present experiment is effective in removing non-specific biotinylated primers.

Example 2-F: Experiment in which the Effectiveness of a PCR Reaction System and the Effectiveness of Primer-Immobilized PCR in a Chamber Prepared Using a Glass Substrate were Checked Using Prepared Beta-Actin DNA 1. A primer pair of the present example was synthesized by biotinylating the 5' ends of specific primers (Forward: 5'-AAA AAA AAA AGG CAT GGG TCA GAA GGA TT-3' (SEQ ID NO: 1), Reverse: 5'-AAA AAA AAA AAG GTG TGG TGC CAG ATT TTC-3' (SEQ ID NO: 2)).
2. An adhesive frame (TAKARA BIO INC., Takara Slide Seal for in situ PCR) was attached to a biotin-coated surface of a biotin-coated cover slip (Alliance Technology, Biotin/cover slip/Bio_02-C) to provide a reaction chamber. A 20 µg/ml streptavidin protein solution prepared using physiological saline containing glycerol was added to the chamber so that the biotin-coated surface of the cover slip in the chamber was entirely coated with the solution. In order to prevent the surface from being dried, the chamber was covered with the lid of a petri dish. The chamber was then allowed to stand at 37° C. for 30 minutes, thereby immobilizing the streptavidin protein on the surface of the cover slip. After the immobilization, the cover slip was washed three times with physiological saline, thus removing the surplus streptavidin protein.
3. Glycerol was added to physiological saline so that the concentration thereof became 10%. Then, two kinds of the primers, namely, the biotinylated forward primer and the biotinylated reverse primer, were added thereto so that the final concentration of each of these primers became 3.3 µmol/l. To the reaction chamber on the streptavidin immobilized cover slip, the biotinylated primer pair solution was added so that the surface of the cover slip in the chamber was entirely coated with the solution. In order to prevent the surface from being dried, the chamber was covered with the lid of a petri dish. The chamber then was allowed to stand at 37° C. for 30 minutes, thereby immobilizing the biotinylated primer pair. After the immobilization, the cover slip was washed three times with physiological saline, thus removing the surplus primers.
4. A reaction solution was prepared by mixing 1.5 mM magnesium chloride, 0.2 mM dNTP, SYBR Green solution, and 1 unit of Platinum Taq DNA polymerase (Invitrogen) with a buffer solution for Platinum Taq. To the reaction solution, beta-actin DNA was added so that the concentration thereof became 20 pM. To the chamber on the cover slip having the primer pair immobilized thereon, 25 µl of the reaction solution was added, and the chamber was closed with a cover film (TAKARA BIO INC., Takara Slide Seal for in situ PCR).
5. The cover slip was placed in a reaction chamber of a GenePro Thermal Cycler (Bioer Technology Co., Ltd.) equipped with a GenePro Insitu "Japanese Version" B-4 block. The cover slip was heated at 94° C. for 4 minutes, and then was subjected to 40 cycles of the following thermal treatment: 94° C. for 1 minute, 60° C. for 1 minute, and 72° C. for 1 minute. Thereafter, the cover slip was incubated at 72° C. for 10 minutes to terminate the reaction.
6. The cover slip after the termination of the reaction was excited at an excitation wavelength of 470 nm using an Eclipse Ti fluorescence microscope (NIKON CORPORATION), and the fluorescence at 525 nm was observed.

Figure 11:
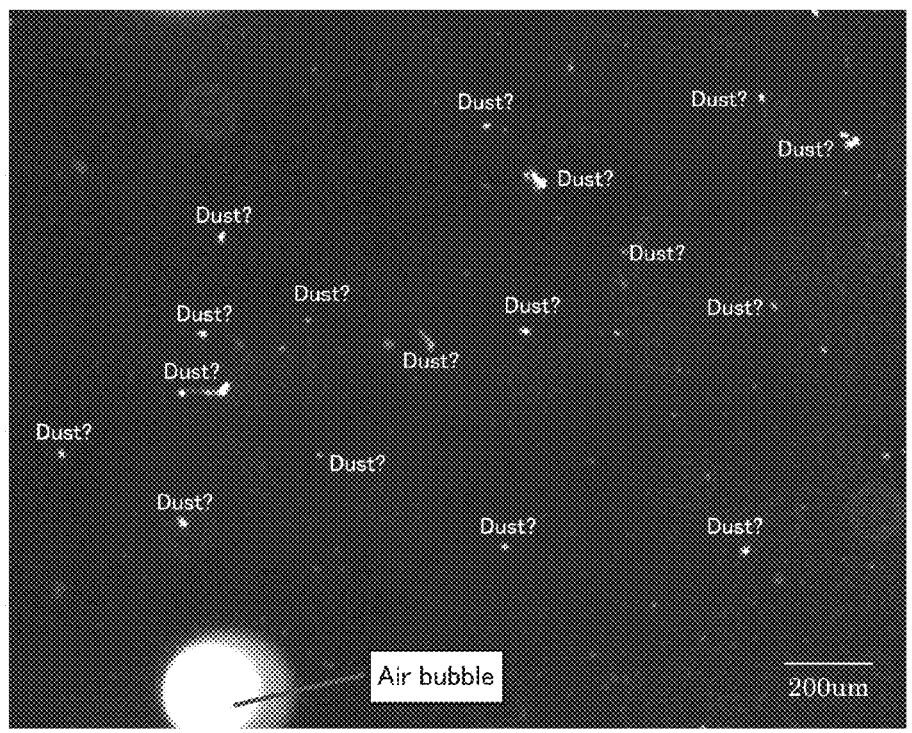
FIG. 11 is a photograph showing the result of observing a cover slip after primer-immobilized PCR with a fluorescence microscope in Example 2-F.

FIG. 11 is a photograph showing the result of observing the cover slip after the primer-immobilized PCR with the fluorescence microscope. As can be seen from FIG. 11, fluorescent spots derived from the SYBR Green were observed, which demonstrates that clusters of the double-stranded DNA were formed by the primer-immobilized PCR.

Example 2-G: Experiment in which the Effectiveness of a Two-Step RT-PCR Reaction System was Checked Using Prepared Beta-Actin Messenger RNA 1. In a 0.2 ml PCR tube, 10 µl of a solution was prepared that contained 2 µl of 1 µM ACTB-5'R primer, 1 µl of 10 mM dNTP, and 1 µg/µl beta-actin messenger RNA. The PCR tube was placed in a GeneAmp PCR System 9700 thermal cycler (Applied Biosystems), and incubated at 65° C. for 5 minutes. After the incubation, the PCR tube was cooled on ice for 2 minutes. To the tube containing the reaction solution, a buffer solution for SuperScript III, 2 µl of 0.1 M dithiothreitol, and 4 µl of 25 mM magnesium chloride were added. The tube was placed in a GeneAmp PCR System 9700 thermal cycler (Applied Biosystems), and incubated at 15° C. for 20 minutes. After the incubation, 1 µl of RNaseOUT and 1 µl of 200 units/µl SuperScript III were added to the tube containing the reaction solution. The tube then was placed in a GeneAmp PCR System 9700 thermal cycler (Applied Biosystems), and the reaction was allowed to proceed at
55° C. for 50 minutes and at 70° C. for 10 minutes. After the reaction, the tube containing the reaction solution was cooled on ice for 2 minutes. After the cooling, 50 units of RNase If (NEW ENGLAND BioLabs) and 2 units of Rnase H (TAKARA BIO INC.) were added to the tube, and the tube was placed in a GeneAmp PCR System 9700 thermal cycler (Applied Biosystems) and incubated at 37° C. for 30 minutes.
2. To 22 µl of the reaction solution after the termination of the reaction, 39.6 µl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 µl of 70% ethanol was added thereto. The resultant mixture was allowed to stand for 15 seconds, after which the ethanol was discarded. 200 µl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 21 µl of sterile distilled water was added thereto and mixed together well. The resultant mixture was placed on the magnet plate again, and allowed to stand still for 5 minutes. Thereafter, 20 µl of the supernatant was collected. This was used as a reverse transcription reaction product solution.
3. A 0.2 ml PCR tube was provided, in which a reaction solution was prepared by mixing 1 mM magnesium chloride, 0.16 mM dNTP, and 1.25 units of HotStar Taq DNA polymerase (QIAGEN) with a buffer solution for HotStar Taq. To the reaction solution,
1 µl of the above-described reverse transcription reaction product solution was added. To the resultant mixture, a primer pair composed of a 0.5 µM ACTB-5'F primer (5'-GGCATGGGTCAGAAGGATT-3': SEQ ID NO: 5) and a 0.5 µM ACTB-5'R primer (5'-AGGTGTGGTGCCA-GATTTTC-3': SEQ ID NO: 6) was added. Thus, a PCR reaction solution with a total amount of 50 µl was prepared.
4. The 0.2 ml PCR tube containing the PCR reaction solution was placed in a GeneAmp PCR System 9700 thermal cycler (Applied Biosystems). The reaction solution was heated at 95° C. for 15 minutes, and then was subjected to 30 cycles of the following thermal treatment: 94° C. for 15 seconds, 60° C. for 30 seconds, and 72° C. for 30 seconds. Thereafter, the reaction solution was incubated at 72° C. for 10 minutes to terminate the reaction.
5. To 50 µl of the reaction solution, 90 µl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 µl of 70% ethanol was added thereto. The resultant mixture was allowed to stand for 15 seconds, after which the ethanol was discarded. 200 µl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 41 µl of sterile distilled water was added thereto and mixed together well. The resultant mixture was placed on the magnet plate again, and allowed to stand still for 5 minutes. Thereafter, 40 µl of the supernatant was collected. This was used as a PCR reaction solution.
6. The thus-obtained sample solution was subjected to measurement using a bioanalyzer DNA 1000 kit (Agilent Technologies, Inc.).

Figure 12:
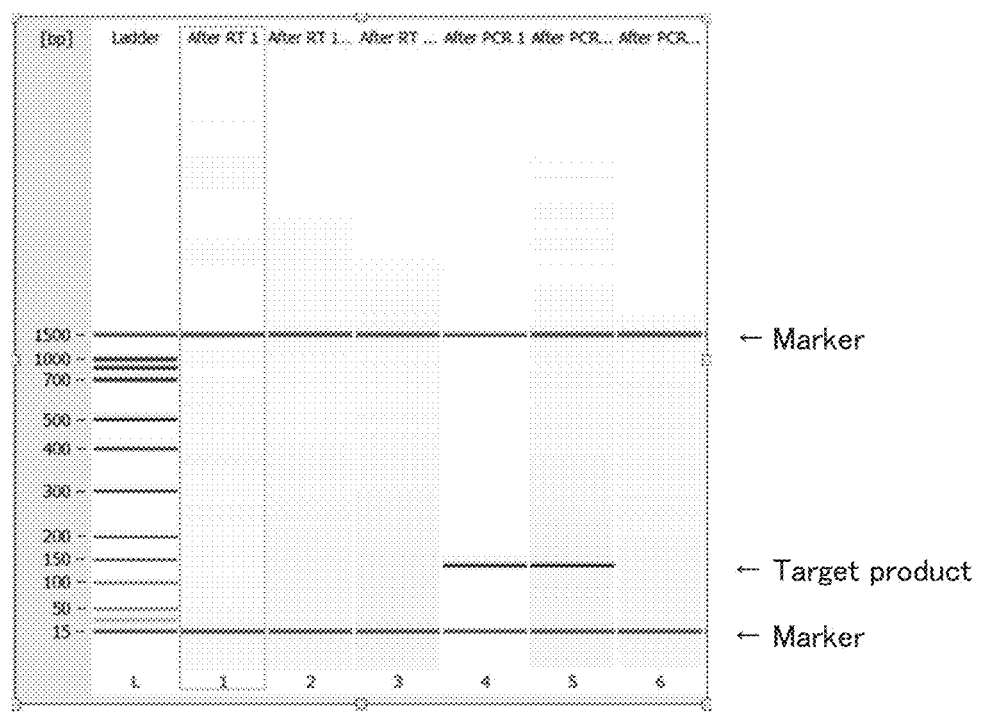
FIG. 12 shows the result of electrophoresis of a sample after two-step RT-PCR in Example 2-G.

FIG. 12 shows the result of electrophoresis of the sample after the two-step RT-PCR.
(Explanation of FIG. 12)
Lanes 1 to 3: the sample after the reverse transcription (1: no dilution, 2: 5-fold dilution, 3: negative control (no RNA template))
Lanes 4 to 6: the sample after the PCR (4: no dilution, 5: 5-fold dilution, 6: negative control (no RNA template))

As can be seen from Lanes 4 and 5 in FIG. 12, the RT-PCR product with a size of 133 bp could be synthesized. Thus, it was found that the beta-actin messenger RNA synthesized in Example 2-C can be used as a template in RT-PCR. Also, it was confirmed that the reaction system for two-step RT-PCR used in the present experiment functions successfully.

Example 2-H: Experiment to Check the Effectiveness of a One-Step RT-PCR Reaction System 1. In a 0.2 ml PCR tube, a reaction solution was prepared by mixing 1.6 mM magnesium sulfate, 0.2 mM dNTP, a primer mixture (Forward: 5'-GGCATGGGTCAGAAGGATT-3': SEQ ID NO: 16, Reverse: 5'-AGGTGTGGTGCCA-GATTTTC-3': SEQ ID NO: 17, 0.2 µM each) specific to beta-actin messenger RNA, beta-actin messenger RNA in an amount to achieve a final concentration of 0.5 µg/µl, and 2 units of Platinum Taq DNA polymerase (Invitrogen) with a buffer solution for Platinum Taq. To the reaction solution, 100 units, 200 units, or 500 units of SuperScript III (Invitrogen) were added. Thus, a reaction solution that allows both reverse transcription and PCR to be carried out therein was prepared.
2. The 0.2 ml PCR tube containing the reaction solution was placed in a GeneAmp PCR System 9700 thermal cycler (Applied Biosystems). The reaction solution was heated at 55° C. for 30 minutes and 94° C. for 2 minutes, and then was subjected to 40 cycles of the following thermal treatment: 94° C. for 15 seconds, 60° C. for 30 seconds, and 68° C. for 30 seconds. Thereafter, the reaction solution was incubated at 68° C. for 5 minutes to terminate the reaction.
3. To 50 µl of the reaction solution after the termination of the reaction, 90 µl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 µl of 70% ethanol was added thereto. The resultant mixture was allowed to stand for 15 seconds, after which the ethanol was discarded. 200 µl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 41 µl of sterile distilled water was added thereto and mixed together well. The resultant mixture was placed on the magnet plate again, and allowed to stand still for 5 minutes. Thereafter, 40 µl of the supernatant was collected.
4. The thus-obtained sample solution was subjected to measurement using a bioanalyzer DNA 1000 kit (Agilent Technologies, Inc.).

Figure 13:
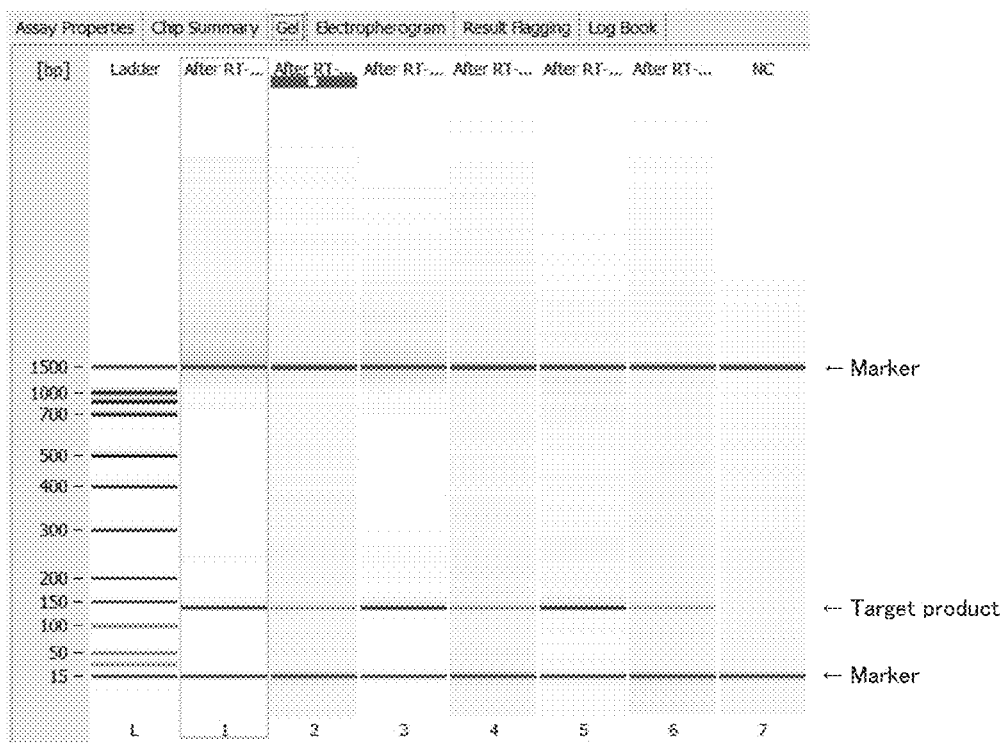
FIG. 13 shows the result of electrophoresis of a sample after one-step RT-PCR in Example 2-H.

FIG. 13 shows the result of electrophoresis of the sample after the one-step RT-PCR. As can be seen from FIG. 13, the band indicating the target product of 133 bp was observed. Thus, it was confirmed that the reaction system for one-step RT-PCR functions successfully. It was confirmed that the reaction system functions successfully in any of the cases where the amount of the reverse transcriptase SuperScript III is 100 units, 200 units, and 500 units.
(Explanation of FIG. 13)
L: marker
Lane 1: the sample after the RT-PCR, no dilution (100 units of SuperScript III were added)
Lane 2: the sample after the RT-PCR, diluted 5-fold (100 units of SuperScript III were added)
Lane 3: the sample after the RT-PCR, no dilution (200 units of SuperScript III were added)
Lane 4: the sample after the RT-PCR, diluted 5-fold (200 units of SuperScript III were added)
Lane 5: the sample after the RT-PCR, no dilution (500 units of SuperScript III were added)
Lane 6: the sample after the RT-PCR, diluted 5-fold (500 units of SuperScript III were added)
Lane 7: the sample after the RT-PCR, no dilution (no beta-actin messenger RNA serving as a template, 100 units of SuperScript III were added)

Example 2-I: Experiment to Check the Effectiveness of a One-Step RT-PCR Reaction System in a Chamber Prepared Using a Glass Substrate 1. An adhesive frame (TAKARA BIO INC., Takara Slide Seal for in situ PCR) was attached to a microscope slide to provide a reaction chamber.
2. 1.6 mM magnesium sulfate, 0.2 mM dNTP, a primer mixture (Forward: 5'-GGCATGGGTCAGAAGGATT-3': SEQ ID NO: 16, Reverse: 5'-AGGTGTGGTGCCA- GATTTTC-3': SEQ ID NO: 17, 0.2 µM each) specific to beta-actin messenger RNA, 200 units of SuperScript III (Invitrogen), and 2 units of Platinum Taq DNA polymerase (Invitrogen) were mixed with a buffer solution for Platinum Taq. Thus, a reaction solution that allows both reverse transcription and PCR to be carried out therein was prepared. To the reaction solution, beta-actin messenger RNA was added so that the concentration thereof became 0.5 µg/µl.

3. 25 µl of the reaction solution was added to the reaction chamber, and the chamber was closed with a cover film (TAKARA BIO INC., Takara Slide Seal for in situ PCR).

4. The microscope slide on which the above-described reaction solution was enclosed in the reaction chamber was placed in a reaction chamber of a GenePro Thermal Cycler (Bioer Technology Co., Ltd.) equipped with a GenePro Insitu "Japanese Version" B-4 block. The microscope slide was heated at 55° C. for 30 minutes and at 94° C. for 4 minutes, and then was subjected to 40 cycles of the following thermal treatment: 94° C. for 1 minute, 60° C. for 1 minute, and 68° C. for 1 minute. Thereafter, the microscope slide was incubated at 68° C. for 5 minutes to terminate the reaction.

5. The microscope slide after the termination of the reaction was taken out, and while peeling off the cover film, 20 µl of the reaction solution was collected using a pipetter. To 20 µl of the collected reaction solution, 36 µl of Agencourt AMPure XP (Beckman Coulter, Inc.) was added and mixed together. The mixture then was allowed to stand at room temperature for 30 minutes. 30 minutes later, the mixture was placed on a magnet plate, and allowed to stand still for 5 minutes. The supernatant was discarded with care not to draw up the beads, and 200 µl of 70% ethanol was added thereto. The resultant mixture was allowed to stand for 15 seconds, after which the ethanol was discarded. 200 µl of 70% ethanol was added again, and the mixture was allowed to stand for 15 seconds. The ethanol was discarded, after which the mixture was dried for 3 minutes with care not to allow contamination with dust. After the drying, the mixture was moved to the outside of the magnet plate. 21 µl of sterile distilled water was added thereto and mixed together well. The resultant mixture was placed on the magnet plate again, and allowed to stand still for 5 minutes. Thereafter, 20 µl of the supernatant was collected.

6. The thus-obtained sample solution was subjected to measurement using a bioanalyzer DNA 1000 kit (Agilent Technologies, Inc.).

Figure 14:
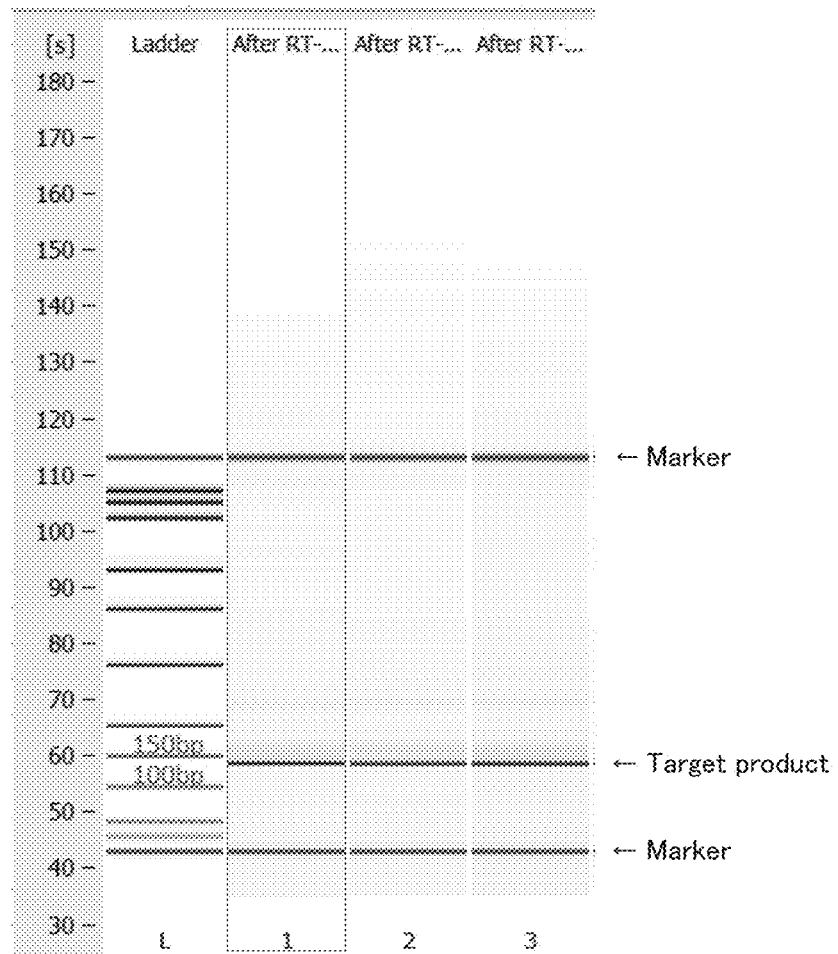
FIG. 14 shows the result of electrophoresis of a sample after one-step RT-PCR carried out in a chamber prepared using a glass substrate in Example 2-I.

FIG. 14 shows the result of electrophoresis of the sample after the one-step RT-PCR carried out in the chamber prepared using the glass substrate. As can be seen from FIG. 14, the band indicating the target product of 133 bp was observed. Thus, it was confirmed that the reaction system for one-step RT-PCR to be carried out in a chamber prepared using a glass substrate functions successfully.
(Explanation of FIG. 14)
L: marker
Lanes 1 to 3: the sample after the one-step RT-PCR Example 2-J: Experiment in which Beta-Actin Messenger RNA Molecules Obtained by Bridge RT-PCR Using an Immobilized Specific Primer Set were Counted 1. Primers of the present example were synthesized by biotinylating the 5' ends of specific primers (Forward: 5'-AAA AAA AAA AGG CAT GGG TCA GAA GGA TT-3' (SEQ ID NO: 1), Reverse: 5'-AAA AAA AAA AAG GTG TGG TGC CAG ATT TTC-3' (SEQ ID NO: 2)).

2. An adhesive frame (TAKARA BIO INC., Takara Slide Seal for in situ PCR) was attached to a biotin-coated surface of a biotin-coated cover slip (Alliance Technology, Biotin/cover slip/Bio_02-C) to provide a reaction chamber. A 20 µg/ml streptavidin protein solution prepared using physiological saline containing glycerol was added to the chamber so that the biotin-coated surface of the cover slip in the chamber was entirely coated with the solution. In order to prevent the surface from being dried, the chamber was covered with the lid of a petri dish. The chamber was then allowed to stand at 37° C. for 30 minutes, thereby immobilizing the streptavidin protein on the surface of the cover slip. After the immobilization, the cover slip was washed three times with physiological saline, thus removing the surplus streptavidin protein.

3. Glycerol was added to physiological saline so that the concentration thereof became 10%. Then, two kinds of the primers, namely, the biotinylated forward primer and the biotinylated reverse primer, were added thereto so that the final concentration of each of these primers became 3.3 µmol/l, or alternatively, as a negative control, only the forward primer was added thereto so that the final concentration of the forward primer became 6.6 µmol/l. To the reaction chamber on the streptavidin immobilized cover slip, the biotinylated primer pair solution or the forward primer solution as the negative control was added so that the surface of the cover slip in the chamber was entirely coated with the solution. In order to prevent the surface from being dried, the chamber was covered with the lid of a petri dish. The chamber then was allowed to stand at 37° C. for 30 minutes, thereby immobilizing the biotinylated primer pair or the biotinylated forward primer as the negative control. After the immobilization, the cover slip was washed three times with physiological saline, thus removing the surplus primer(s).

4. 1.6 mM magnesium sulfate, 0.2 mM dNTP, SYBR Green solution, 200 units of SuperScript III (Invitrogen), and 2 units of Platinum Taq DNA polymerase (Invitrogen) were mixed with a buffer solution for Platinum Taq. Thus, a reaction solution that allows both reverse transcription and PCR to be carried out therein was prepared. To this reaction solution, beta-actin messenger RNA was added so that the concentration thereof became 100 pM. To the chamber on the cover slip having the primer pair or only the forward primer as the negative control immobilized thereon, 25 µl of the reaction solution was added, and the chamber was closed with a cover film (TAKARA BIO INC., Takara Slide Seal for in situ PCR).

5. Each cover slip was placed in a reaction chamber of a GenePro Thermal Cycler (Bioer Technology Co., Ltd.) equipped with a GenePro Insitu "Japanese Version" B-4 block. The cover slip was heated at 55° C. for 30 minutes and at 94° C. for 4 minutes, and then was subjected to 40 cycles of the following thermal treatment: 94° C. for 1 minute, 60° C. for 1 minute, and 68° C. for 1 minute. Thereafter, the cover slip was incubated at 68° C. for 5 minutes to terminate the reaction.

6. The cover slip after the termination of the reaction was excited at an excitation wavelength of 470 nm using an Eclipse Ti fluorescence microscope (NIKON CORPORATION), and the fluorescence at 525 nm was observed.

Figure 15:
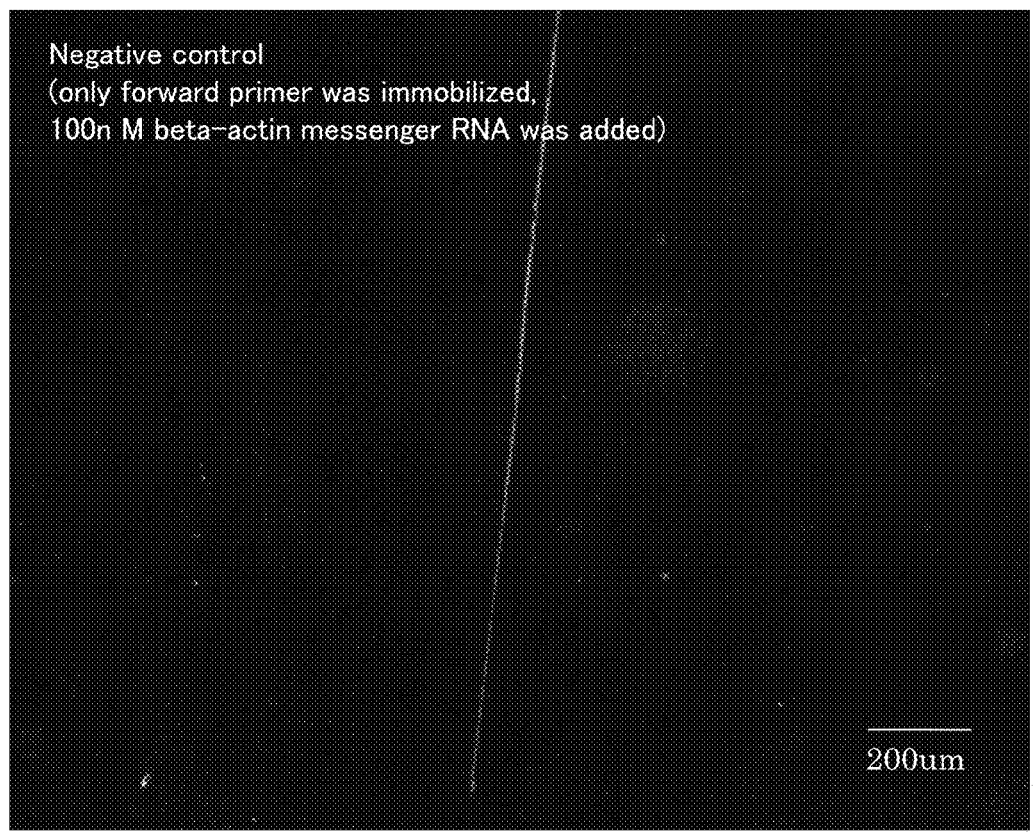
FIG. 15 is a photograph showing the result of observing a cover slip after bridge RT-PCR with a fluorescence microscope in Example 2-J.
Figure 16:
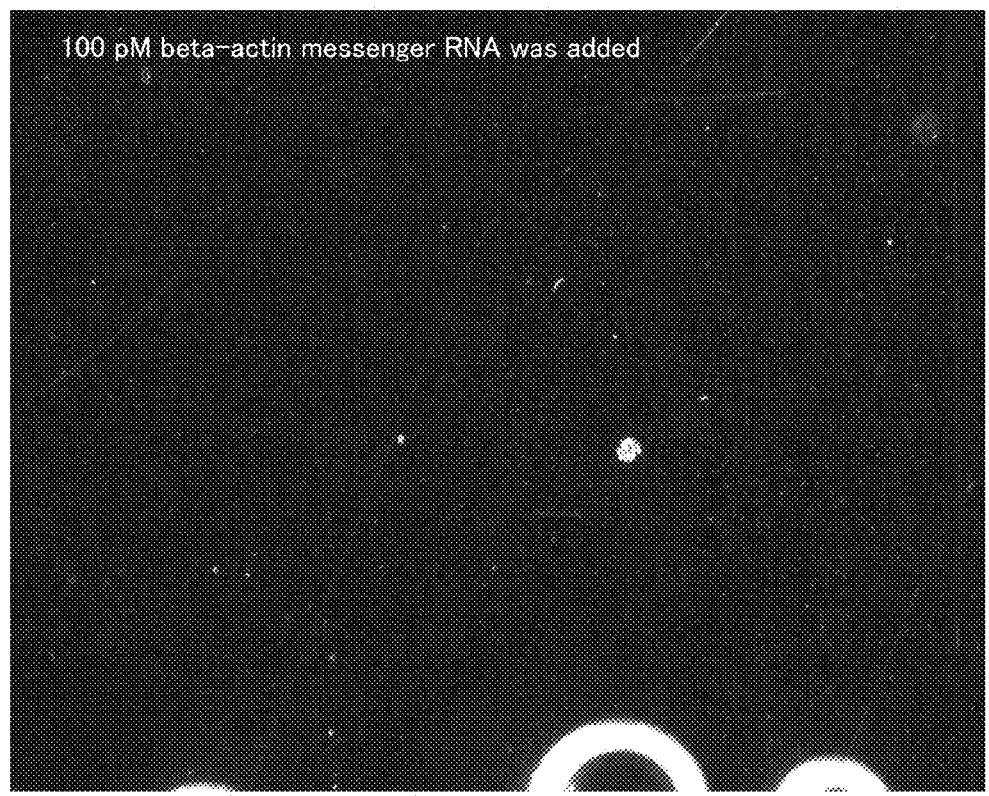
FIG. 16 is a photograph showing the result of observing another cover slip after bridge RT-PCR with a fluorescence microscope in Example 2-J.

FIGS. 15 and 16 are each a photograph showing the result of observing the cover slip after the bridge RT-PCR with the fluorescence microscope. FIG. 15 shows the result obtained regarding the negative control (only the forward primer was immobilized, the 100 nM beta-actin messenger RNA was added), and FIG. 16 shows the result obtained when the 100 pM beta-actin messenger RNA was added. As can be seen from FIGS. 15 and 16, fluorescent spots derived from the SYBR Green were observed only in the reaction chamber in which both the forward primer and the reverse primer were immobilized. From these results, it was found that the fluorescent spots were derived from the clusters of double-stranded DNA, which confirms that the bridge RT-PCR reaction system proceeds successfully when the immobilized primer pair is used.

Example 2-K: Experiment in which Beta-Actin Messenger RNA Molecules Obtained by Bridge RT-PCR Using an Immobilized Specific Primer Set were Counted (the Reproducibility of Checking as to the Concentration of Template Messenger RNA and Amplification)

1. Primers of the present example were synthesized by biotinylating the 5' ends of specific primers (Forward: 5'-AAA AAA AAA AGG CAT GGG TCA GAA GGA TT-3' (SEQ ID NO: 1), Reverse: 5'-AAA AAA AAA AAG GTG TGG TGC CAG ATT TTC-3' (SEQ ID NO: 2)).
2. An adhesive frame (TAKARA BIO INC., Takara Slide Seal for in situ PCR) was attached to a biotin-coated surface of a biotin-coated cover slip (Alliance Technology, Biotin/cover slip/Bio_02-C) to provide a reaction chamber. A 20 µg/ml streptavidin protein solution prepared using physiological saline containing glycerol was added to the chamber so that the biotin-coated surface of the cover slip in the chamber was entirely coated with the solution. In order to prevent the surface from being dried, the chamber was covered with the lid of a petri dish. The chamber was then allowed to stand at 37° C. for 30 minutes, thereby immobilizing the streptavidin protein on the surface of the cover slip. After the immobilization, the cover slip was washed three times with physiological saline, thus removing the surplus streptavidin protein. At this time, glycerol-containing physiological saline to which RNase-free water was added instead of streptavidin also was prepared, and this was added to a biotin-coated cover slip to provide a negative control.
3. Glycerol was added to physiological saline so that the concentration thereof became 10%. Then, two kinds of the primers, namely, the biotinylated forward primer and the biotinylated reverse primer, were added thereto so that the final concentration of each of these primers became 3.3 mol/l. To the reaction chamber on the streptavidin immobilized cover slip and to the chamber of the negative control, the biotinylated primer pair solution was added so that the surface of the cover slip in each chamber was entirely coated with the solution. In order to prevent the surface from being dried, the chamber was covered with the lid of a petri dish. The chamber then was allowed to stand at 37° C. for 30 minutes, thereby immobilizing the biotinylated primer pair. After the immobilization, the cover slip was washed three times with physiological saline, thus removing the surplus primers.
4. 1.6 mM magnesium sulfate, 0.2 mM dNTP, SYBR Green solution, 200 units of SuperScript III (Invitrogen), and 2 units of Platinum Taq DNA polymerase (Invitrogen) were mixed with a buffer solution for Platinum Taq. Thus, a reaction solution that allows both reverse transcription and PCR to be carried out therein was prepared. To this reaction solution, beta-actin messenger RNA was added so that the concentration thereof became 100 nM, 100 pM, or 100 fM. To the chamber on the cover slip having the primer pair immobilized thereon or to the chamber on the cover slip as the negative control, 25 µl of the reaction solution was added, and the chamber was closed with a cover film (TAKARA BIO INC., Takara Slide Seal for in situ PCR).
5. Each cover slip was placed in a reaction chamber of a GenePro Thermal Cycler (Bioer Technology Co., Ltd.) equipped with a GenePro Insitu "Japanese Version" B-4 block. The cover slip was heated at 55° C. for 30 minutes and at 94° C. for 4 minutes, and then was subjected to 40 cycles of the following thermal treatment: 94° C. for 1 minute, 60° C. for 1 minute, and 68° C. for 1 minute. Thereafter, the cover slip was incubated at 68° C. for 5 minutes to terminate the reaction.
6. The cover slip after the termination of the reaction was excited at an excitation wavelength of 470 nm using an Eclipse Ti fluorescence microscope (NIKON CORPORATION), and the fluorescence at 525 nm was observed.

Figure 17:
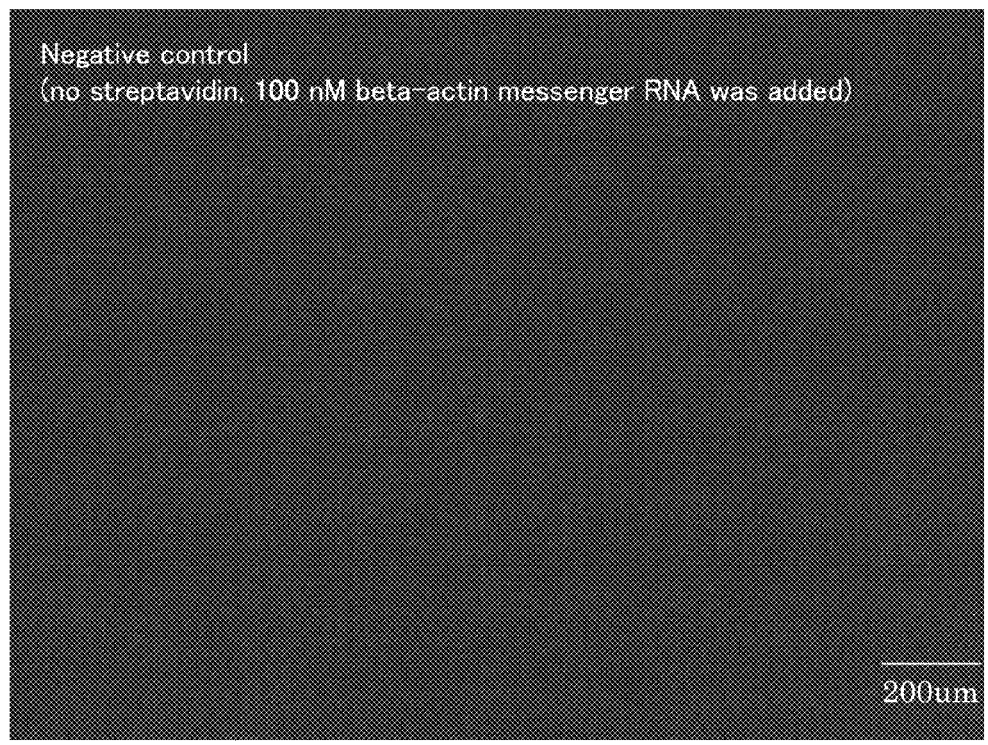
FIG. 17 is a photograph showing the result of observing a cover slip after bridge RT-PCR (the concentration of messenger RNA) with a fluorescence microscope in Example 2-K.
Figure 18:
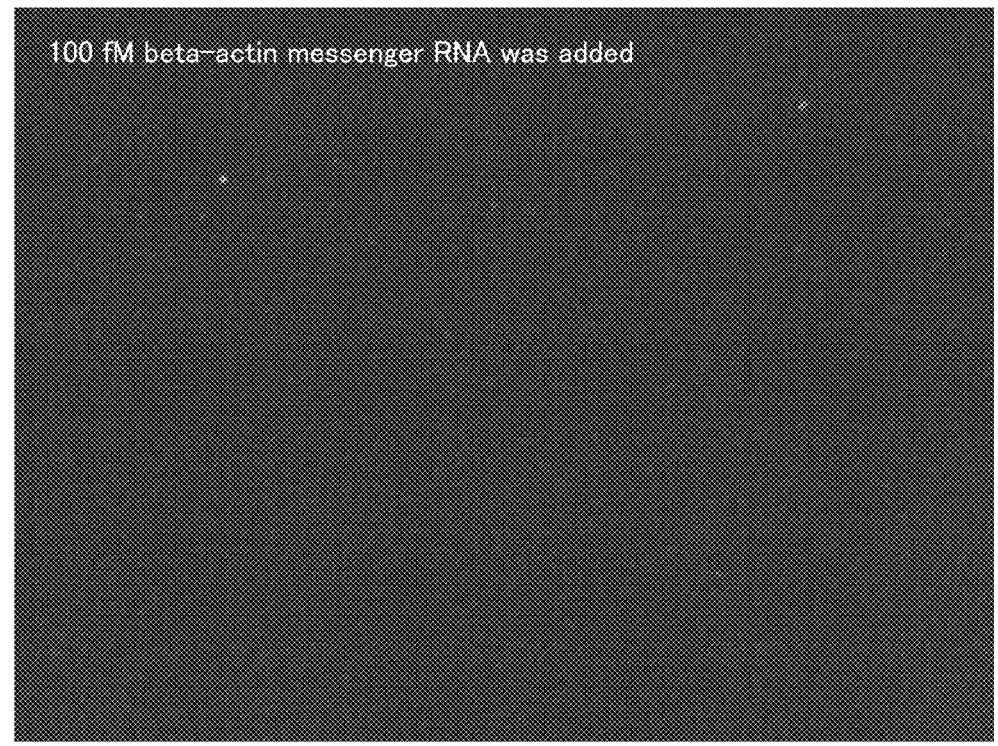
FIG. 18 is a photograph showing the result of observing another cover slip after bridge RT-PCR (the concentration of messenger RNA) with a fluorescence microscope in Example 2-K.
Figure 19:
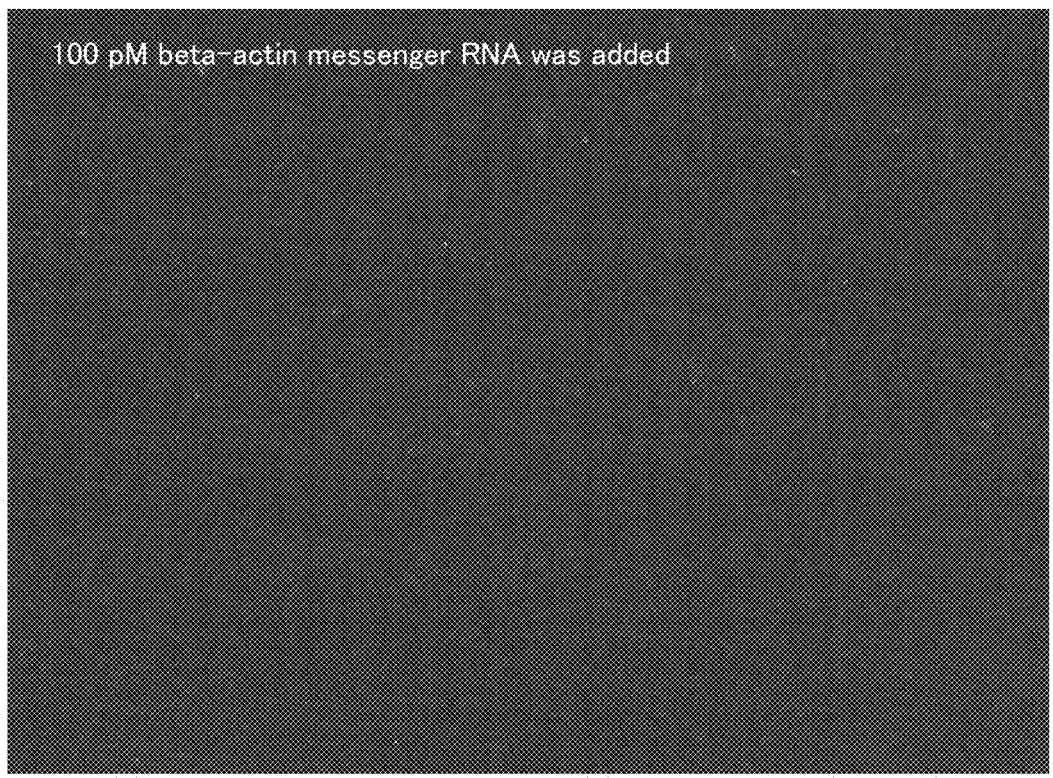
FIG. 19 is a photograph showing the result of observing still another cover slip after bridge RT-PCR (the concentration of messenger RNA) with a fluorescence microscope in Example 2-K.
Figure 20:
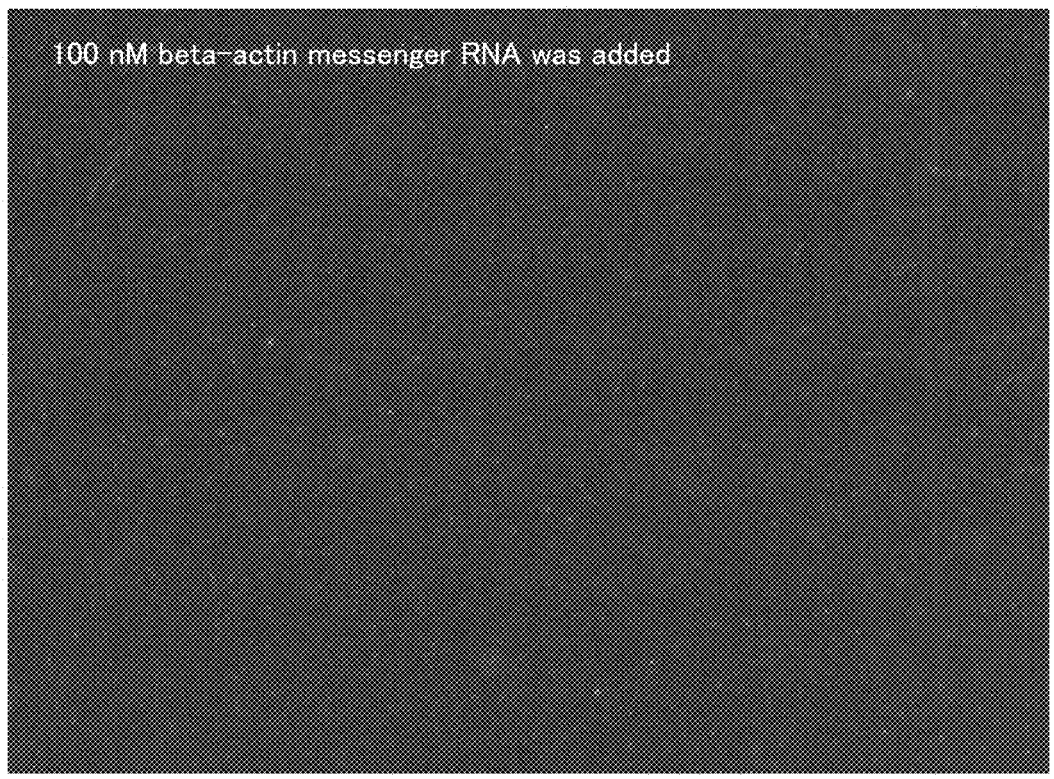
FIG. 20 is a photograph showing the result of observing yet another cover slip after bridge RT-PCR (the concentration of messenger RNA) with a fluorescence microscope in Example 2-K.

FIGS. 17, 18, 19, and 20 are each a photograph showing the result of observing the cover slip after the bridge RT-PCR with the fluorescence microscope (the concentration of the messenger RNA). FIG. 17 shows the result obtained regarding the negative control (no streptavidin, the 100 nM beta-actin messenger RNA was added); FIG. 18 shows the result obtained when the 100 fM beta-actin messenger RNA was added; FIG. 19 shows the result obtained when the 100 pM beta-actin messenger RNA was added; and FIG. 20 shows the result obtained when the 100 nM beta-actin messenger RNA was added. As can be seen from FIGS. 17, 18, 19, and 20, the number of fluorescent spots derived from the SYBR Green increased in keeping with the increase in the added amount of the beta-actin messenger RNA (100 fM, 100 pM, and 100 nM).

(Example 2-L: Experiment in which Beta-Actin Messenger RNA Molecules Obtained by Bridge RT-PCR Using an Immobilized Specific Primer Set were Counted (the Number of PCR Cycles))

1. Primers of the present example were synthesized by biotinylating the 5' ends of specific primers (Forward: 5'-AAA AAA AAA AGG CAT GGG TCA GAA GGA TT-3' (SEQ ID NO: 1), Reverse: 5'-AAA AAA AAA AAG GTG TGG TGC CAG ATT TTC-3' (SEQ ID NO: 2)).
2. An adhesive frame (TAKARA BIO INC., Takara Slide Seal for in situ PCR) was attached to a biotin-coated surface of a biotin-coated cover slip (Alliance Technology, Biotin/cover slip/Bio_02-C) to provide a reaction chamber. A 20 µg/ml streptavidin protein solution prepared using physiological saline containing glycerol was added to the chamber so that the biotin-coated surface of the cover slip in the chamber was entirely coated with the solution. In order to prevent the surface from being dried, the chamber was covered with the lid of a petri dish. The chamber was then allowed to stand at 37° C. for 30 minutes, thereby immobilizing the streptavidin protein on the surface of the cover slip. After the immobilization, the cover slip was washed three times with physiological saline, thus removing the surplus streptavidin protein.
3. Glycerol was added to physiological saline so that the concentration thereof became 10%. Then, two kinds of the primers, namely, the biotinylated forward primer and the biotinylated reverse primer, were added thereto so that the final concentration of each of these primers became 3.3 mol/l, or alternatively, as a negative control, only the forward primer was added thereto so that the final concentration of the forward primer became 6.6 µmol/l. To the reaction chamber on the streptavidin immobilized cover slip, the biotinylated primer pair solution or the biotinylated forward primer solution as the negative control was added so that the surface of the cover slip in the chamber was entirely coated with the solution. In order to prevent the surface from being dried, the chamber was covered with the lid of a petri dish. The chamber then was allowed to stand at 37° C. for 30 minutes, thereby immobilizing the biotinylated primer pair or the biotinylated forward primer as the negative control. After the immobilization, the cover slip was washed three times with physiological saline, thus removing the surplus primer(s).

4. 1.6 mM magnesium sulfate, 0.2 mM dNTP, SYBR Green solution, 200 units of SuperScript III (Invitrogen), and 2 units of Platinum Taq DNA polymerase (Invitrogen) were mixed with a buffer solution for Platinum Taq. Thus, a reaction solution that allows both reverse transcription and PCR to be carried out therein was prepared. To this reaction solution, beta-actin messenger RNA was added so that the concentration thereof became 100 pM. To the chamber on the cover slip having the primer pair immobilized thereon or the chamber on the cover slip as the negative control, 25 µl of the reaction solution was added, and the chamber was closed with a cover film (TAKARA BIO INC., Takara Slide Seal for in situ PCR).

5. Each cover slip was placed in a reaction chamber of a GenePro Thermal Cycler (Bioer Technology Co., Ltd.) equipped with a GenePro Insitu "Japanese Version" B-4 block. The cover slip was heated at 55° C. for 30 minutes and at 94° C. for 4 minutes, and then was subjected to 10, 20, 30, or 40 cycles of the following thermal treatment to allow the reaction to proceed: at 94° C. for 1 minute, 60° C. for 1 minute, and 68° C. for 1 minute.

6. After the completion of each series of cycles, the cover slip was taken out, and refrigerated at 4° C. under light-shielding conditions. The cover slip was excited at an excitation wavelength of 470 nm using an Eclipse Ti fluorescence microscope (NIKON CORPORATION), and the fluorescence at 525 nm was observed.

Figure 21:
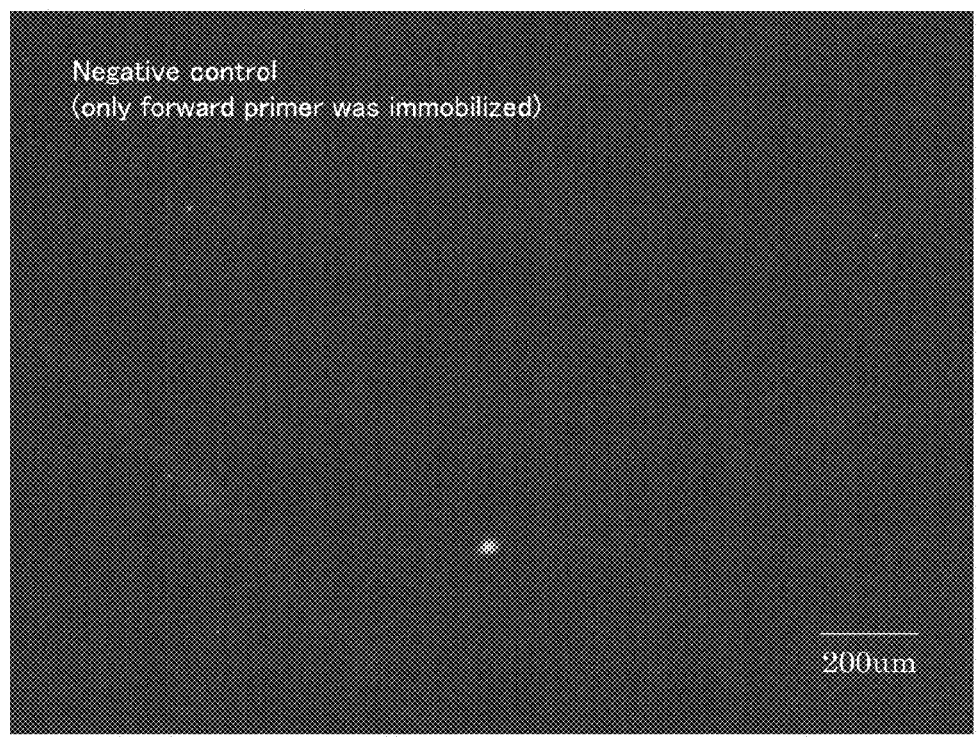
FIG. 21 is a photograph showing the result of observing a cover slip after bridge RT-PCR (the number of PCR cycles) with a fluorescence microscope in Example 2-L.
Figure 22:
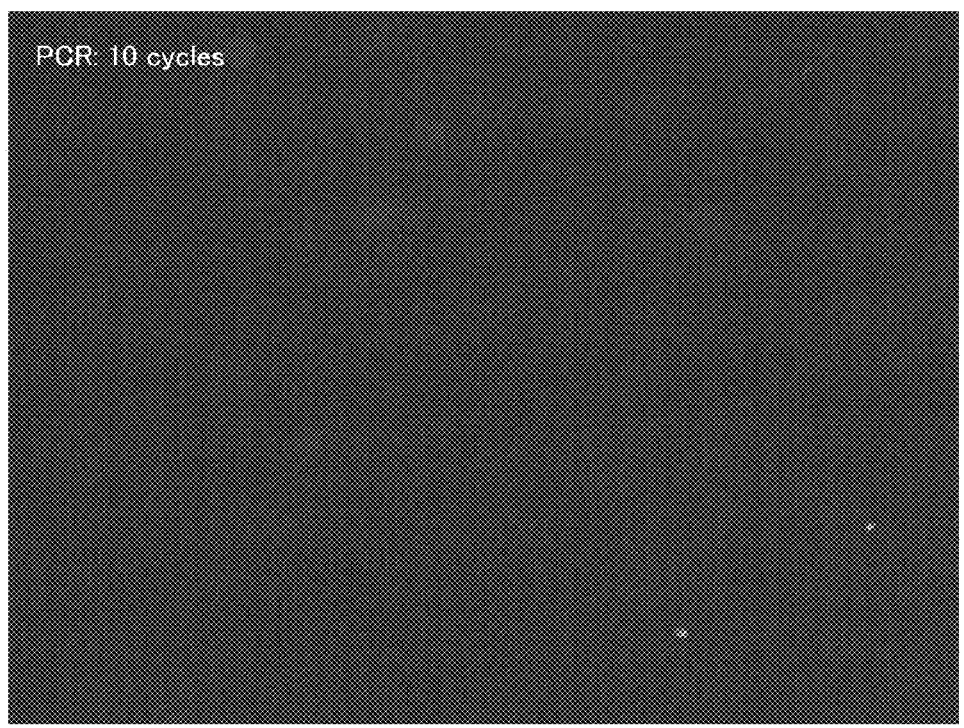
FIG. 22 is a photograph showing the result of observing another cover slip after bridge RT-PCR (the number of PCR cycles) with a fluorescence microscope in Example 2-L.
Figure 23:
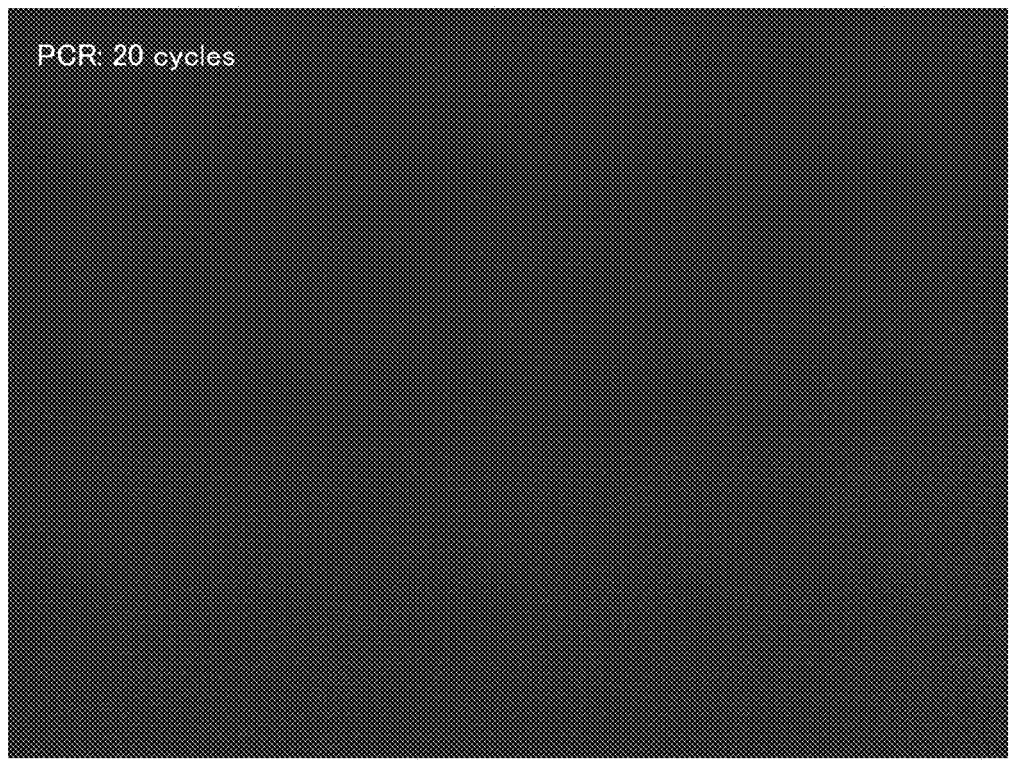
FIG. 23 is a photograph showing the result of observing still another cover slip after bridge RT-PCR (the number of PCR cycles) with a fluorescence microscope in Example 2-L.
Figure 24:
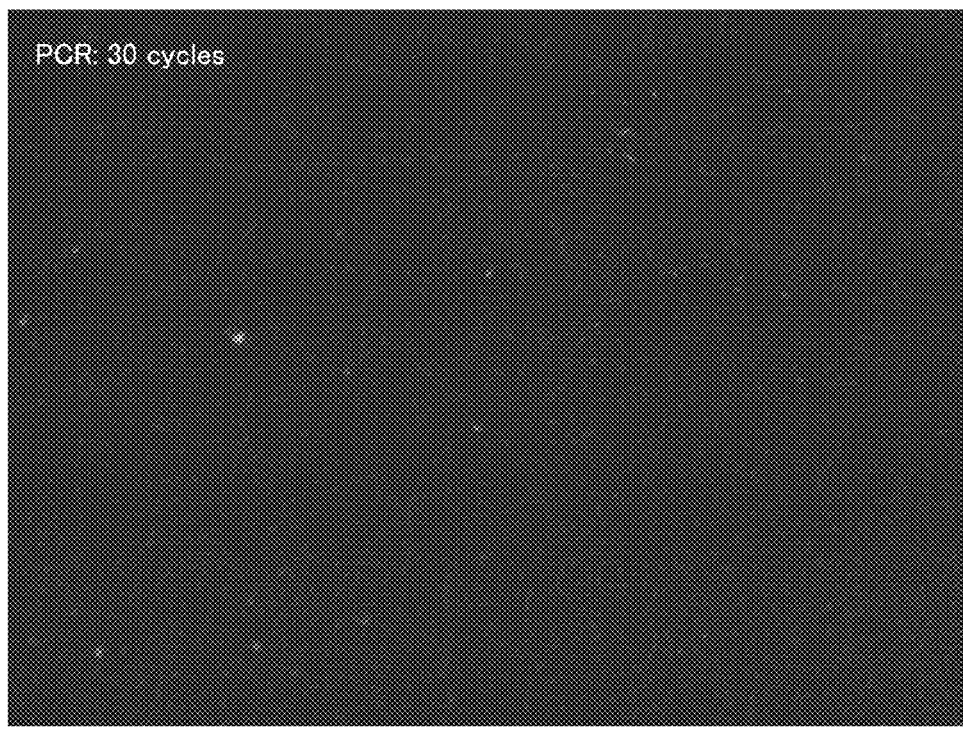
FIG. 24 is a photograph showing the result of observing yet another cover slip after bridge RT-PCR (the number of PCR cycles) with a fluorescence microscope in Example 2-L.
Figure 25:
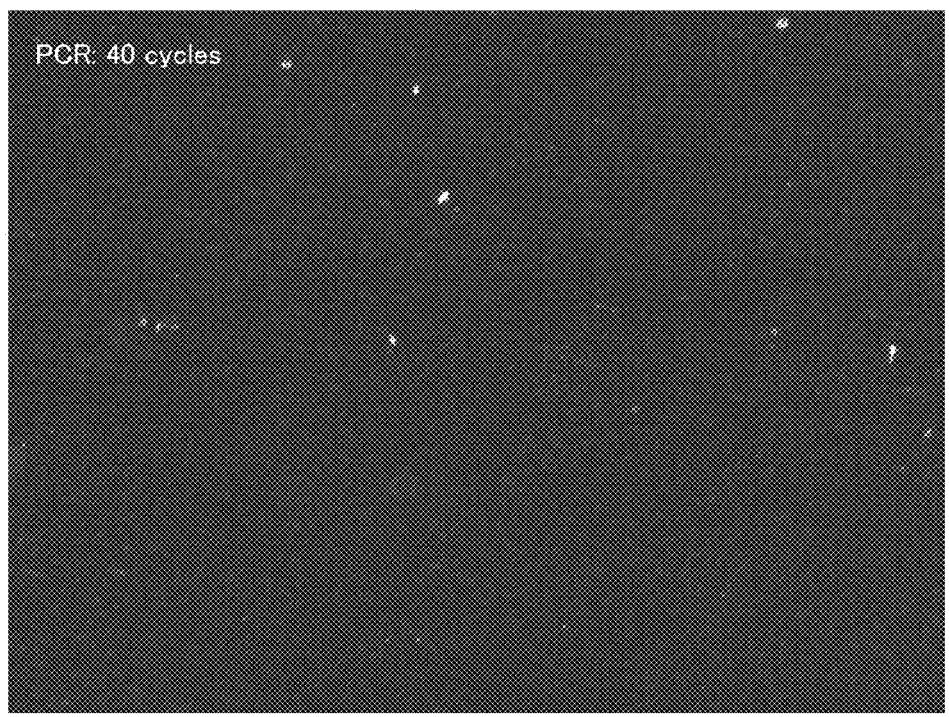
FIG. 25 is a photograph showing the result of observing yet another cover slip after bridge RT-PCR (the number of PCR cycles) with a fluorescence microscope in Example 2-L.

FIGS. 21, 22, 23, 24, and 25 are each a photograph showing the result of observing the cover slip after the bridge RT-PCR with the fluorescence microscope (the number of PCR cycles). FIG. 21 shows the result obtained regarding the negative control (only the forward primer was immobilized); FIG. 22 shows the result obtained when the number of PCR cycles was 10; FIG. 23 shows the result obtained when the number of PCR cycles was 20; FIG. 24 shows the result obtained when the number of PCR cycles was 30; and FIG. 25 shows the result obtained when the number of PCR cycles was 40. When the number of PCR cycles was up to 20 cycles, formation of DNA clusters by the bridge PCR was not observed by the observation method employed in the present experiment. When the number of PCR cycles was 30 or more, DNA clusters were observed.

Example 2-M: Experiment in which Beta-Actin Messenger RNA Molecules Obtained by Bridge RT-PCR Using an Immobilized Specific Primer Set Labeled with Fluorescent Dyes that Exhibits Self-Fluorescence Emission/Self-Quenching were Counted 1. As fluorescent primers that exhibit self-fluorescence emission/self-quenching (exciton primers, S. Ikeda, A. Okamoto, Chem. Asian J. 2008, 3, 958-968.), ACTB-5'F_ExS (5'-GGCATGGGT*CAGAAGGATT-3', with the 5'-end being biotinylated: SEQ ID NO: 11) and ACTB-5'R ExS (5'-AGGTGTGGT*GCCAGATTTTC-3', with the 5'-end being biotinylated: SEQ ID NO: 12) were produced (the position indicated with "T*" is fluorescently labeled).

2. An adhesive frame (TAKARA BIO INC., Takara Slide Seal for in situ PCR) was attached to a biotin-coated surface of a biotin-coated cover slip (Alliance Technology, Biotin/cover slip/Bio_02-C) to provide a reaction chamber. A 20 µg/ml streptavidin protein solution prepared using physiological saline containing glycerol was added to the chamber so that the biotin-coated surface of the cover slip in the chamber was entirely coated with the solution. In order to prevent the surface from being dried, the chamber was covered with the lid of a petri dish. The chamber was then allowed to stand at 37° C. for 30 minutes, thereby immobilizing the streptavidin protein on the surface of the cover slip. After the immobilization, the cover slip was washed three times with physiological saline, thus removing the surplus streptavidin protein.

3. Glycerol was added to physiological saline so that the concentration thereof became 10%. Then, two kinds of the primers, namely, the biotinylated exciton forward primer and the biotinylated exciton reverse primer, were added thereto so that the final concentration of each of these primers became 3.3 µmol/l, or alternatively, as a negative control, only the forward primer was added thereto so that the final concentration of the forward primer became 6.6 µmol/l. To the reaction chamber on the streptavidin immobilized cover slip, the biotinylated primer pair solution or the biotinylated forward primer solution as the negative control was added so that the surface of the cover slip in the chamber was entirely coated with the solution. In order to prevent the surface from being dried, the chamber was covered with the lid of a petri dish. The chamber then was allowed to stand at 37° C. for 30 minutes, thereby immobilizing the biotinylated exciton primer pair or the biotinylated exciton forward primer as the negative control. After the immobilization, the cover slip was washed three times with physiological saline, thus removing the surplus primer(s).

4. 1.6 mM magnesium sulfate, 0.2 mM dNTP, 200 units of SuperScript III (Invitrogen), and 2 units of Platinum Taq DNA polymerase (Invitrogen) were mixed with a buffer solution for Platinum Taq. Thus, a reaction solution that allows both reverse transcription and PCR to be carried out therein was prepared. To this reaction solution, beta-actin messenger RNA was added so that the concentration thereof became 100 pM. To the chamber on the cover slip having the primer pair immobilized thereon or the chamber on the cover slip as the negative control, 25 µl of the reaction solution was added, and the chamber was closed with a cover film (TAKARA BIO INC., Takara Slide Seal for in situ PCR).

5. Each cover slip was placed in a reaction chamber of a GenePro Thermal Cycler (Bioer Technology Co., Ltd.) equipped with a GenePro Insitu "Japanese Version" B-4 block. The cover slip was heated at 55° C. for 30 minutes and at 94° C. for 4 minutes, and then was subjected to 40 cycles of the following thermal treatment to allow the reaction to proceed: 94° C. for 1 minute, 60° C. for 1 minute, and 68° C. for 1 minute. Thereafter, the cover slip was incubated at 68° C. for 5 minutes to terminate the reaction.

6. The cover slip after the termination of the reaction was excited at an excitation wavelength of 470 nm using an Eclipse Ti fluorescence microscope (NIKON CORPORATION), and the fluorescence at 520 nm was observed.

Figure 26:
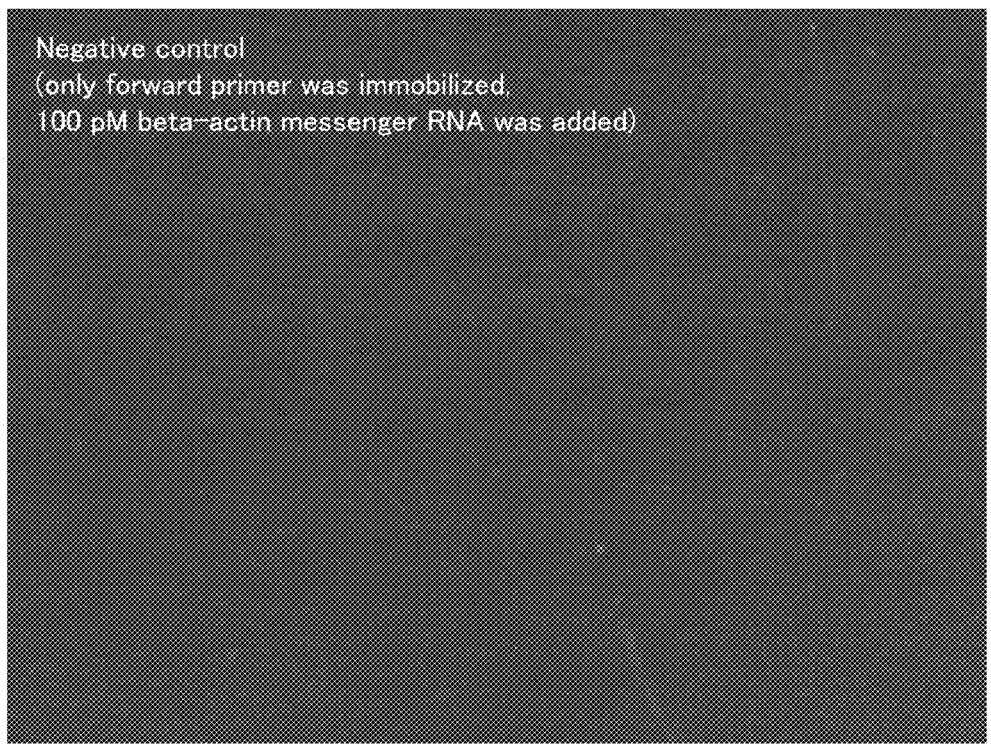
FIG. 26 is a photograph showing the result of bridge RT-PCR using a fluorescently labeled immobilized specific primer set in Example 2-M.
Figure 27:
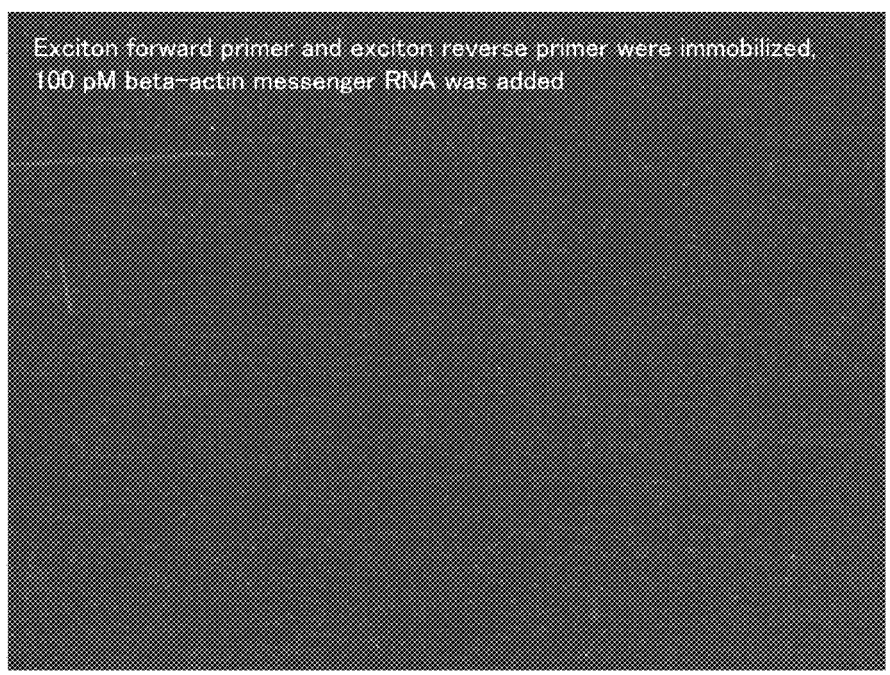
FIG. 27 is a photograph showing the result of bridge RT-PCR using a fluorescently labeled immobilized specific primer set in Example 2-M.
Figure 28:
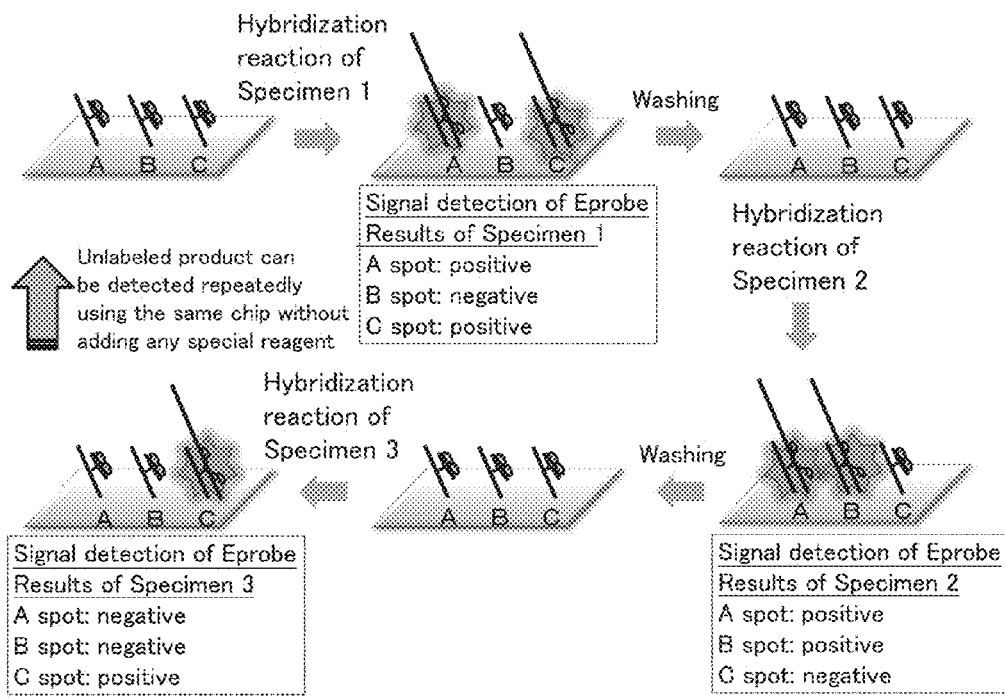
FIG. 28 is a schematic view showing an example of the use of an Eprobe. By causing hybridization of an Eprobe with a specimen sample on a microarray having the Eprobe immobilized thereon and then detecting a fluorescent signal, the presence or absence of a target product or the presence or absence of a mutation is determined. By washing the microarray, it becomes possible to perform the detection of this kind using the same microarray. Thus, the microarray can be used repeatedly without any special modification to a specimen sample, and further, without requiring any particular color-developing enzyme reaction after hybridization.
Figure 29:
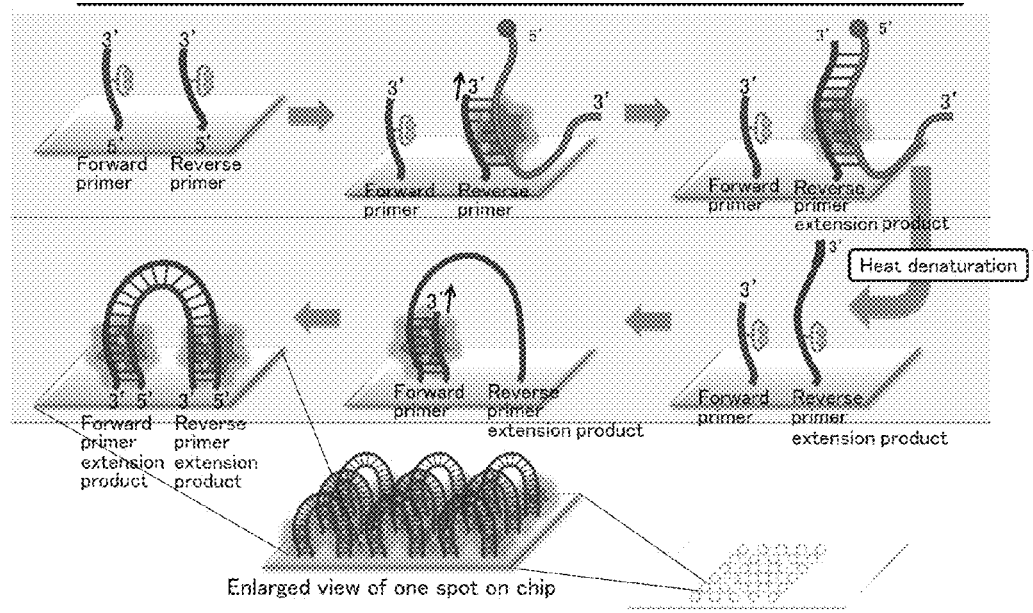
FIG. 29 is a schematic view showing an example where an Eprimer is used in bridge PCR. By annealing an Eprimer to a specimen sample on a microarray having the Eprimer immobilized thereon to carry out bridge PCR and then detecting a fluorescent signal, the presence or absence of a target product or the presence or absence of a mutation is determined.

FIGS. 26 and 27 are each a photograph showing the result of the bridge RT-PCR using the fluorescently labeled immobilized specific primer set. FIG. 26 shows the result obtained regarding the negative control (only the forward primer was immobilized, the 100 pM beta-actin messenger RNA was added); and FIG. 27 shows the result obtained when the exciton forward primer and the exciton reverse primer were immobilized, and the 100 pM beta-actin messenger RNA was added. When RT-PCR was carried out with both the forward and reverse fluorescent primers (exciton primers) that exhibit self-fluorescence emission upon DNA double-strand formation being immobilized, fluorescent spots derived from DNA clusters were observed after the RT-PCR, as in the case where SYBR Green was used.

INDUSTRIAL APPLICABILITY

As specifically described above, according to the method, kit, and analyzer for analyzing a target nucleic acid according to the present invention, the target nucleic acid can be analyzed rapidly and easily. The present invention provides, for example: a composition for prediction, determination, detection, or diagnosis, useful in the prediction, determination, detection, or diagnosis of physical conditions and the prognosis of various diseases; a method for predicting, determining, detecting, or diagnosing physical conditions and the prognosis of various diseases utilizing the composition; and a kit and device for predicting, determining, detecting, or diagnosing physical conditions and the prognosis of various diseases utilizing the composition. Thus, according to the present invention, highly precise results can be obtained in tests, diagnosis, etc. of diseases in medical fields, for example. Hence, the present invention is industrially useful.

The invention claimed is:

1. A method for analyzing a target nucleic acid in a sample, the method comprising the step of:

analyzing the target nucleic acid in the sample by bringing the sample into contact with a label and with a primer that can hybridize to the target nucleic acid, wherein the primer is immobilized on a solid phase, and the primer is a nucleic acid molecule comprising at least one of structures represented by the following formulae (16), (16b), (17), (17b), (18), and (18b), the label is covalently bound to the primer so as to be part of the primer, the label is a fluorescent dye moiety that exhibits an exciton effect, and the label does not emit light when the primer does not hybridize to the target nucleic acid, whereas the label emits light when the primer has hybridized to the target nucleic acid, the analysis is carried out by detecting light emission from the label caused by hybridization of the primer with the target nucleic acid, the target nucleic acid that has hybridized with the primer is removed by washing, the primer is hybridized again with another target nucleic acid, and the analysis is carried out again by detecting light emission from the label, the primer is hybridized to the target nucleic acid by bringing the primer into contact with the sample, thereby causing an amplification reaction of the target nucleic acid, and the analysis of the target nucleic acid is carried out by further measuring the degree of amplification of the target nucleic acid in the amplification reaction over time:

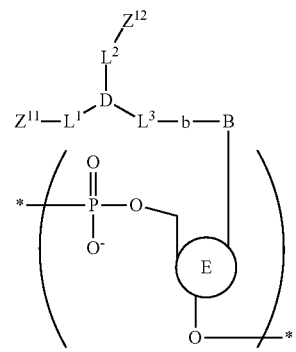
(16)

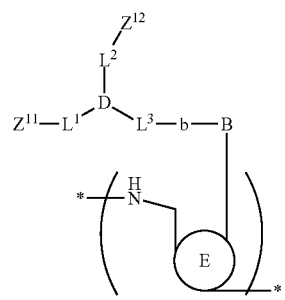
(16b)

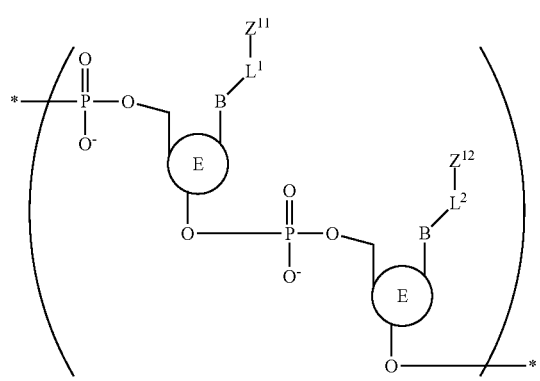
(17)

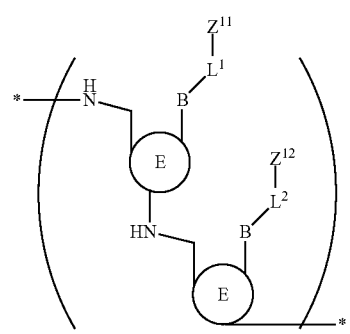
(17b)

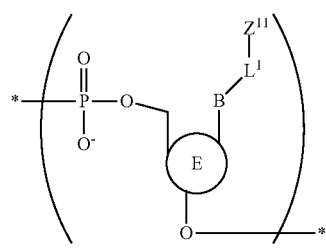
(18)

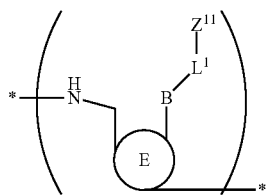

(18b)

where in the formulae (16), (16b), (17), (17b), (18), and (18b),
B is an atomic group having a natural nucleobase (adenine, guanine, cytosine, thymine, or uracil) skeleton or an artificial nucleobase skeleton,
E is:
(i) an atomic group having a deoxyribose skeleton, a ribose skeleton, or a structure derived from either one of them; or
(ii) an atomic group having a peptide structure or a peptoid structure,
$Z^{11}$ and $Z^{12}$ are each the fluorescent dye moiety that exhibits an exciton effect, and may be identical to or different from each other,
$L^1$, $L^2$, and $L^3$ are each a linker (a linking atom or a linking atomic group), the main chain length (the number of main chain atoms) thereof is arbitrary, $L^1$, $L^2$, and $L^3$ each may or may not contain each of C, N, O, S, P, and Si in the main chain, $L^1$, $L^2$, and $L^3$ each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from each other,
D is CR, N, P, P=O, B, or SiR, and R is a hydrogen atom, an alkyl group, or an arbitrary substituent, and
b is a single bond, a double bond, or a triple bond, or alternatively,
in the formulae (16) and (16b), $L^1$ and $L^2$ are each the linker, $L^3$, D, and b may not be present, and $L^1$ and $L^2$ may be bonded directly to B, provided that:
in the formulae (16), (17), and (18), E is an atomic group described in the item (i), and at least one O atom in a phosphoric acid linkage may be substituted with an S atom;
in the formulae (16b), (17b), and (18b), E is an atomic group described in the item (ii); and
in the formulae (17) and (17b), the respective Bs may be identical to or different from each other, and the respective Es may be identical to or different from each other.

2. The method according to claim 1, wherein
there are two or more kinds of the target nucleic acids, and the respective target nucleic acids are detected separately.

3. The method according to claim 1, wherein
two or more kinds of the primers are used.

4. The method according to claim 1, wherein
a surface of the solid phase on which the primer is immobilized is a flat surface, a flat chip surface, a spherical surface, or a three-dimensional surface.

5. The method according to claim 1, wherein
a surface of the solid phase is coated with a coating for reducing a background.

6. The method according to claim 5, wherein
the coating for reducing a background is provided by graft polymerization.

7. The method according to claim 1, wherein
in the formulae (16), (17), (16b), (17b), (18), and (18b), the main chain length (the number of main chain atoms) of each of $L^1$, $L^2$, and $L^3$ is an integer of 2 or more.

8. The method according to claim 1, wherein
in the formulae (16), (17), (16b), (17b), (18), and (18b), $Z^{11}$ and $Z^{12}$ are each independently a group derived from any one of thiazole orange, oxazole yellow, cyanine, hemicyanine, other cyanine dyes, methyl red, azo dyes, biotin, and derivatives thereof.

9. The method according to claim 1, wherein
$Z^{11}$ and $Z^{12}$ are each independently an atomic group represented by any one of the following formulae (7) to (9):

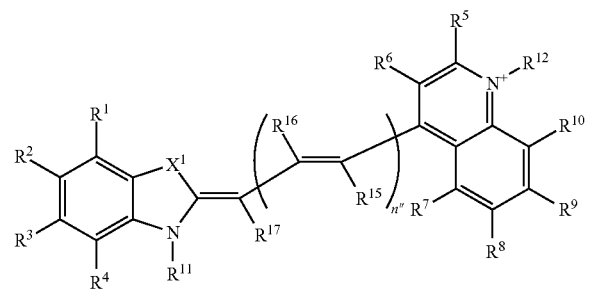

(7)

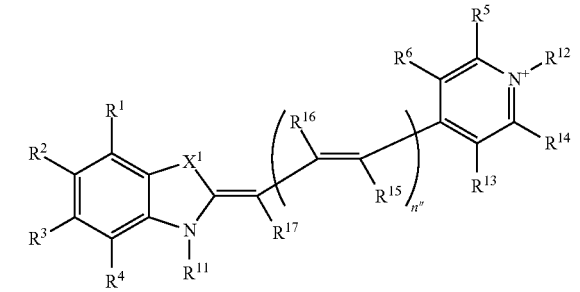

(8)

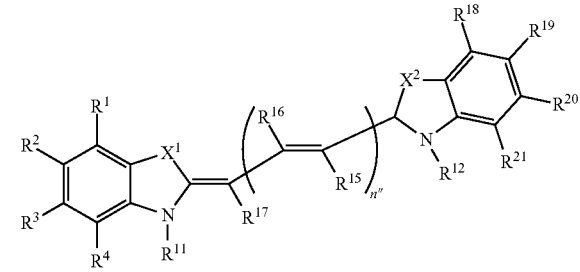

(9)

where in the formulae (7) to (9),
$X^1$ and $X^2$ are S, O, or Se,
$n''$ is 0 or a positive integer,
$R^1$ to $R^{10}$ and $R^{13}$ to $R^{21}$ are each independently a hydrogen atom, a halogen atom, a lower alkyl group, a lower alkoxy group, a nitro group, or an amino group,
one of $R^{11}$ and $R^{12}$ is a linking group that is bound to $L^1$ or $L^2$ in the formulae (16), (17), (16b), and (17b), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively.

10. The method according to claim 9, wherein
in the formulae (7) to (9),
in $R^1$ to $R^{21}$, the lower alkyl group is a linear or branched alkyl group with a carbon number of 1 to 6, and the lower alkoxy group is a linear or branched alkoxy group with a carbon number of 1 to 6.

11. The method according to claim 9, wherein
in the formulae (7) to (9),
in $R^{11}$ and $R^{12}$, the linking group is a polymethylene carbonyl group with a carbon number of 2 or more and is bound to $L^1$ or $L^2$ in the formulae (16), (16b), (17), and (17b) in a carbonyl group moiety.

12. The method according to claim 9, wherein
$Z^{11}$ and $Z^{12}$ are each independently an atomic group represented by the formula (7) or (8), and
$Z^{11}$ and $Z^{12}$ represented by the formula (7) or (8) is a group represented by the following formula (19) or (20):

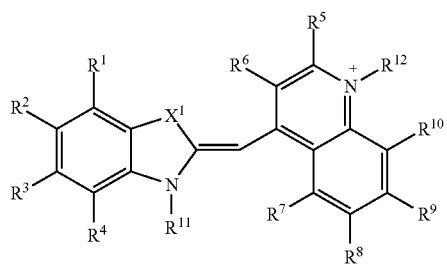
(19)

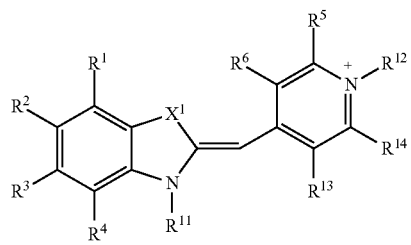
(20)

where in the formulae (19) and (20),
$X^1$, $R^1$ to $R^{10}$, $R^{13}$ and $R^{14}$, and $R^{11}$ and $R^{12}$ are identical to those in the formulae (7) to (9).

13. The method according to claim 12, wherein
$Z^{11}$ and $Z^{12}$ are each independently an atomic group represented by the above formula (19),
where in the formula (19),
$X^1$ is S,
$R^1$ to $R^{10}$ are hydrogen atoms, and
one of $R^{11}$ and $R^{12}$ is a linking group that is bound to $L^1$ or $L^2$ in the formulae (16), (17), (16b), and (17b), and the other is a methyl group.

14. The method according to claim 12, wherein
$Z^{11}$ and $Z^{12}$ are each independently an atomic group represented by the above formula (19), where in the formula (19),
$X^1$ is S,
$R^1$, $R^4$, $R^5$, $R^6$, $R^7$, $R^9$, and $R^{10}$ are hydrogen atoms,
$R^2$, $R^3$, and $R^{12}$ are methyl groups,
$R^8$ is a halogen atom, and
$R^{11}$ is a linking group that is bound to $L^1$ or $L^2$ in the formulae (16), (17), (16b), (17b), (18), and (18b).

15. The method according to claim 9, wherein
$Z^{11}$ and $Z^{12}$ are each independently an atomic group represented by the above formula (7),
where in the formula (7),
$X^1$ is S,
n" is 1,
$R^1$ to $R^{10}$, $R^{15}$, $R^{16}$, and $R^{17}$ are hydrogen atoms,
$R^{11}$ is a linking group that is bound to $L^1$ or $L^2$ in the formulae (16), (17), (16b), (17b), (18), and (18b), and
$R^{12}$ is a methyl group.

16. The method according to claim 9, wherein
$Z^{11}$ and $Z^{12}$ are each independently an atomic group represented by any one of the following formulae:

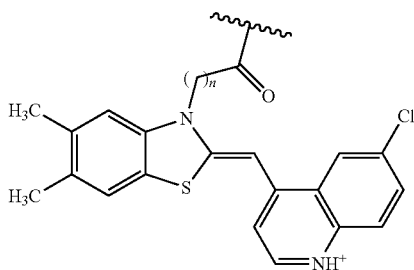

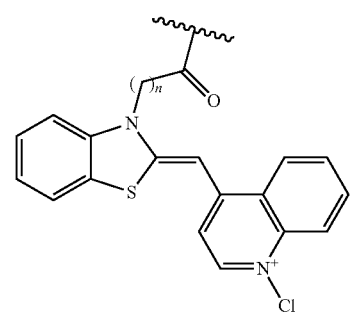

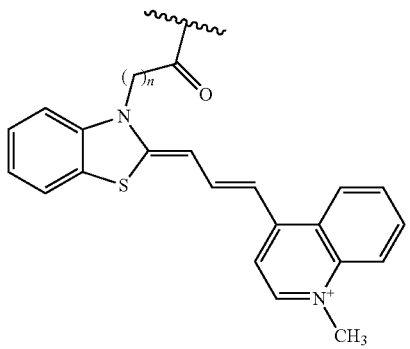

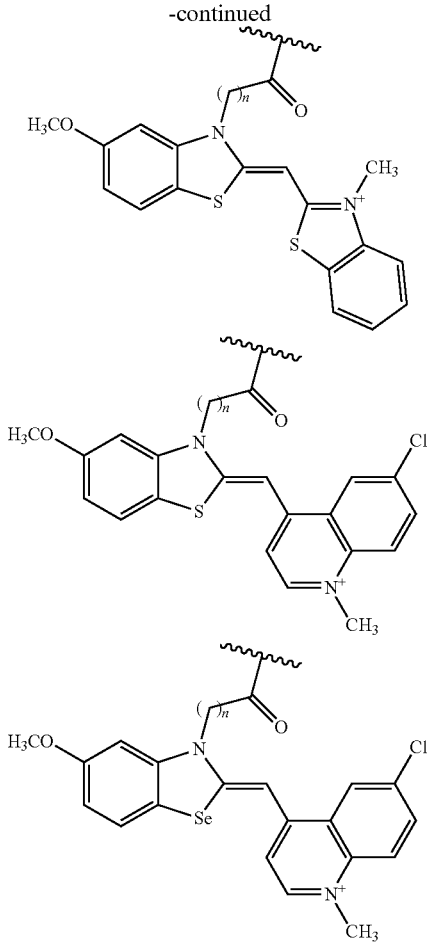

where in each of the above chemical formulae,
n is a positive integer.

17. The method according to claim 1, wherein
in the formulae (16), (17), (16b), (17b), (18), and (18b),
B is an atomic group having a natural nucleobase (adenine, guanine, cytosine, thymine, or uracil) skeleton.

18. The method according to claim 1, wherein
in the formulae (16), (17), (16b), (17b), (18), and (18b),
B is an atomic group having an artificial nucleobase skeleton, and the artificial nucleobase is 2-amino-6-(N,N-dimethylamino)purine pyridin-2-one, 5-methylpyridin-2-one, 2-amino-6-(2-thienyl)purine, pyrrole-2-carbaldehyde, 9-methylimidazo[(4,5)-b]pyridine, 5-iodo-2-oxo(1H)pyridine 2-oxo-(1H)pyridine, 2-amino-6-(2-thiazolyl)purine, 7-(2-thienyl)-imidazo[4,5-b]pyridine, bromothymine, azaadenine, or azaguanine.

19. The method according to claim 1, wherein
in the formulae (16), (17), (16b), (17b), (18), and (18b),
B is an atomic group having an artificial nucleobase skeleton, and the artificial nucleobase is Py, Py der., Pu, or Pu der.,
the Py is an atomic group having a covalent bond to E in the 1-position and a covalent bond to a linker moiety in the 5-position in a six-membered ring represented by the following formula (11):

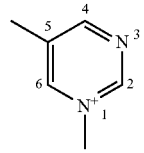

(11)

the Py der. is an atomic group in which at least one of all the atoms of the six-membered ring of the Py has been substituted with an N, C, S, or O atom, and the N, C, S, or O atom optionally may have an electric charge, a hydrogen atom, or a substituent,
the Pu is an atomic group having a covalent bond to E in the 9-position and a covalent bond to a linker moiety in the 8-position in a condensed ring represented by the following formula (12):

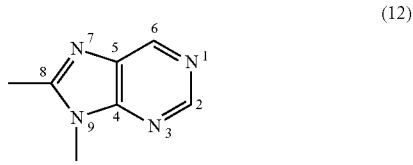

(12)

and the Pu der. is an atomic group in which at least one of all the atoms of a five-membered ring of the Pu has been substituted with an N, C, S, or O atom, and the N, C, S, or O atom optionally may have an electric charge, a hydrogen atom, or a substituent.

20. The method according to claim 1, wherein
the structure represented by the formula (16) is a structure represented by the following formula (16-1) or (16-2),
the structure represented by the formula (16b) is a structure represented by the following formula (16b-1) or (16b-2),
the structure represented by the formula (17) is a structure represented by the following formula (17-1),
the structure represented by the formula (17b) is a structure represented by the following formula (17b-1)
the structure represented by the formula (18) is a structure represented by the following formula (18-1), and
the structure represented by the formula (18b) is a structure represented by the following formula (18b-1):

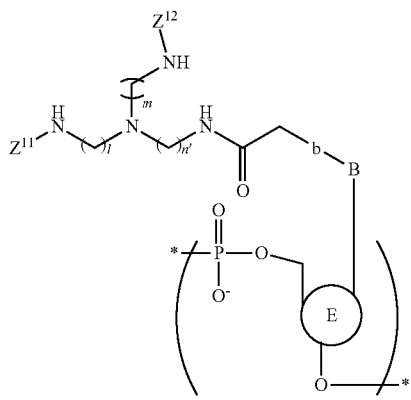

(16-1)

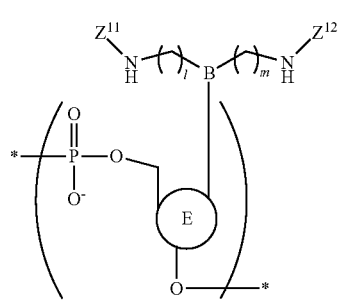

(16-2)

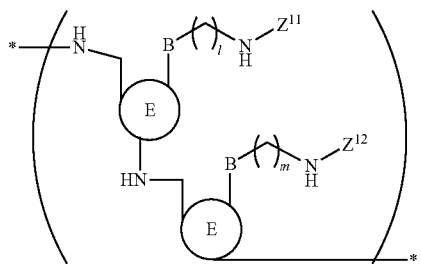

(17b-1)

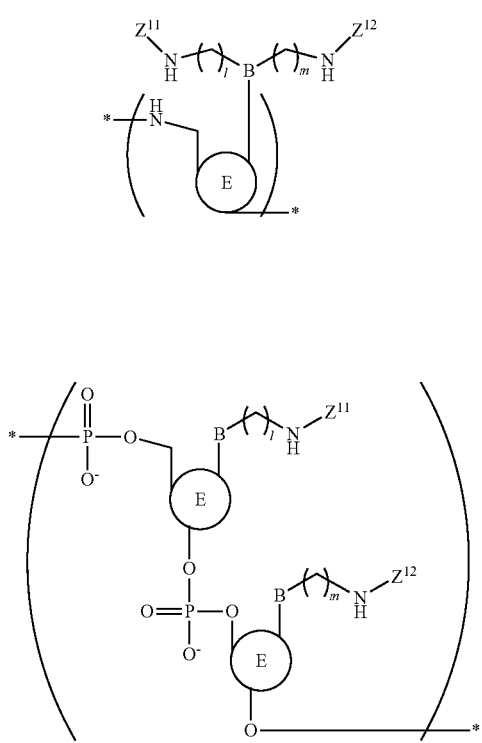

(16b-1)

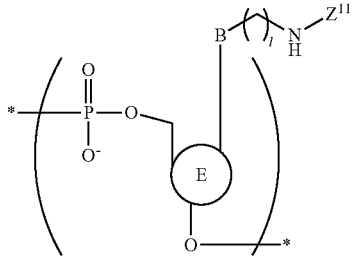

(18-1)

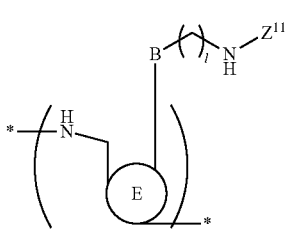

(18b-1)

where in the formulae (16-1), (16-2), (16b-1), (16b-2), (17-1), (17b-1), (18-1) and (18b-1), l, m and n' are arbitrary, l, m and n' may be identical to or different from each other, l, m and n' each may or may not contain each of C, N, O, S, P, and Si in a main chain thereof, and l, m and n' each may or may not contain each of a single bond, a double bond, a triple bond, an amide bond, an ester bond, a disulfide bond, an imino group, an ether bond, a thioether bond, and a thioester bond in the main chain, B, E, $Z^{11}$, $Z^{12}$, and b are identical to those in the formulae (16), (16b), (17), (17b), (18), and (18b), and in the formulae (16-1), (16-2), (17-1), and (18-1), at least one O atom in a phosphoric acid linkage may be substituted with an S atom.

21. The method according to claim 20, wherein in the formulae (16-1), (16-2), (16b-1), (16b-2), (17-1), (17b-1), (18-1) and (18b-1), l, m, and n are each an integer of 2 or more.

22. The method according to claim 1, wherein the nucleic acid molecule comprises at least one of nucleotide structures represented by the following chemical formulae 106, 110, 113, 117, 120, 122, 123, 124, and 114-2, geometric isomers and stereoisomers thereof, and salts thereof:

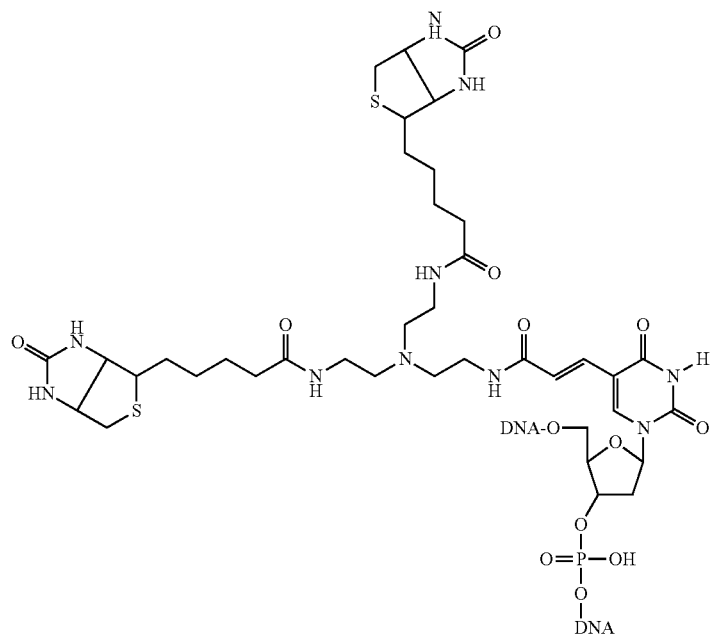
106
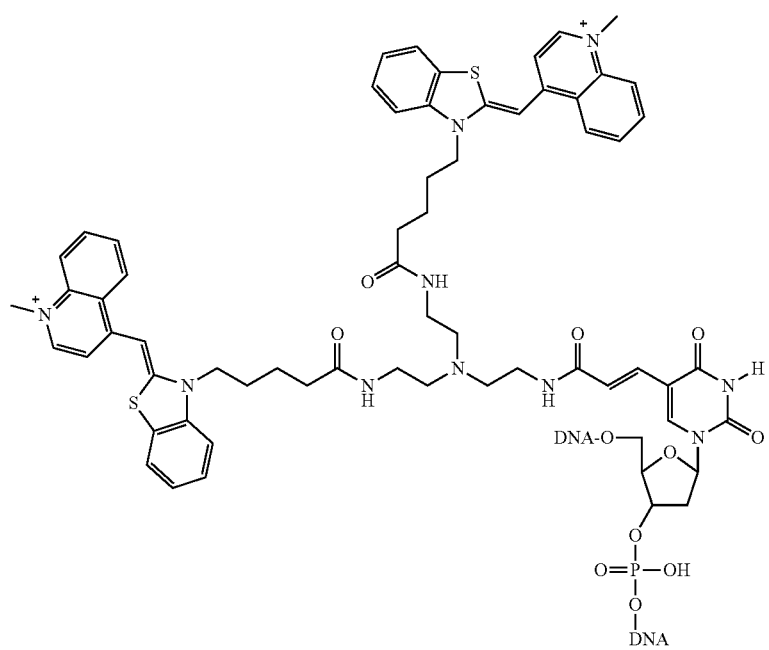
110

-continued
113
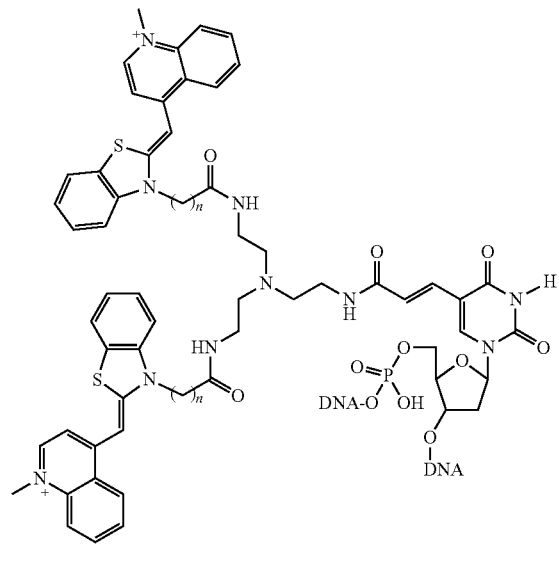
117
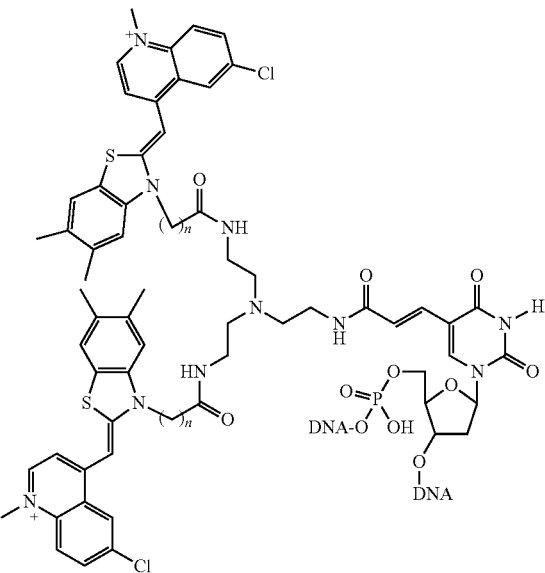
120
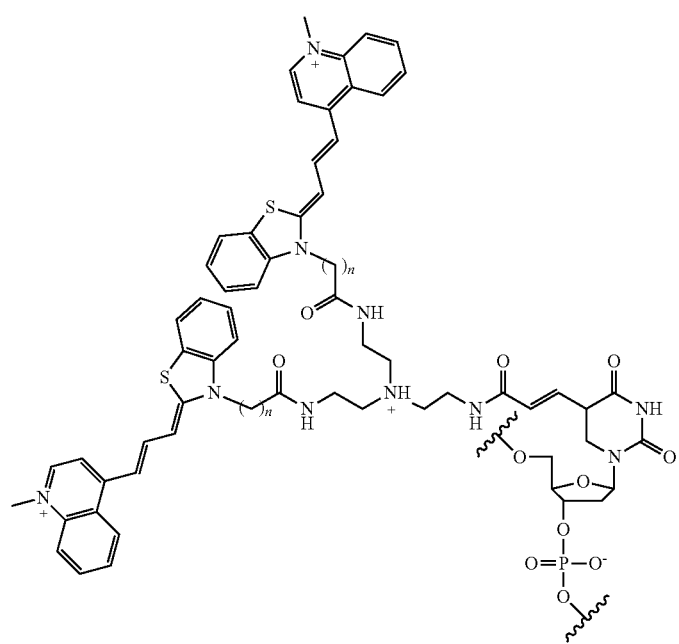

-continued (122)
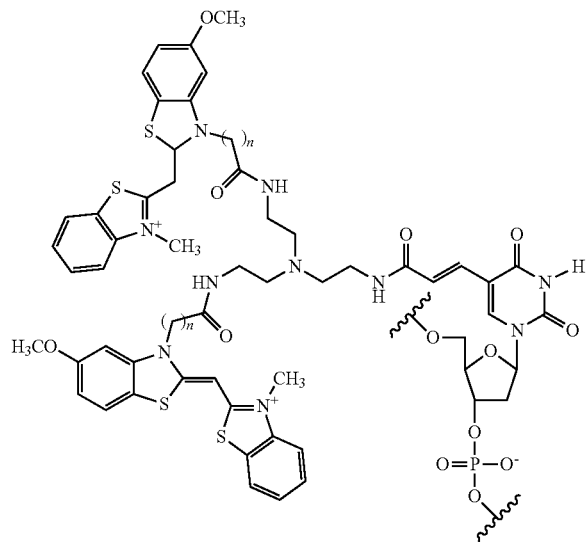

(123)
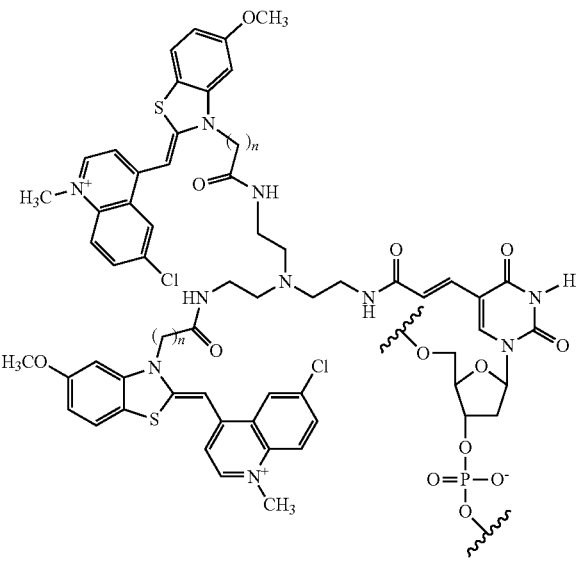

(124)
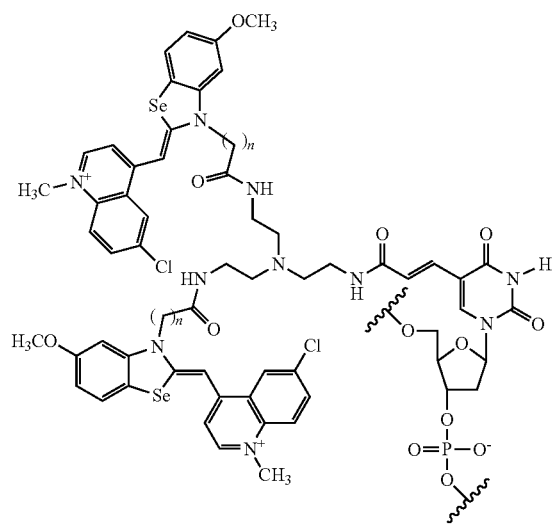

(114-2)
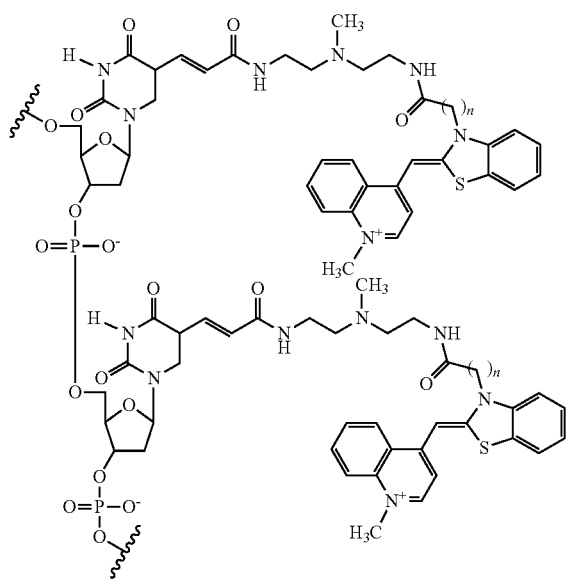

where in the chemical formulae 106, 110, 113, 117, 120, 122, 123, 124, and 114-2,
n is a positive integer.

23. The method according to claim 16, wherein the linker length n is in the range from 2 to 6.

24. The method according to claim 1, wherein the amplification reaction of the target nucleic acid is caused by a bridge PCR method.

25. The method according to claim 24, wherein
a primer pair is used as the primer,
each of primers in the primer pair comprises the label covalently bound to the primer and thus comprises the label as part thereof,
the labels covalently bound to the respective primers are each a fluorescent dye moiety that exhibits an exciton effect,
the labels are different from each other, and
in the bridge PCR method, the presence or absence of a mutation in a plurality of loci in the target nucleic acid is detected simultaneously or the expression levels of the plurality of loci are analyzed simultaneously by: adapting the labels to cause no fluorescence or fluorescence of one to three colors and carrying out fluorescent color analysis; or adapting the respective labels to exhibit fluorescence intensities different from each other and measuring the difference in fluorescence intensity.

26. The method according to claim 24, wherein
a primer pair is used as the primer,
each of primers in the primer pair comprises the label covalently bound to the primer and thus comprises the label as part thereof,
the labels covalently bound to the respective primers are each a fluorescent dye moiety that exhibits an exciton effect,
the labels are different from each other, and
in the bridge PCR method, the proportion of mutations in the entire sample containing the target nucleic acid is determined by: adapting the labels to cause no fluorescence or fluorescence of one to three colors and carrying out fluorescent color analysis; or adapting the respective labels to exhibit fluorescence intensities different from each other and measuring the difference in fluorescence intensity.

27. The method according to claim 24, wherein
a primer pair is used as the primer,
each of primers in the primer pair comprises the label covalently bound to the primer and thus comprises the label as part thereof,
the labels covalently bound to the respective primers are each a fluorescent dye moiety that exhibits an exciton effect,
the labels are different from each other, and
in the bridge PCR method, the quality of the sample containing the target nucleic acid is checked by: adapting the labels to cause no fluorescence or fluorescence of one to three colors and carrying out fluorescent color analysis; or adapting the respective labels to exhibit fluorescence intensities different from each other and measuring the difference in fluorescence intensity.

28. The method according to claim 1, wherein
the amplification reaction of the target nucleic acid is caused by an isothermal amplification method.

29. The method according to claim 1, wherein
two or more spots on the primer are immobilized on the solid phase in an arbitrary positional relationship.

30. The method according to claim 1, wherein
the target nucleic acid is RNA,
the method further comprises the step of causing a reverse transcription reaction of the RNA, and
the reverse transcription reaction is caused prior to the amplification reaction or at the same time with the amplification reaction on the solid phase having the primer immobilized thereon.

31. The method according to claim 1, wherein
the amplification reaction is caused using DNA polymerase, RNA polymerase, reverse transcriptase (reverse transcription polymerase), or RNA-dependent RNA polymerase.

32. The method according to claim 1, wherein
the presence or absence of a mutation in the target nucleic acid is detected by carrying out melting curve analysis after the amplification reaction.

33. The method according to claim 1, wherein
the melting curve analysis is carried out using a probe, and
the probe comprises a fluorescent dye moiety that exhibits an exciton effect.

34. The method according to claim 33, wherein
two or more kinds of the probes each comprising a fluorescent dye moiety that exhibits an exciton effect are used.

* * * * *